(12) United States Patent
Hoey et al.

(10) Patent No.: US 12,114,909 B2
(45) Date of Patent: Oct. 15, 2024

(54) MEDICAL SYSTEM AND METHOD OF USE

(71) Applicant: Tsunami MedTech, LLC, Menlo Park, CA (US)

(72) Inventors: Michael Hoey, Shoreview, MN (US); John H. Shadduck, Menlo Park, CA (US)

(73) Assignee: Tsunami MedTech, LLC, Menlo Park, CA (US)

( * ) Notice: Subject to any disclaimer, the term of this patent is extended or adjusted under 35 U.S.C. 154(b) by 0 days.

(21) Appl. No.: 18/308,561

(22) Filed: Apr. 27, 2023

(65) Prior Publication Data

US 2023/0329767 A1 Oct. 19, 2023

Related U.S. Application Data

(63) Continuation of application No. 17/812,382, filed on Jul. 13, 2022, now Pat. No. 11,672,584, which is a (Continued)

(51) Int. Cl.
A61B 18/04 (2006.01)
A61B 17/16 (2006.01)
(Continued)

(52) U.S. Cl.
CPC ...... *A61B 18/04* (2013.01); *A61B 2017/1648* (2013.01); *A61B 2018/00214* (2013.01); (Continued)

(58) Field of Classification Search
CPC ............ A61B 18/1492; A61B 18/1482; A61B 18/1485; A61B 18/148; A61B 2018/00577; A61B 2018/00791; A61B 2018/162; A61B 2017/00084; A61B 2018/00702; A61B 18/1206; A61B 2017/00101; A61B 2018/0016; A61B 2018/00625; A61B 17/2202; A61B 2017/00243; A61B 18/08
See application file for complete search history.

(56) References Cited

U.S. PATENT DOCUMENTS 408,899 A 8/1889 Bioch et al.
697,181 A 4/1902 Smith
(Continued)

FOREIGN PATENT DOCUMENTS

CN 201189204 2/2009
JP 06-285074 10/1994
(Continued)

OTHER PUBLICATIONS

Coda, et al., "Effects of pulmonary reventilation on gas exchange after cryolytic disobstruction of endobronchial tumors," *Minerva Medical*, vol. 72, pp. 1627-1631, Jun. 1981 (with English translation).
(Continued)

*Primary Examiner* — Rex R Holmes
(74) *Attorney, Agent, or Firm* — Levine Bagade Han LLP

(57) ABSTRACT

Methods, systems and devices for applying energy to tissue, and more particularly relates to a system for ablating or modifying structures in a body with systems and methods that generate a flow of vapor at a controlled flow rate for applying energy to the body structure.

14 Claims, 30 Drawing Sheets

Related U.S. Application Data continuation of application No. 17/452,515, filed on Oct. 27, 2021, now Pat. No. 11,413,086, which is a continuation of application No. 16/684,420, filed on Nov. 14, 2019, now Pat. No. 11,457,969, which is a continuation of application No. 15/912,332, filed on Mar. 5, 2018, now Pat. No. 10,499,973, which is a continuation of application No. 13/842,632, filed on Mar. 15, 2013, now Pat. No. 9,943,353.

(51) Int. Cl.
A61B 18/00 (2006.01)
A61B 18/12 (2006.01)
A61B 90/00 (2016.01)

(52) U.S. Cl.
CPC .......... *A61B 2018/0022* (2013.01); *A61B 2018/00285* (2013.01); *A61B 2018/00684* (2013.01); *A61B 2018/00702* (2013.01); *A61B 2018/00791* (2013.01); *A61B 2018/00863* (2013.01); *A61B 2018/046* (2013.01); *A61B 2018/048* (2013.01); *A61B 2018/1286* (2013.01); *A61B 2090/064* (2016.02); *A61B 2218/007* (2013.01)

(56) References Cited

U.S. PATENT DOCUMENTS

| | | |
|---|---|---|
| 1,719,750 A | 9/1927 | Bridge et al. |
| 3,818,913 A | 6/1974 | Wallach |
| 3,871,374 A | 3/1975 | Bolduc et al. |
| 3,880,168 A | 4/1975 | Berman |
| 3,924,628 A | 12/1975 | Droegemueller et al. |
| 3,930,505 A | 1/1976 | Wallach |
| 4,024,866 A | 5/1977 | Wallach |
| 4,083,077 A | 4/1978 | Knight et al. |
| 4,447,227 A | 5/1984 | Kotsanis |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,941,475 A | 7/1990 | Williams et al. |
| 4,950,266 A | 8/1990 | Sinofsky |
| 4,976,711 A | 12/1990 | Parins et al. |
| 4,985,027 A | 1/1991 | Dressel |
| 5,006,119 A | 4/1991 | Acker et al. |
| 5,011,566 A | 4/1991 | Hoffman |
| 5,045,056 A | 9/1991 | Behl |
| 5,078,736 A | 1/1992 | Behl |
| 5,084,043 A | 1/1992 | Hertzmann et al. |
| 5,084,044 A | 1/1992 | Quint |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,218,970 A | 6/1993 | Turnbull et al. |
| 5,242,474 A | 9/1993 | Herbst et al. |
| 5,246,436 A | 9/1993 | Rowe |
| 5,263,951 A | 11/1993 | Spears et al. |
| 5,277,201 A | 1/1994 | Stern |
| 5,277,696 A | 1/1994 | Hagen |
| 5,298,298 A | 3/1994 | Hoffman |
| 5,306,274 A | 4/1994 | Long |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,437,629 A | 8/1995 | Goldrath |
| 5,443,470 A | 8/1995 | Stern et al. |
| 5,445,168 A | 8/1995 | Krebs |
| 5,449,380 A | 9/1995 | Chin |
| 5,451,208 A | 9/1995 | Goldrath |
| 5,462,521 A | 10/1995 | Brucker et al. |
| 5,500,012 A | 3/1996 | Brucker et al. |
| 5,503,638 A | 4/1996 | Cooper et al. |
| 5,505,730 A | 4/1996 | Edwards |
| 5,524,620 A | 6/1996 | Rosenschein |
| 5,529,076 A | 6/1996 | Schachar |
| 5,540,658 A | 7/1996 | Evans et al. |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,562,720 A | 10/1996 | Stern et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,647,871 A | 7/1997 | Levine et al. |
| 5,653,692 A | 8/1997 | Masterson et al. |
| 5,662,671 A | 9/1997 | Barbut et al. |
| 5,665,074 A | 9/1997 | Kelly |
| 5,669,907 A | 9/1997 | Platt, Jr. et al. |
| 5,674,191 A | 10/1997 | Edwards et al. |
| 5,681,282 A | 10/1997 | Eggers et al. |
| 5,683,366 A | 11/1997 | Eggers et al. |
| 5,688,267 A | 11/1997 | Panescu et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,730,719 A | 3/1998 | Edwards |
| 5,735,811 A | 4/1998 | Brisken |
| 5,741,247 A | 4/1998 | Rizoiu et al. |
| 5,741,248 A | 4/1998 | Stern et al. |
| 5,743,870 A | 4/1998 | Edwards |
| 5,752,965 A | 5/1998 | Francis et al. |
| 5,754,717 A | 5/1998 | Esch |
| 5,755,753 A | 5/1998 | Knowlton |
| 5,769,880 A | 6/1998 | Truckai et al. |
| 5,782,914 A | 7/1998 | Schankereli |
| 5,785,521 A | 7/1998 | Rizoiu et al. |
| 5,800,379 A | 9/1998 | Edwards |
| 5,800,482 A | 9/1998 | Pomeranz et al. |
| 5,800,493 A | 9/1998 | Stevens et al. |
| 5,810,764 A | 9/1998 | Eggers et al. |
| 5,820,580 A | 10/1998 | Edwards et al. |
| 5,824,703 A | 10/1998 | Clark, Jr. |
| 5,827,268 A | 10/1998 | Laufer |
| 5,830,213 A | 11/1998 | Panescu et al. |
| 5,836,896 A | 11/1998 | Rosenschein |
| 5,836,906 A | 11/1998 | Edwards |
| 5,843,019 A | 12/1998 | Eggers et al. |
| 5,843,073 A | 12/1998 | Sinofsky |
| 5,871,469 A | 2/1999 | Eggers et al. |
| 5,873,855 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,911,734 A | 6/1999 | Tsugita et al. |
| 5,913,856 A | 6/1999 | Chia et al. |

(56) References Cited

U.S. PATENT DOCUMENTS

| | | |
|---|---|---|
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwin |
| 5,989,445 A | 11/1999 | Wise et al. |
| 5,997,499 A | 12/1999 | Sussman et al. |
| 6,004,509 A | 12/1999 | Dey et al. |
| 6,015,406 A | 1/2000 | Goble et al. |
| 6,024,095 A | 2/2000 | Stanley, III |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,045,532 A | 4/2000 | Eggers et al. |
| 6,045,549 A | 4/2000 | Smethers et al. |
| 6,047,700 A | 4/2000 | Eggers et al. |
| 6,053,172 A | 4/2000 | Hovda et al. |
| 6,053,909 A | 4/2000 | Shadduck |
| 6,056,746 A | 5/2000 | Goble et al. |
| 6,057,689 A | 5/2000 | Saadat |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,066,139 A | 5/2000 | Ryan et al. |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,086,585 A | 7/2000 | Hovda et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,105,581 A | 8/2000 | Eggers et al. |
| 6,106,516 A | 8/2000 | Massengill |
| 6,109,268 A | 8/2000 | Thapliyal et al. |
| 6,110,162 A | 8/2000 | Sussman et al. |
| 6,113,597 A | 9/2000 | Eggers et al. |
| 6,113,722 A | 9/2000 | Hoffman et al. |
| 6,117,109 A | 9/2000 | Eggers et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,160 A | 12/2000 | Hsei et al. |
| 6,159,194 A | 12/2000 | Eggers et al. |
| 6,159,207 A | 12/2000 | Yoon |
| 6,159,208 A | 12/2000 | Hovda et al. |
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,203,542 B1 | 3/2001 | Ellsberry et al. |
| 6,206,848 B1 | 3/2001 | Sussman et al. |
| 6,210,402 B1 | 4/2001 | Olsen et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,228,078 B1 | 5/2001 | Eggers et al. |
| 6,228,081 B1 | 5/2001 | Goble |
| 6,228,082 B1 | 5/2001 | Baker et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,254,600 B1 | 7/2001 | Willink et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,654 B1 | 7/2001 | Swartz et al. |
| 6,277,112 B1 | 8/2001 | Underwood et al. |
| 6,277,114 B1 | 8/2001 | Bullivant et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,293,942 B1 | 9/2001 | Goble et al. |
| 6,296,636 B1 | 10/2001 | Cheng et al. |
| 6,296,638 B1 | 10/2001 | Davidson et al. |
| 6,299,633 B1 | 10/2001 | Laufer |
| 6,300,150 B1 | 10/2001 | Venkatasubramanian |
| 6,306,129 B1 | 10/2001 | Little et al. |
| 6,306,134 B1 | 10/2001 | Goble et al. |
| 6,309,387 B1 | 10/2001 | Eggers et al. |
| 6,312,408 B1 | 11/2001 | Eggers et al. |
| 6,312,474 B1 | 11/2001 | Francis et al. |
| 6,315,755 B1 | 11/2001 | Sussman |
| 6,319,221 B1 | 11/2001 | Savage et al. |
| 6,319,222 B1 | 11/2001 | Andrew et al. |
| 6,322,549 B1 | 11/2001 | Eggers et al. |
| 6,327,505 B1 | 12/2001 | Medhkour et al. |
| 6,328,735 B1 | 12/2001 | Curley et al. |
| 6,331,171 B1 | 12/2001 | Cohen |
| 6,355,032 B1 | 3/2002 | Hovda et al. |
| 6,361,531 B1 | 3/2002 | Hissong |
| 6,363,937 B1 | 4/2002 | Hovda et al. |
| 6,364,877 B1 | 4/2002 | Goble et al. |
| 6,375,635 B1 | 4/2002 | Moutafis et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,699 B1 | 6/2002 | Ash |
| 6,409,723 B1 | 6/2002 | Edwards |
| 6,416,507 B1 | 7/2002 | Eggers et al. |
| 6,416,508 B1 | 7/2002 | Eggers et al. |
| 6,416,509 B1 | 7/2002 | Goble et al. |
| 6,432,103 B1 | 8/2002 | Ellsberry et al. |
| 6,440,089 B1 | 8/2002 | Shine |
| 6,443,947 B1 | 9/2002 | Marko et al. |
| 6,458,231 B1 | 10/2002 | Wapner et al. |
| 6,461,350 B1 | 10/2002 | Underwood et al. |
| 6,461,354 B1 | 10/2002 | Olsen et al. |
| 6,464,694 B1 | 10/2002 | Massengil |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,475,215 B1 | 11/2002 | Tanrisever |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,510,854 B2 | 1/2003 | Goble |
| 6,517,533 B1 | 2/2003 | Swaminathan |
| 6,517,568 B1 | 2/2003 | Sharkey et al. |
| 6,522,930 B1 | 2/2003 | Schaer et al. |
| 6,527,761 B1 | 3/2003 | Soltesz et al. |
| 6,527,766 B1 | 3/2003 | Bair |

(56) References Cited

U.S. PATENT DOCUMENTS

| | | |
|---|---|---|
| 6,540,741 B1 | 4/2003 | Underwood et al. |
| 6,544,211 B1 | 4/2003 | Andrew et al. |
| 6,544,248 B1 | 4/2003 | Bass |
| 6,544,261 B2 | 4/2003 | Ellsberry et al. |
| 6,547,784 B1 | 4/2003 | Thompson et al. |
| 6,547,810 B1 | 4/2003 | Sharkey et al. |
| 6,551,271 B2 | 4/2003 | Nguyen |
| 6,551,274 B2 | 4/2003 | Heiner |
| 6,554,780 B1 | 4/2003 | Sampson et al. |
| 6,557,559 B1 | 5/2003 | Eggers et al. |
| 6,558,379 B1 | 5/2003 | Batchelor et al. |
| 6,565,561 B1 | 5/2003 | Goble et al. |
| 6,569,146 B1 | 5/2003 | Werner et al. |
| 6,575,929 B2 | 6/2003 | Sussman et al. |
| 6,575,933 B1 | 6/2003 | Wittenberger et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,589,237 B2 | 7/2003 | Woloszko et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B2 | 9/2003 | Underwood et al. |
| 6,623,444 B2 | 9/2003 | Babaev |
| 6,626,855 B1 | 9/2003 | Weng et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,682,543 B2 | 1/2004 | Barbut et al. |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,708,056 B2 | 3/2004 | Duchon et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,749,604 B1 | 6/2004 | Eggers et al. |
| 6,755,794 B2 | 6/2004 | Soukup |
| 6,758,846 B2 | 7/2004 | Goble et al. |
| 6,763,836 B2 | 7/2004 | Tasto et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,672 B1 | 5/2005 | Eggers et al. |
| 6,896,674 B1 | 5/2005 | Wolosko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,915,806 B2 | 7/2005 | Pacek et al. |
| 6,918,903 B2 | 7/2005 | Bass |
| 6,921,385 B2 | 7/2005 | Clements et al. |
| 6,929,640 B1 | 8/2005 | Underwood et al. |
| 6,929,642 B2 | 8/2005 | Xiao et al. |
| 6,949,096 B2 | 9/2005 | Davison et al. |
| 6,955,675 B2 | 10/2005 | Jain |
| 6,960,182 B2 | 11/2005 | Moutafis et al. |
| 6,960,204 B2 | 11/2005 | Eggers et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Wolosko et al. |
| 7,004,940 B2 | 2/2006 | Ryan et al. |
| 7,004,941 B2 | 2/2006 | Tvinnereim et al. |
| 7,022,088 B2 | 4/2006 | Keast et al. |
| 7,031,504 B1 | 4/2006 | Argiro et al. |
| 7,070,596 B1 | 7/2006 | Woloszko et al. |
| 7,083,612 B2 | 8/2006 | Littrup et al. |
| 7,094,215 B2 | 8/2006 | Davison et al. |
| 7,094,249 B1 | 8/2006 | Broome et al. |
| 7,101,367 B2 | 9/2006 | Xiao et al. |
| 7,104,986 B2 | 9/2006 | Hovda et al. |
| 7,105,007 B2 | 9/2006 | Hibler |
| RE39,358 E | 10/2006 | Goble |
| 7,128,748 B2 | 10/2006 | Mooradian et al. |
| 7,131,969 B1 | 11/2006 | Hovda et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,162,303 B2 | 1/2007 | Levin et al. |
| 7,169,143 B2 | 1/2007 | Eggers et al. |
| 7,179,255 B2 | 2/2007 | Lettice et al. |
| 7,186,234 B2 | 3/2007 | Dahla et al. |
| 7,192,400 B2 | 3/2007 | Campbell et al. |
| 7,192,428 B2 | 3/2007 | Eggers et al. |
| 7,201,750 B1 | 4/2007 | Eggers et al. |
| 7,217,268 B2 | 5/2007 | Eggers et al. |
| 7,233,820 B2 | 6/2007 | Gilboa |
| 7,235,070 B2 | 6/2007 | Vanney |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,297,143 B2 | 11/2007 | Woloszko et al. |
| 7,297,145 B2 | 11/2007 | Woloszko et al. |
| 7,311,708 B2 | 12/2007 | McClurken |
| 7,320,325 B2 | 1/2008 | Duchon et al. |
| 7,335,195 B2 | 2/2008 | Mehier |
| 7,347,859 B2 | 3/2008 | Garabedian et al. |
| 7,524,315 B2 | 4/2009 | Blott et al. |
| 7,549,987 B2 | 6/2009 | Shadduck |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,674,259 B2 | 3/2010 | Shadduck |
| 7,717,948 B2 | 5/2010 | Demarais et al. |

(56) References Cited

U.S. PATENT DOCUMENTS

| | | |
|---|---|---|
| 7,756,583 B2 | 7/2010 | Demarais et al. |
| 7,815,616 B2 | 10/2010 | Boehringer et al. |
| 7,815,646 B2 | 10/2010 | Hart |
| 7,853,333 B2 | 12/2010 | Demarais |
| 7,873,417 B2 | 1/2011 | Demarais et al. |
| 7,892,229 B2 | 2/2011 | Shadduck et al. |
| 7,937,143 B2 | 5/2011 | Demarais et al. |
| 7,993,323 B2 | 8/2011 | Barry et al. |
| 8,016,823 B2 | 9/2011 | Shadduck |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,269 B2 | 5/2012 | Shadduck et al. |
| 8,192,424 B2 | 6/2012 | Woloszko |
| 8,197,470 B2 | 6/2012 | Sharkey et al. |
| 8,216,217 B2 | 7/2012 | Sharkey et al. |
| 8,221,401 B2 | 7/2012 | Sharkey et al. |
| 8,221,403 B2 | 7/2012 | Sharkey et al. |
| 8,313,485 B2 | 11/2012 | Shadduck |
| 8,444,636 B2 | 5/2013 | Shadduck et al. |
| 8,574,226 B2 | 11/2013 | Shadduck |
| 8,579,888 B2 | 11/2013 | Hoey et al. |
| 8,579,892 B2 | 11/2013 | Hoey et al. |
| 8,579,893 B2 | 11/2013 | Hoey |
| 8,585,645 B2 | 11/2013 | Barry et al. |
| 8,721,632 B2 | 5/2014 | Hoey et al. |
| 8,858,549 B2 | 10/2014 | Shadduck et al. |
| 8,900,223 B2 | 12/2014 | Shadduck |
| 8,911,430 B2 | 12/2014 | Hoey et al. |
| 9,113,944 B2 | 8/2015 | Shadduck |
| 9,161,801 B2 | 10/2015 | Hoey |
| 9,204,889 B2 | 12/2015 | Shadduck |
| 9,433,457 B2 | 9/2016 | Shadduck |
| 9,468,487 B2 | 10/2016 | Shadduck et al. |
| 9,615,875 B2 | 4/2017 | Shadduck |
| 9,662,060 B2 | 5/2017 | Peliks et al. |
| 9,700,365 B2 | 7/2017 | Sharma |
| 9,743,974 B2 | 8/2017 | Gurskis et al. |
| 9,907,599 B2 | 3/2018 | Hoey et al. |
| 9,924,992 B2 | 3/2018 | Hoey et al. |
| 9,943,353 B2 | 4/2018 | Hoey et al. |
| 9,993,290 B2 | 6/2018 | Chee et al. |
| 10,499,973 B2 | 12/2019 | Hoey et al. |
| 10,524,847 B2 | 1/2020 | Shadduck |
| 10,548,653 B2 | 2/2020 | Hoey et al. |
| 10,595,925 B2 | 3/2020 | Hoey et al. |
| 10,842,557 B2 | 11/2020 | Sharma et al. |
| 11,129,664 B2 | 9/2021 | Shadduck et al. |
| 11,141,210 B2 | 10/2021 | Shadduck |
| 11,179,187 B2 | 11/2021 | Shadduck et al. |
| 11,207,118 B2 | 12/2021 | Hoey et al. |
| 11,284,931 B2 | 3/2022 | Hoey et al. |
| 11,284,932 B2 | 3/2022 | Shadduck et al. |
| 11,413,086 B2 | 8/2022 | Hoey et al. |
| 11,457,969 B2 | 10/2022 | Hoey et al. |
| 11,478,291 B2 | 10/2022 | Shadduck et al. |
| 2001/0020167 A1 | 9/2001 | Woloszko et al. |
| 2001/0029370 A1 | 10/2001 | Hodva et al. |
| 2001/0037106 A1 | 11/2001 | Shadduck |
| 2002/0007180 A1 | 1/2002 | Wittenberger et al. |
| 2002/0013601 A1 | 1/2002 | Nobles et al. |
| 2002/0019627 A1 | 2/2002 | Maguire et al. |
| 2002/0049438 A1 | 4/2002 | Sharkey et al. |
| 2002/0077516 A1 | 6/2002 | Flanigan |
| 2002/0078956 A1 | 6/2002 | Sharpe et al. |
| 2002/0082667 A1 | 6/2002 | Shadduck |
| 2002/0095152 A1 | 7/2002 | Ciarrocca et al. |
| 2002/0111386 A1 | 8/2002 | Sekins et al. |
| 2002/0128638 A1 | 9/2002 | Chauvet et al. |
| 2002/0133147 A1 | 9/2002 | Marchitto et al. |
| 2002/0151917 A1 | 10/2002 | Barry |
| 2002/0161326 A1 | 10/2002 | Sussman et al. |
| 2002/0161362 A1 | 10/2002 | Penny et al. |
| 2002/0173815 A1 | 11/2002 | Hogendijk et al. |
| 2002/0177846 A1 | 11/2002 | Mulier et al. |
| 2002/0193789 A1 | 12/2002 | Underwood et al. |
| 2003/0028189 A1 | 2/2003 | Woloszko et al. |
| 2003/0040742 A1 | 2/2003 | Underwood et al. |
| 2003/0097126 A1 | 5/2003 | Woloszko et al. |
| 2003/0097129 A1 | 5/2003 | Davison et al. |
| 2003/0099279 A1 | 5/2003 | Venkatasubramanian et al. |
| 2003/0109869 A1 | 6/2003 | Shadduck |
| 2003/0130655 A1 | 7/2003 | Woloszko et al. |
| 2003/0130738 A1 | 7/2003 | Hovda et al. |
| 2003/0144654 A1 | 7/2003 | Hilal |
| 2003/0153905 A1 | 8/2003 | Edwards et al. |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0212395 A1 | 11/2003 | Woloszko et al. |
| 2003/0217962 A1 | 11/2003 | Childers et al. |
| 2003/0220604 A1 | 11/2003 | Al-Anazi |
| 2003/0225364 A1 | 12/2003 | Kraft et al. |
| 2004/0002698 A1 | 1/2004 | Hua Xiao et al. |
| 2004/0024398 A1 | 2/2004 | Hovda et al. |
| 2004/0024399 A1 | 2/2004 | Sharps et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0049180 A1 | 3/2004 | Sharps et al. |
| 2004/0054366 A1 | 3/2004 | Davison et al. |
| 2004/0055606 A1 | 3/2004 | Hendricksen et al. |
| 2004/0068256 A1 | 4/2004 | Rizoiu et al. |
| 2004/0068306 A1 | 4/2004 | Shadduck |
| 2004/0087937 A1 | 5/2004 | Eggers et al. |
| 2004/0116922 A1 | 6/2004 | Hovda et al. |
| 2004/0193150 A1 | 9/2004 | Sharkey et al. |
| 2004/0199226 A1 | 10/2004 | Shadduck |
| 2004/0230190 A1 | 11/2004 | Dahla et al. |
| 2004/0254532 A1 | 12/2004 | Mehier |
| 2005/0004634 A1 | 1/2005 | Ricart et al. |
| 2005/0010205 A1 | 1/2005 | Hovda et al. |
| 2005/0070894 A1 | 3/2005 | McClurken |
| 2005/0119650 A1 | 6/2005 | Sanders et al. |
| 2005/0143728 A1 | 6/2005 | Sampson et al. |
| 2005/0166925 A1 | 8/2005 | Wilson et al. |
| 2005/0171574 A1 | 8/2005 | Rubinsky et al. |
| 2005/0171582 A1 | 8/2005 | Matlock |
| 2005/0177147 A1 | 8/2005 | Vancelette et al. |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0240239 A1 | 10/2005 | Boveja et al. |
| 2005/0267467 A1 | 12/2005 | Paul et al. |
| 2005/0267468 A1 | 12/2005 | Truckai et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0058831 A1 | 3/2006 | Atad |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161147 A1 | 7/2006 | Privitera et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0224154 A1 | 10/2006 | Shadduck et al. |
| 2006/0265053 A1 | 11/2006 | Hunt |
| 2006/0271111 A1 | 11/2006 | Demarais et al. |
| 2007/0021713 A1 | 1/2007 | Kumar et al. |
| 2007/0032785 A1 | 2/2007 | Diederich et al. |
| 2007/0036417 A1 | 2/2007 | Argiro et al. |
| 2007/0066990 A1 | 3/2007 | Marsella et al. |

(56) References Cited

U.S. PATENT DOCUMENTS

| | | |
|---|---|---|
| 2007/0091087 A1 | 4/2007 | Zuiderveld |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0225744 A1 | 9/2007 | Nobles et al. |
| 2007/0239197 A1 | 10/2007 | Dubey et al. |
| 2007/0265687 A1 | 11/2007 | Deem et al. |
| 2007/0288051 A1 | 12/2007 | Beyer et al. |
| 2008/0033493 A1 | 2/2008 | Deckman et al. |
| 2008/0077201 A1 | 3/2008 | Levinson et al. |
| 2008/0097429 A1 | 4/2008 | McClurken |
| 2008/0103566 A1 | 5/2008 | Mehier |
| 2008/0110457 A1 | 5/2008 | Barry et al. |
| 2008/0114297 A1 | 5/2008 | Barry et al. |
| 2008/0125747 A1 | 5/2008 | Prokop |
| 2008/0132826 A1 | 6/2008 | Shadduck et al. |
| 2008/0135053 A1 | 6/2008 | Gruber et al. |
| 2008/0161788 A1 | 7/2008 | Dando et al. |
| 2008/0167664 A1 | 7/2008 | Payne et al. |
| 2008/0213331 A1 | 9/2008 | Gelfand et al. |
| 2008/0249467 A1 | 10/2008 | Burnett et al. |
| 2008/0255642 A1 | 10/2008 | Zarins et al. |
| 2009/0012512 A1 | 1/2009 | Utley et al. |
| 2009/0024108 A1 | 1/2009 | Lee-Sepsick et al. |
| 2009/0030412 A1 | 1/2009 | Willis et al. |
| 2009/0036948 A1 | 2/2009 | Levin et al. |
| 2009/0054871 A1 | 2/2009 | Sharkey et al. |
| 2009/0062873 A1 | 3/2009 | Wu et al. |
| 2009/0076409 A1 | 3/2009 | Wu et al. |
| 2009/0105702 A1 | 4/2009 | Shadduck |
| 2009/0105703 A1 | 4/2009 | Shadduck |
| 2009/0125009 A1 | 5/2009 | Zikorus et al. |
| 2009/0125010 A1 | 5/2009 | Sharkey et al. |
| 2009/0149846 A1* | 6/2009 | Hoey ............... A61M 25/10 606/27 |
| 2009/0216220 A1 | 8/2009 | Hoey et al. |
| 2009/0306640 A1 | 12/2009 | Glaze et al. |
| 2009/0312753 A1 | 12/2009 | Shadduck |
| 2010/0076416 A1 | 3/2010 | Hoey et al. |
| 2010/0094268 A1 | 4/2010 | Bouthillier et al. |
| 2010/0094270 A1 | 4/2010 | Sharma |
| 2010/0114083 A1 | 5/2010 | Sharma |
| 2010/0137860 A1 | 6/2010 | Demarais et al. |
| 2010/0137952 A1 | 6/2010 | Demarais et al. |
| 2010/0160905 A1 | 6/2010 | Shadduck |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0185189 A1 | 7/2010 | Hoey |
| 2010/0191112 A1 | 7/2010 | Demarais et al. |
| 2010/0198346 A1 | 8/2010 | Keogh et al. |
| 2010/0204688 A1 | 8/2010 | Hoey et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0262133 A1 | 10/2010 | Hoey et al. |
| 2010/0268307 A1 | 10/2010 | Demarais et al. |
| 2010/0286679 A1 | 11/2010 | Hoey et al. |
| 2011/0060324 A1 | 3/2011 | Wu et al. |
| 2011/0077628 A1 | 3/2011 | Hoey et al. |
| 2011/0112400 A1 | 5/2011 | Emery et al. |
| 2011/0118717 A1 | 5/2011 | Shadduck |
| 2011/0144630 A1 | 6/2011 | Loeb |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0208096 A1 | 8/2011 | Demarais et al. |
| 2011/0238144 A1 | 9/2011 | Hoey et al. |
| 2011/0257564 A1 | 10/2011 | Demarais et al. |
| 2011/0257641 A1 | 10/2011 | Hastings et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0197198 A1 | 8/2012 | Demarais et al. |
| 2012/0197252 A1 | 8/2012 | Deem et al. |
| 2012/0259271 A1 | 10/2012 | Shadduck et al. |
| 2012/0283717 A1 | 11/2012 | Sharkey et al. |
| 2013/0079772 A1 | 3/2013 | Shadduck |
| 2013/0116683 A1 | 5/2013 | Shadduck et al. |
| 2013/0178910 A1 | 7/2013 | Azamian et al. |
| 2013/0237978 A1 | 9/2013 | Shadduck et al. |
| 2014/0018890 A1 | 1/2014 | Hoey et al. |
| 2014/0025057 A1 | 1/2014 | Hoey et al. |
| 2014/0031805 A1 | 1/2014 | Shadduck |
| 2014/0088581 A1 | 3/2014 | Kelly et al. |
| 2014/0200569 A1 | 7/2014 | Shadduck |
| 2014/0200570 A1 | 7/2014 | Hoey et al. |
| 2014/0276713 A1 | 9/2014 | Hoey et al. |
| 2014/0316398 A1 | 10/2014 | Kelly et al. |
| 2014/0324037 A1 | 10/2014 | Hoey et al. |
| 2015/0025515 A1 | 1/2015 | Hoey et al. |
| 2015/0335373 A1 | 11/2015 | Chee et al. |
| 2017/0172641 A1 | 6/2017 | Shadduck |
| 2017/0258511 A1 | 9/2017 | Peliks et al. |
| 2017/0354452 A1 | 12/2017 | Gurskis et al. |
| 2018/0168713 A1 | 6/2018 | Hoey et al. |
| 2018/0193079 A1 | 7/2018 | Hoey et al. |
| 2018/0199982 A1 | 7/2018 | Hoey et al. |
| 2019/0117289 A1 | 4/2019 | Sharkey et al. |
| 2019/0117290 A1 | 4/2019 | Sharkey et al. |
| 2019/0216523 A1 | 7/2019 | Gurskis et al. |
| 2020/0078073 A1 | 3/2020 | Hoey et al. |
| 2020/0188008 A1 | 6/2020 | Hoey et al. |
| 2021/0186586 A1 | 6/2021 | Shadduck et al. |
| 2021/0204993 A1 | 7/2021 | Shadduck et al. |
| 2021/0212746 A1 | 7/2021 | Shadduck |
| 2021/0212747 A1 | 7/2021 | Shadduck |
| 2022/0047316 A1 | 2/2022 | Hoey et al. |
| 2022/0117645 A1 | 4/2022 | Shadduck et al. |
| 2022/0175438 A1 | 6/2022 | Shadduck |
| 2022/0233249 A1 | 7/2022 | Shadduck |
| 2022/0361936 A1 | 11/2022 | Hoey et al. |

FOREIGN PATENT DOCUMENTS

| | | |
|---|---|---|
| JP | 2000502585 | 3/2000 |
| JP | 2003513742 | 4/2003 |
| JP | 2010516351 | 5/2010 |
| WO | WO 1999/053853 | 10/1999 |
| WO | WO 2000/011927 | 3/2000 |
| WO | WO 2000/029055 | 5/2000 |
| WO | WO 2002/069821 | 9/2002 |
| WO | WO 2003/070302 | 8/2003 |
| WO | WO 2003/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |

(56) References Cited

FOREIGN PATENT DOCUMENTS

| WO | WO 2006/108974 | 10/2006 |
|---|---|---|
| WO | WO 2009/009398 | 1/2009 |

OTHER PUBLICATIONS

Fishman et al., "A randomized trial comparing lung-volume reduction surgery with medical therapy for severe emphysema," *N Engl J Med*, vol. 348, No. 21, pp. 2059-2073, May 22, 2003.

Gilijamse, et al., "Treatment with *Anaerobutyricum soehngenii*: a pilot study of safety and dose-response effects on glucuse metabolism in human subjects with metabolic syndrome," *NPJ: Biofilms and Microbiomes*, 6:16, pp. 1-10, Mar. 27, 2020.

Homasson, et al., "Bronchoscopic cryotherapy for airway strictures caused by tumors," *Chest*, vol. 90, No. 2, pp. 159-164, Aug. 1, 1986.

Koopen, et al., "Duodenal Anaerobutyricum soehngenii infusion stimulates GLP-1 production, ameliorates glycaemic control and beneficially shapes the duodenal transcriptome in metabolic syndrome subjects: a randomised double-blind placebo-controlled crossover study," *Gut*, vol. 71, pp. 1577-1587, Oct. 25, 2021.

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobrinchial argon plasma coagulation for treatment of hemotysis and neoplastic airway obstruction," *Chest*, vol. 119, No. 3, pp. 781-787, Mar. 1, 2001.

Moulding et al., "Preliminary studies for achieving transcervical oviduct occlusion by hot water or low-pressure steam," *Advancesin Planned Parenthood*, vol. 12, No. 2; pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren et al.; "Intrathoracic airway trees: segmentation and airway morphology analysis from low-dose CT scans;" *IEEE Trans. Med. Imaging*, vol. 24, No. 12; pp. 1529-1539, Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.

Xia, Y. et al. "Soft Lithography," *Annu. Rev. Mater. Sci.*, vol. 28, pp. 153-184, 1998, accessed at http://www.bwfoundry.com/xia.pdf.

\* cited by examiner

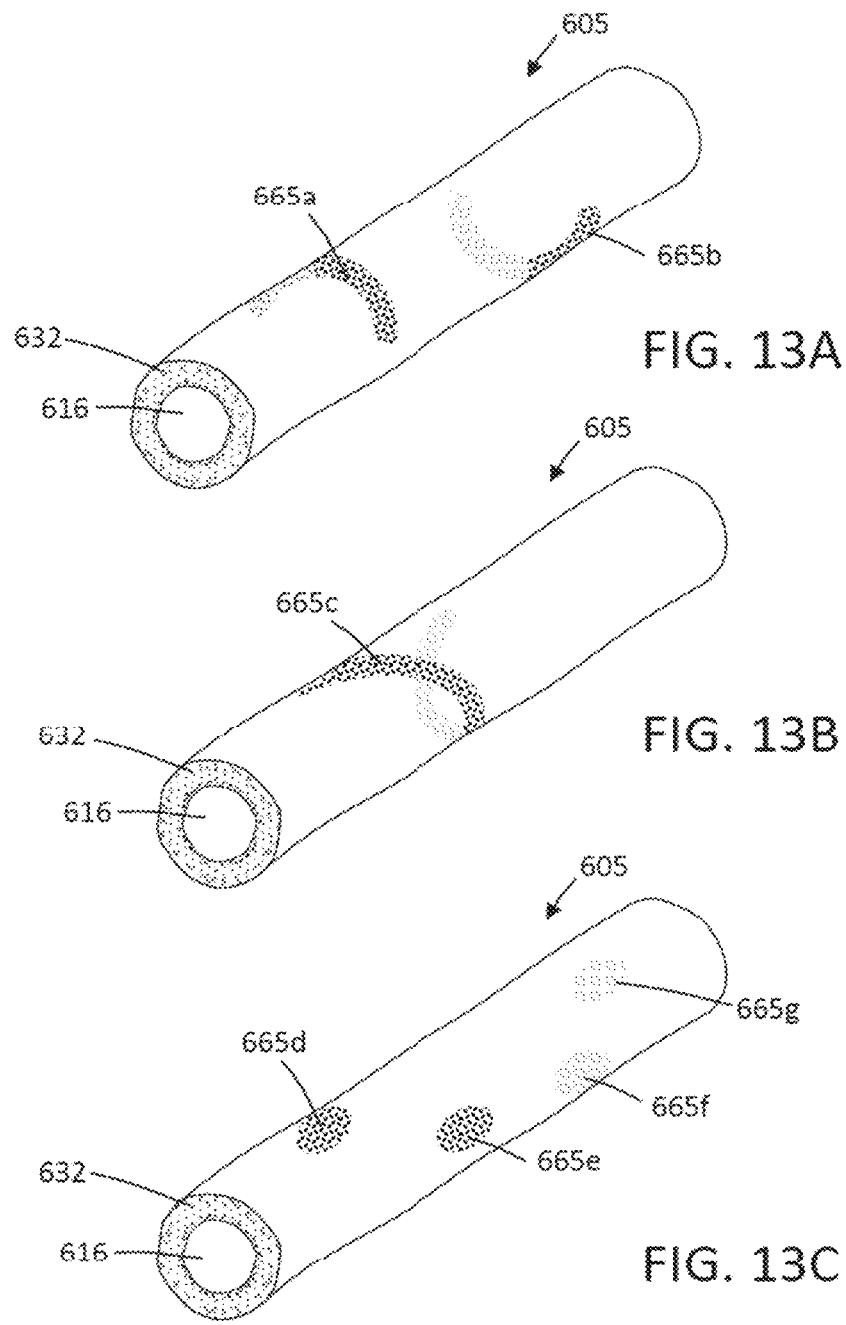

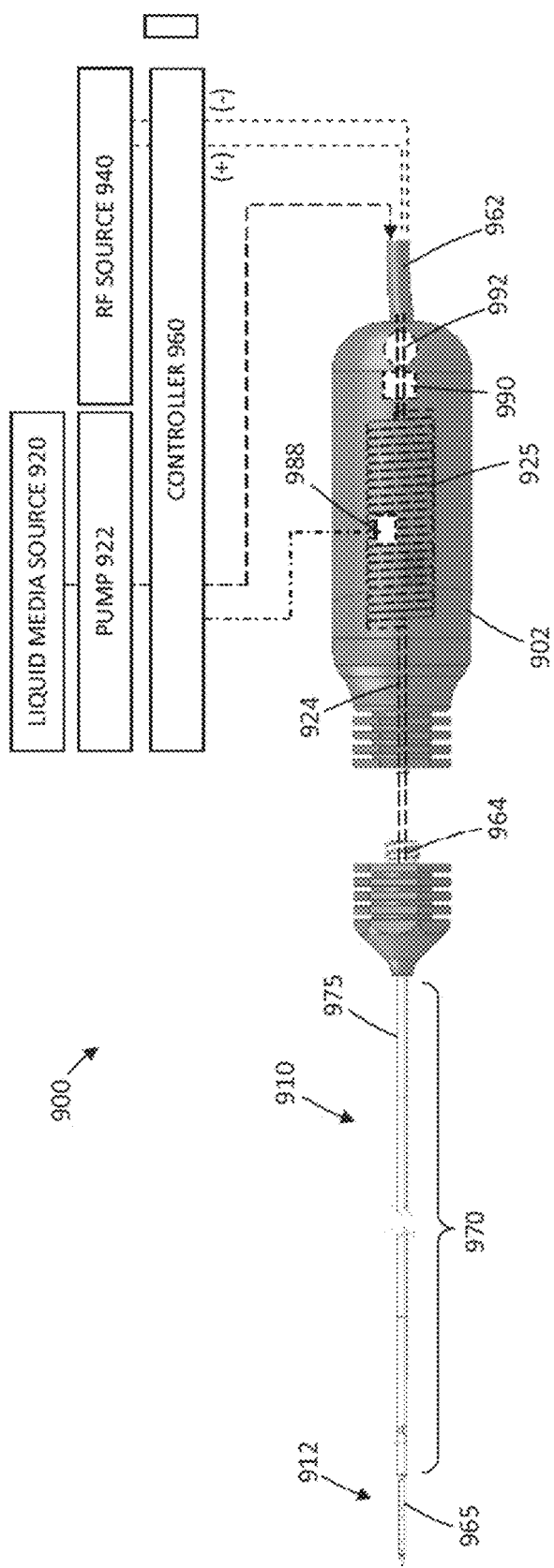
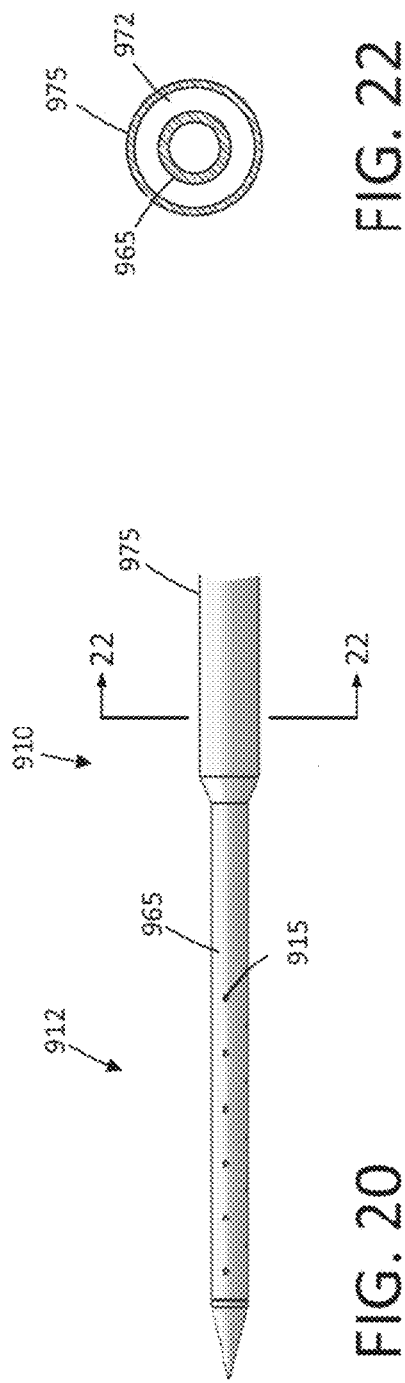

MEDICAL SYSTEM AND METHOD OF USE

CROSS-REFERENCE TO RELATED APPLICATIONS

This application is a continuation of U.S. patent application Ser. No. 17/812,382 filed Jul. 13, 2022, now U.S. Pat. No. 11,672,584, which is a continuation of U.S. patent application Ser. No. 17/452,515 filed Oct. 27, 2021, now U.S. Pat. No. 11,413,086, which is a continuation of U.S. patent application Ser. No. 16/684,420 filed Nov. 14, 2019, now U.S. Pat. No. 11,457,969, which is a continuation of U.S. patent application Ser. No. 15/912,332 filed Mar. 5, 2018, now U.S. Pat. No. 10,499,973, which is a continuation of U.S. patent application Ser. No. 13/842,632 filed Mar. 15, 2013, now U.S. Pat. No. 9,943,353, the contents of each of which are incorporated herein by reference in its entirety.

FIELD OF THE INVENTION

This invention relates to medical instruments and systems for applying energy to tissue, and more particularly relates to a system for ablating or modifying structures in a body with systems and methods that generate a flow of vapor at a controlled flow rate for applying energy to the body structure.

BACKGROUND OF THE INVENTION

Various types of medical instruments utilizing radiofrequency (RF) energy, laser energy, microwave energy and the like have been developed for delivering thermal energy to tissue, for example to ablate tissue. While such prior art forms of energy delivery work well for some applications, RF, laser and microwave energy typically cannot cause highly "controlled" and "localized" thermal effects that are desirable in controlled ablation of soft tissue for ablating a controlled depth or for the creation of precise lesions in such tissue. In general, the non-linear or non-uniform characteristics of tissue affect electromagnetic energy distributions in tissue.

What is needed are systems and methods that controllably apply thermal energy to tissue or body structure from a controlled flow of a vapor media without the lack of control often associated when RF, laser and microwave energy is applied directly to tissue.

This application is related to the following U.S. Non-provisional and Provisional applications: Application No. 61/126,647 filed on May 6, 2008 titled MEDICAL SYSTEM AND METHOD OF USE; Application No. 61/126,651 filed on May 6, 2008 titled MEDICAL SYSTEM AND METHOD OF USE; TSMT-P-T004.50-US; Application No. 61/126,612 filed on May 6, 2008 titled MEDICAL SYSTEM AND METHOD OF USE; Application No. 61/126,636 filed on May 6, 2008 titled MEDICAL SYSTEM AND METHOD OF USE; Application No. 61/130,345 filed on May 31, 2008 titled MEDICAL SYSTEM AND METHOD OF USE; Application No. 61/191,459 filed on Sep. 9, 2008 titled MEDICAL SYSTEM AND METHOD OF USE; Application No. 61/066,396 filed on Feb. 20, 2008 titled TISSUE ABLATION SYSTEM AND METHOD OF USE; Application No. 61/123,416 filed on Apr. 8, 2008 titled MEDICAL SYSTEM AND METHOD OF USE; Application No. 61/068,049 filed on Mar. 4, 2008 titled MEDICAL SYSTEM AND METHOD OF USE (TSMT-P-T005.80-US); Application No. 61/123,384 filed on Apr. 8, 2008 titled MEDICAL SYSTEM AND METHOD OF USE; Application No. 61/068,130 filed on Mar. 4, 2008 titled MEDICAL SYSTEM AND METHOD OF USE; Application No. 61/123,417 filed on Apr. 8, 2008 titled MEDICAL SYSTEM AND METHOD OF USE; Application No. 61/123,412 filed on Apr. 8, 2008 titled MEDICAL SYSTEM AND METHOD OF USE; Application No. 61/126,830 filed on May 7, 2008 titled MEDICAL SYSTEM AND METHOD OF USE; and Application No. 61/126,620 filed on May 6, 2008 titled MEDICAL SYSTEM AND METHOD OF USE.

The systems and methods described herein are also related to U.S. patent application Ser. No. 10/681,625 filed Oct. 7, 2003 titled "Medical Instruments and Techniques for Thermally-Mediated Therapies"; Ser. No. 11/158,930 filed Jun. 22, 2005 titled "Medical Instruments and Techniques for Treating Pulmonary Disorders"; Ser. No. 11/244,329; filed Oct. 5, 2005 titled "Medical Instruments and Methods of Use" and Ser. No. 11/329,381 filed Jan. 10, 2006 titled "Medical Instrument and Method of Use"; and Ser. No. 13/292,800 entitled "Medical Systems and Methods of Use" filed Nov. 9, 2011.

All of the above applications are incorporated herein by this reference and made a part of this specification, together with the specifications of all other commonly-invented applications cited in the above applications.

SUMMARY OF THE INVENTION

The present devices and methods are adapted to provide an improved means of controlled thermal energy delivery to localized tissue volumes, for example for ablating, sealing, coagulating or otherwise damaging targeted tissue.

In general, the thermally-mediated treatment method comprises causing a vapor-to-liquid phase state change in a selected media at a targeted tissue site thereby applying thermal energy substantially equal to the heat of vaporization of the selected media to the tissue site. The thermally-mediated therapy can be delivered to tissue by such vapor-to-liquid phase transitions, or "internal energy" releases, about the working surfaces of several types of instruments for ablative treatments of soft tissue. FIGS. 1A and 1B illustrate the phenomena of phase transitional releases of internal energies. Such internal energy involves energy on the molecular and atomic scale—and in polyatomic gases is directly related to intermolecular attractive forces, as well as rotational and vibrational kinetic energy. In other words, the method and devices described herein exploit the phenomenon of internal energy transitions between gaseous and liquid phases that involve very large amounts of energy compared to specific heat.

It has been found that the controlled application of such energy in a controlled media-tissue interaction solves many of the vexing problems associated with energy-tissue interactions in RF, laser and ultrasound modalities. The apparatus described herein can provide a vaporization chamber in the interior of an instrument, in an instrument working end or in a source remote from the instrument end. A source provides liquid media to the interior vaporization chamber wherein energy is applied to create a selected volume of vapor media. In the process of the liquid-to-vapor phase transition of a liquid media, for example water, large amounts of energy are added to overcome the cohesive forces between molecules in the liquid, and an additional amount of energy is required to expand the liquid 1000+ percent (P$\Delta$D) into a resulting vapor phase (see FIG. 1A). Conversely, in the vapor-to-liquid transition, such energy will be released at the phase transition at the interface with the targeted tissue site. That is, the heat of vaporization is released at the interface when the media transitions from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy at the interface with the targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. in FIG. 1A. Still referring to FIG. 1A, it can be easily understood that all other prior art ablation modalities—RF, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present devices and methods. The system can provide for insulative containment of an initial primary energy-media interaction within an interior vaporization chamber of a medical thermotherapy system. The initial, ascendant energy-media interaction delivers energy sufficient to achieve the heat of vaporization of a selected liquid media, such as water or saline solution, within an interior of the system. This aspect of the technology requires a highly controlled energy source wherein a computer controller may need to modulate energy application between very large energy densities to initially surpass the latent heat of vaporization with some energy sources (e.g. a resistive heat source, an RF energy source, a light energy source, a microwave energy source, an ultrasound source and/or an inductive heat source) and potential subsequent lesser energy densities for maintaining a high vapor quality. Additionally, a controller must control the pressure of liquid flows for replenishing the selected liquid media at the required rate and optionally for controlling propagation velocity of the vapor phase media from the working end surface of the instrument. In use, the methods described herein can comprise the controlled application of energy to achieve the heat of vaporization as in FIG. 1A and the controlled vapor-to-liquid phase transition and vapor exit pressure to thereby control the interaction of a selected volume of vapor at the interface with tissue. The vapor-to-liquid phase transition can deposit 400, 500, 600 or more cal/gram within the targeted tissue site to perform the thermal ablation with the vapor in typical pressures and temperatures.

The following disclosure includes methods for a controlled treatment of a body structure. Such methods can include a flow-based system having flow control as disclosed. These systems allow controlled application of the amount of energy delivered or allow for knowing the rate of energy delivered. The present methods and devices address the building of tissue back-pressure that might impede vapor flow thus making actual energy delivery uncertain.

In one variation, the method includes positioning a working end of a vapor delivery system at a targeted site in a body; providing a flow of liquid media at a selected fluid flow rate in the system and converting the liquid media to vapor media where a vapor flow rate corresponds to the selected fluid flow rate; and delivering the vapor media to the targeted site for a selected time interval thereby providing a controlled amount of energy to the targeted site.

The methods can include actuating an RF source configured to inductively heat a structure having a flow channel that carries the flow of liquid media.

In various alternatives, the selected fluid flow rate is maintained at a constant rate over the selected time interval. Also the method can utilize a flow controller and selecting the fluid flow rate on a controller interface.

The method can include selecting an energy application rate on a controller interface, selecting the time interval on a controller interface and/or selecting the total calories applied to tissue on a controller interface. The controller can be programmable to maintain the fluid flow rate at a constant over the selected time interval.

The flow controller can be programmable to maintain the fluid flow rate at first parameters over a first time interval and maintain the fluid flow rate at second parameters over a second time interval. Alternatively, or in combination, the flow controller is programmable to modulate the fluid flow rate over at least one selected time interval.

In another variation, a medical method for treating body structure can include providing a vapor delivery system including a flow channel and energy applicator for applying energy to a flow of liquid media in the flow channel; introducing a first flow of liquid media at a first liquid flow rate into the flow channel and converting the liquid media to vapor media, wherein a first vapor flow rate is configured for at least one of pre-heating and maintaining heat in the flow channel; and introducing a second flow of liquid media at a second liquid flow rate into the flow channel and converting the liquid media to vapor media, wherein second vapor flow rate is configured for exiting at least one vapor outlet for applying energy to the body structure.

A variation of the above method includes, after introducing a first flow of liquid media, positioning a working end of the system into or proximate the body structure, wherein the first vapor flow rate is configured to prevent at least one of gas and body fluids from migrating into the least one vapor outlet.

The present disclosure also includes medical systems for applying energy to body structure. One such system includes a handle with an elongated member coupled to the handle; an electrical source operatively coupled to a coil within the handle; an inductively heatable structure proximate positioned proximate to the coil; a pump and liquid media source in communication with a flow channel in the structure, the flow channel having an least one outlet in a distal end of the elongated member; a controller operatively coupled to the electrical source and pump; at least one of a flow sensor, pressure sensor and temperature sensor for sending signals of operating parameters to the controller; and wherein the controller is configured to operate the electrical source and pump at selected parameters to inductively heat the structure to thereby convert a flow of the liquid media to a flow of vapor media in the flow channel which exits the at least one outlet to apply energy to body structure.

The controller can include a user interface configured with user-selectable pre-selects for at least one of (i) liquid media flow rate, (ii) liquid media flow interval, (iii) modulation of the liquid media flow rate within a time interval, (iv) energy application rate corresponding to energy released in a phase change of vapor to liquid, (v) pulsed flows of the liquid media and (vi) total applied energy. Alternatively, or in combination, the controller includes an algorithm to modulate electrical energy applied to the coil to maintain the temperature of the inductively heatable structure within a selected range. In another variation, the controller includes an algorithm to modulate the liquid media flow rate to maintain the temperature of the inductively heatable structure within a selected range.

In yet another variation, the controller includes an algorithm and look-up table configured for selection of operating parameters of the electrical source corresponding to each user-selected liquid media flow rate.

Controllers described herein can also include a disable mechanism configured to disable electrical energy delivery to the coil based on feedback from at least one of the flow sensor, pressure sensor and temperature sensor or a disable mechanism configured to disable the pump and liquid media flow based on feedback from at least one of the flow sensor, pressure sensor and temperature sensor.

Another method for delivering energy to body tissue can include introducing a working end of a vapor delivery probe into a targeted site in tissue; providing a flow of a condensable vapor under first operational parameters from the working end to modify the targeted site to permit enhanced extracellular vapor propagation therein; and providing a flow of the condensable vapor under second different flow parameters from the working end to cause cell death in the targeted site.

In one variation, a first operational parameters include a first pressure that is higher than a second pressure in the second flow parameters. The first operational parameters can also include a first flow rate that is higher than a second flow rate of the second flow parameters. The first operational parameters can include a pulsed flow or a non-pulsed flow.

Another method for delivering energy to body tissue includes introducing a working end of a vapor delivery probe into a targeted site in tissue; providing a first flow of a condensable vapor from the probe for a first interval to cause convective heating within the targeted site; and providing a different second flow of condensable vapor for a second interval to cause cell death in the targeted site.

The present disclosure also includes one or more apparatus for applying energy to body structure. Such devices can include a vapor delivery system with a flow channel extending to at least one outlet in a working end; a liquid media source and pump system configured to provide a flow of the liquid media into the flow channel; a heat source for converting the flow of the liquid media into a flow of vapor media in the flow channel; and a controller adapted to control operating parameters of the liquid media source and heat source; wherein the controller includes a user interface configured with user-selectable pre-selects for at least one of (i) liquid media flow rate, (ii) liquid media flow interval, (iii) modulation of the liquid media flow rate within a time interval, (iv) energy application rate corresponding to energy released in a phase change of vapor to liquid, (v) pulsed flows of the liquid media and (vi) total applied energy corresponding to energy released in a phase change of vapor to liquid.

Variations of the device can comprise an electrical source configured to inductively heat a wall of a flow channel to thereby vaporize the flow of the liquid media therein.

As noted above, the controller can include a look-up table and algorithms configured for selection of operating parameters of the electrical source corresponding to each user-selected liquid media flow rate. The controller can also be configured to idle the vapor deliver system to provide instant-on therapeutic vapor media flows.

In one variation the controller idles the vapor deliver system by providing non-therapeutic vapor media flows through at least part of the flow channel to maintain heat in the wall of the flow channel. The controller can also idle the system by providing a liquid media flow rate of less rate than 1 cc/min together with corresponding operating parameters of the electrical source to vaporize the flow of liquid media.

The devices described herein can further include at least one temperature sensor in a wall of the flow channel configured to send signals to the controller.

Controllers used for the device can include algorithms for modulating the liquid media flow rate or the operating parameters of the heat source in response to temperature signals. The controller can also include algorithms for modulating the liquid media flow rate or the operating parameters of the heat source in response to pressure signals.

The devices described herein can include at least one pressure sensor in communication with the flow channel configured to send signals to the controller.

Another method includes a method of treating a blood pressure disorder in a human patient comprising navigating the working end of a vapor delivery catheter intravascularly to a position proximate a baroreceptor in a vessel wall and delivering a condensable vapor from the working to modify function of the baroreceptor.

Such treatments can occur in a carotid artery or any other vessel.

Another variation of a method includes a medical method for treating body structure, comprising: positioning a working end of a vapor delivery probe at or proximate to a targeted site in a body; and utilizing a pump system to provide a flow of liquid media at a predetermined fluid flow rate into the probe and converting the liquid media to vapor media thereby providing a corresponding vapor flow rate to the site, wherein the pump system is configured to deliver the liquid and vapor media at a substantially constant rate not affected by resistance to the flow of vapor media to the site.

Such method can include treatment of targeted sites, including but not limited to benign or malignant tumorous tissue; uterine fibroids; lung tissue; lung tumors or nodules; an esophagus or its inner lining; a wall of a renal artery or wall of a carotid artery; nerve tissue, a baroreceptor; a carotid body, skin, adipose tissue, bone, disc, disc nucleus, ligaments, cartilage, synovial tissue, myelomas, cervical tissue, endometrium, digestive tract tissue, stomach walls, intestinal walls, hemorrhoids, soft palate, tongue tissue, an ulcer, wart, lymph node, breast duct, sinus tissue, arterial and venous malformations, vasculature, brain tissue, nerve roots in a tooth, heart tissue and eye tissue.

Additional advantages of the method and devices are apparent from the following description, the accompanying drawings and the appended claims.

All patents, patent applications and publications mentioned in this specification are herein incorporated by reference to the same extent as if each individual publication or patent application was specifically and individually indicated to be incorporated by reference.

In addition, it is intended that combinations of aspects of the systems and methods described herein as well as the various embodiments themselves, where possible, are within the scope of this disclosure.

BRIEF DESCRIPTION OF THE DRAWINGS

FIG. 13A is a schematic view of a blood vessel following treatment with the method of FIGS. 11A-11D wherein the jetted media flows damage nerve fibers in targeted partly-annular treatment zones.

FIG. 13B is another schematic view of a blood vessel following treatment wherein the jetted media flows damage nerve fibers in targeted spiraling treatment zone.

FIG. 13C is another schematic view of a blood vessel post-treatment wherein the jetted media flows damage nerve fibers in targeted spaced apart zones.

FIG. 19 is a view of another embodiment of a vapor delivery system that includes a hand-held probe with an inductive heating form of vapor generator carried in a probe handle together with a disposable, de-matable vapor delivery needle.

FIG. 20 is an enlarged view of the working end of the vapor delivery needle of FIG. 19.

FIG. 22 is a cross-section of the vapor delivery needle shaft of FIG. 19.

DETAILED DESCRIPTION OF THE INVENTION

As used in the specification, "a" or "an" means one or more. As used in the claim(s), when used in conjunction with the word "comprising", the words "a" or "an" mean one or more. As used herein, "another" means as least a second or more. "Substantially" or "substantial" mean largely but not entirely. For example, substantially may mean about 10% to about 99.999, about 25% to about 99.999% or about 50% to about 99.999%.

Treatment Liquid Source, Energy Source, Controller

Figure 2:
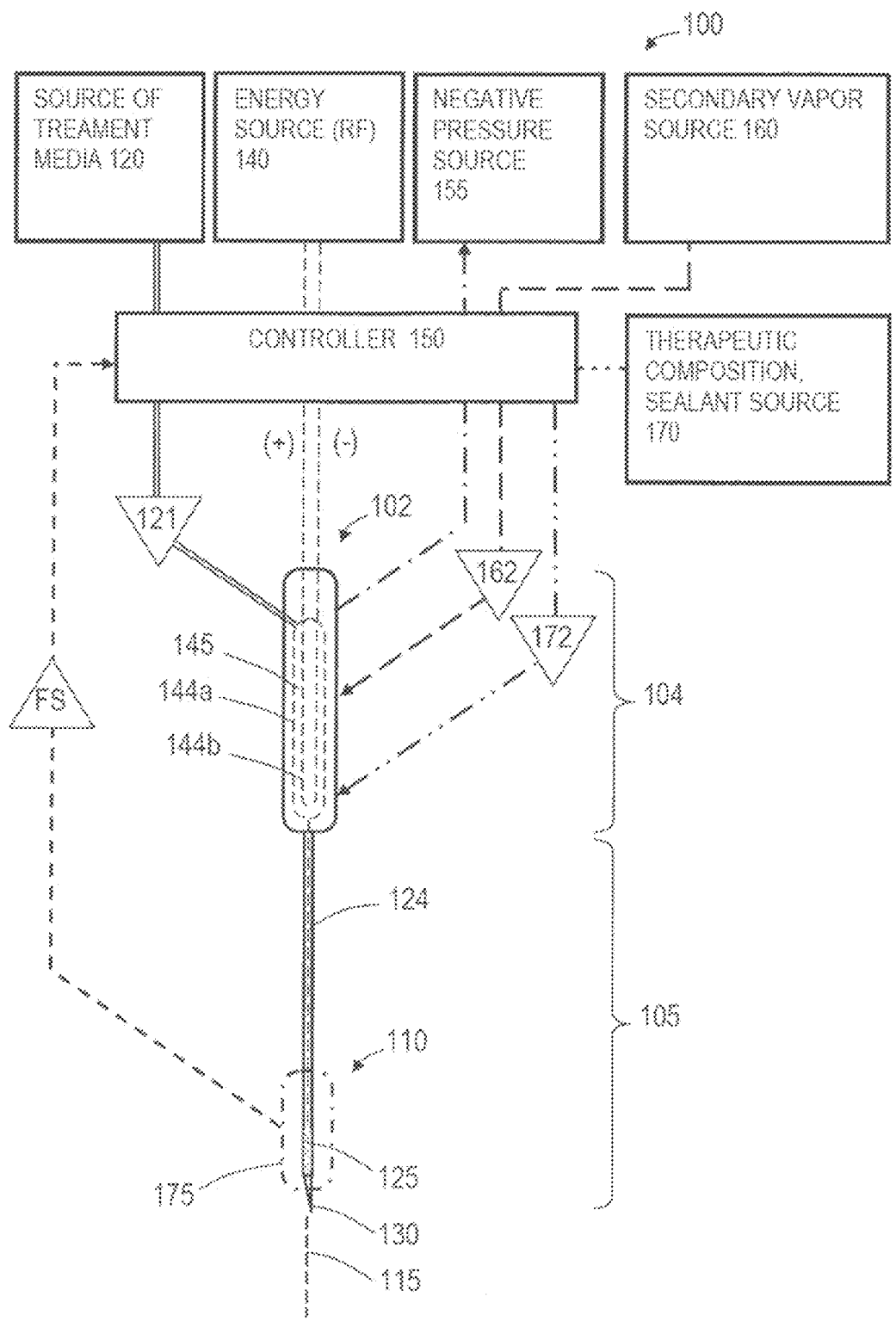
FIG. 2 provides a schematic view of a variation of a medical system adapted for treating a tissue target, wherein the treatment comprises an ablation or thermotherapy and the tissue target can comprise any mammalian soft tissue to be ablated, sealed, contracted.

Referring to FIG. 2, a schematic view of a variation of a medical system 100 is shown where the system 100 is adapted for treating a tissue target, wherein the treatment comprises an ablation or thermotherapy and the tissue target can comprise any mammalian soft tissue to be ablated, sealed, contracted, coagulated, damaged or treated to elicit an immune response. The system 100 can include an instrument or probe body 102 with a proximal handle end 104 and an extension portion 105 having a distal or working end indicated at 110. In one embodiment depicted in FIG. 2, the handle end 104 and extension portion 105 generally extend about longitudinal axis 115. In the embodiment of FIG. 2, the extension portion 105 is a substantially rigid tubular member with at least one flow channel therein, but additional variations can encompass extension portions 105 of any mean diameter and any axial length, rigid or flexible, suited for treating a particular tissue target. In one embodiment, a rigid extension portion 105 can comprise a 20 Ga. to 40 Ga. needle with a short length for thermal treatment of a patient's cornea or a somewhat longer length for treating a patient's retina. In another embodiment, an elongate extension portion 105 of a vapor delivery tool can comprise a single needle or a plurality of needles having suitable lengths for tumor or soft tissue ablation in a liver, breast, gall bladder, prostate, bone and the like. In another embodiment, an elongate extension portion 105 can comprise a flexible catheter for introduction through a body lumen to access a tissue target, with a diameter ranging from about 1 to 10 mm. In another embodiment, the extension portion 105 or working end 110 can be articulatable, deflectable or deformable. The probe handle end 104 can be configured as a hand-held member, or can be configured for coupling to a robotic surgical system. In another embodiment, the working end 110 carries an openable and closeable structure for capturing tissue between first and second tissue-engaging surfaces, which can comprise actuatable components such as one or more clamps, jaws, loops, snares and the like. The proximal handle end 104 of the probe can carry various actuator mechanisms known in the art for actuating components of the system 100, and/or one or more footswitches can be used for actuating components of the system.

As can be seen in FIG. 2, the system 100 further includes a source 120 of a flowable liquid treatment media 121 that communicates with a flow channel 124 extending through the probe body 102 to at least one outlet 125 in the working end 110. The outlet 125 can be singular or multiple and have any suitable dimension and orientation as will be described further below. The distal tip 130 of the probe can be sharp for penetrating tissue, or can be blunt-tipped or open-ended with outlet 125. Alternatively, the working end 110 can be configured in any of the various embodiments shown in FIGS. 6A-6M and described further below.

In one embodiment shown in FIG. 2, an RF energy source 140 is operatively connected to a thermal energy source or emitter (e.g., opposing polarity electrodes 144a, 144b) in interior chamber 145 in the proximal handle end 104 of the probe for converting the liquid treatment media 121 from a liquid phase media to a non-liquid vapor phase media 122 with a heat of vaporization in the range of 60° C. to 200° C., or 80° C. to 120° C. A vaporization system using RF energy and opposing polarity electrodes is disclosed in co-pending U.S. patent application Ser. No. 11/329,381 which is incorporated herein by reference. Another embodiment of a vapor generation system is described below in the Section titled "INDUCTIVE VAPOR GENERATION SYSTEMS". In any system embodiment, for example in the system of FIG. 2, a controller 150 is provided that comprises a computer control system configured for controlling the operating parameters of inflows of liquid treatment media source 120 and energy applied to the liquid media by an energy source to cause the liquid-to-vapor conversion. The vapor generation systems described herein can consistently produce a high quality vapor having a temperature of at least 80° C., 100° C. 120° C., 140° C. and 160° C.

As can be seen in FIG. 2, the medical system 100 can further include a negative pressure or aspiration source indicated at 155 that is in fluid communication with a flow channel in probe 102 and working end 110 for aspirating treatment vapor media 122, body fluids, ablation by-products, tissue debris and the like from a targeted treatment site, as will be further described below. In FIG. 2, the controller 150 also is capable of modulating the operating parameters of the negative pressure source 155 to extract vapor media 122 from the treatment site or from the interior of the working end 110 by means of a recirculation channel to control flows of vapor media 122 as will be described further below.

In another embodiment, still referring to FIG. 2, medical system 100 further includes secondary media source 160 for providing an inflow of a second media, for example a biocompatible gas such as $CO_2$. In one method, a second media that includes at least one of depressurized $CO_2$, $N_2$, $O_2$ or $H_2O$ can be introduced and combined with the vapor media 122. This second media 162 is introduced into the flow of non-ionized vapor media for lowering the mass average temperature of the combined flow for treating tissue. In another embodiment, the medical system 100 includes a source 170 of a therapeutic or pharmacological agent or a sealant composition indicated at 172 for providing an additional treatment effect in the target tissue. In FIG. 2, the controller indicated at 150 also is configured to modulate the operating parameters of source 160 and 170 to control inflows of a secondary vapor 162 and therapeutic agents, sealants or other compositions indicated at 172.

In FIG. 2, it is further illustrated that a sensor system 175 is carried within the probe 102 for monitoring a parameter of the vapor media 122 to thereby provide a feedback signal FS to the controller 150 by means of feedback circuitry to thereby allow the controller to modulate the output or operating parameters of treatment media source 120, energy source 140, negative pressure source 155, secondary media source 160 and therapeutic agent source 170. The sensor system 175 is further described below, and in one embodiment comprises a flow sensor to determine flows or the lack of a vapor flow. In another embodiment, the sensor system 175 includes a temperature sensor. In another embodiment, sensor system 175 includes a pressure sensor. In another embodiment, the sensor system 175 includes a sensor arrangement for determining the quality of the vapor media, e.g., in terms of vapor saturation or the like. The sensor systems will be described in more detail below.

Figure 3:
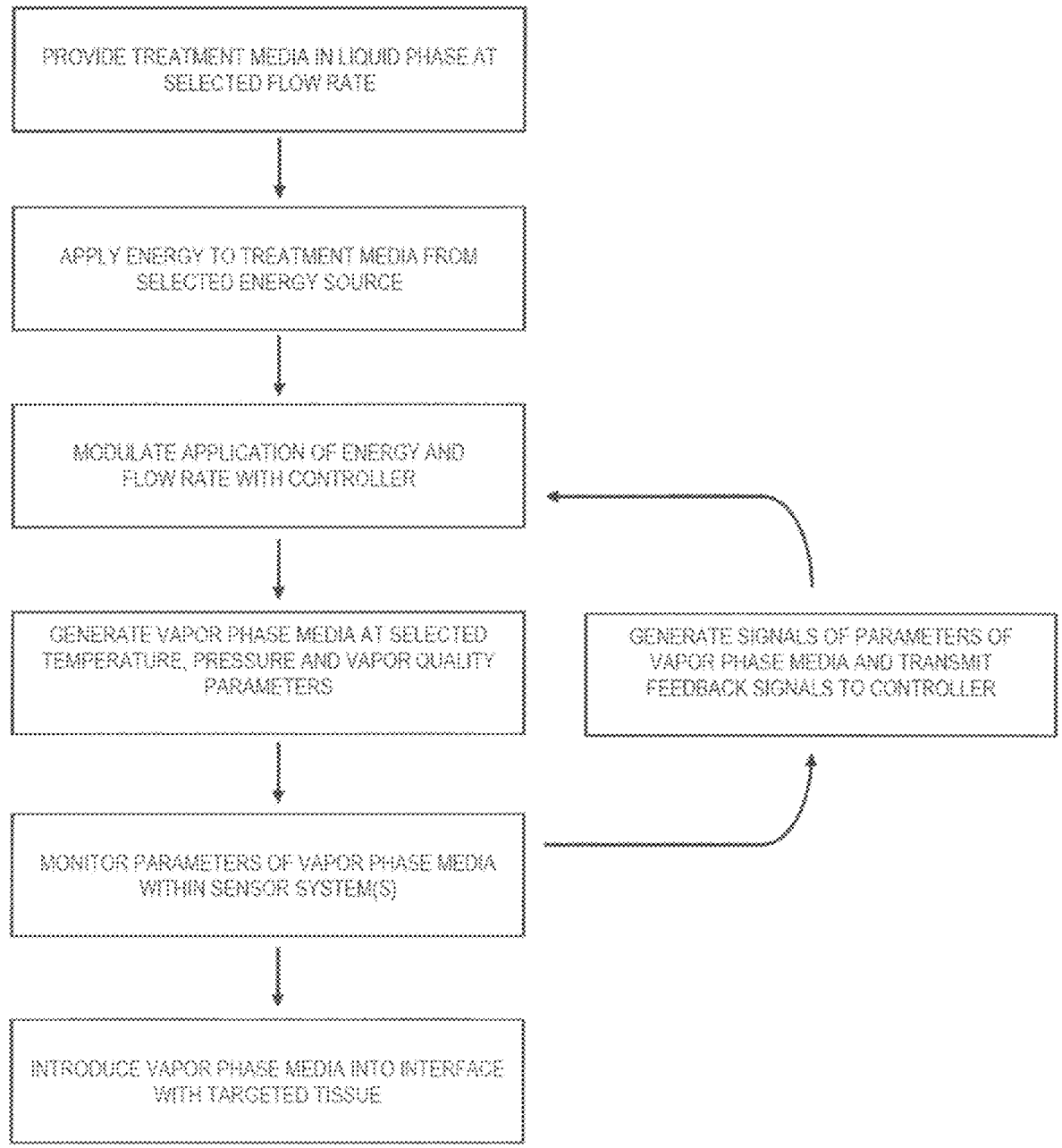
FIG. 3 is a block diagram of an exemplary control method.

Now turning to FIGS. 2 and 3, the controller 150 is capable of all operational parameters of system 100, including modulating the operational parameters in response to preset values or in response to feedback signals FS from sensor system(s) 175 within the system 100 and probe working end 110. In one embodiment, as depicted in the block diagram of FIG. 3, the system 100 and controller 150 are capable of providing or modulating an operational parameter comprising a flow rate of liquid phase treatment media 122 from pressurized source 120, wherein the flow rate is within a range from about 0.001 to 20 ml/min, 0.010 to 10 ml/min or 0.050 to 5 ml/min. The system 100 and controller 150 are further capable of providing or modulating another operational parameter comprising the inflow pressure of liquid phase treatment media 121 in a range from 0.5 to 1000 psi, 5 to 500 psi, or 25 to 200 psi. The system 100 and controller 150 are further capable of providing or modulating another operational parameter comprising a selected level of energy capable of converting the liquid phase media into a non-liquid, non-ionized gas phase media, wherein the energy level is within a range of about 5 to 2,500 watts; 10 to 1,000 watts or 25 to 500 watts. The system 100 and controller 150 are capable of applying the selected level of energy to provide the phase conversion in the treatment media over an interval ranging from 0.1 seconds to 10 minutes; 0.5 seconds to 5 minutes, and 1 second to 60 seconds. The system 100 and controller 150 are further capable of controlling parameters of the vapor phase media including the flow rate of non-ionized vapor media proximate an outlet 125, the pressure of vapor media 122 at the outlet, the temperature or mass average temperature of the vapor media, and the quality of vapor media as will be described further below.

Figure 4A:
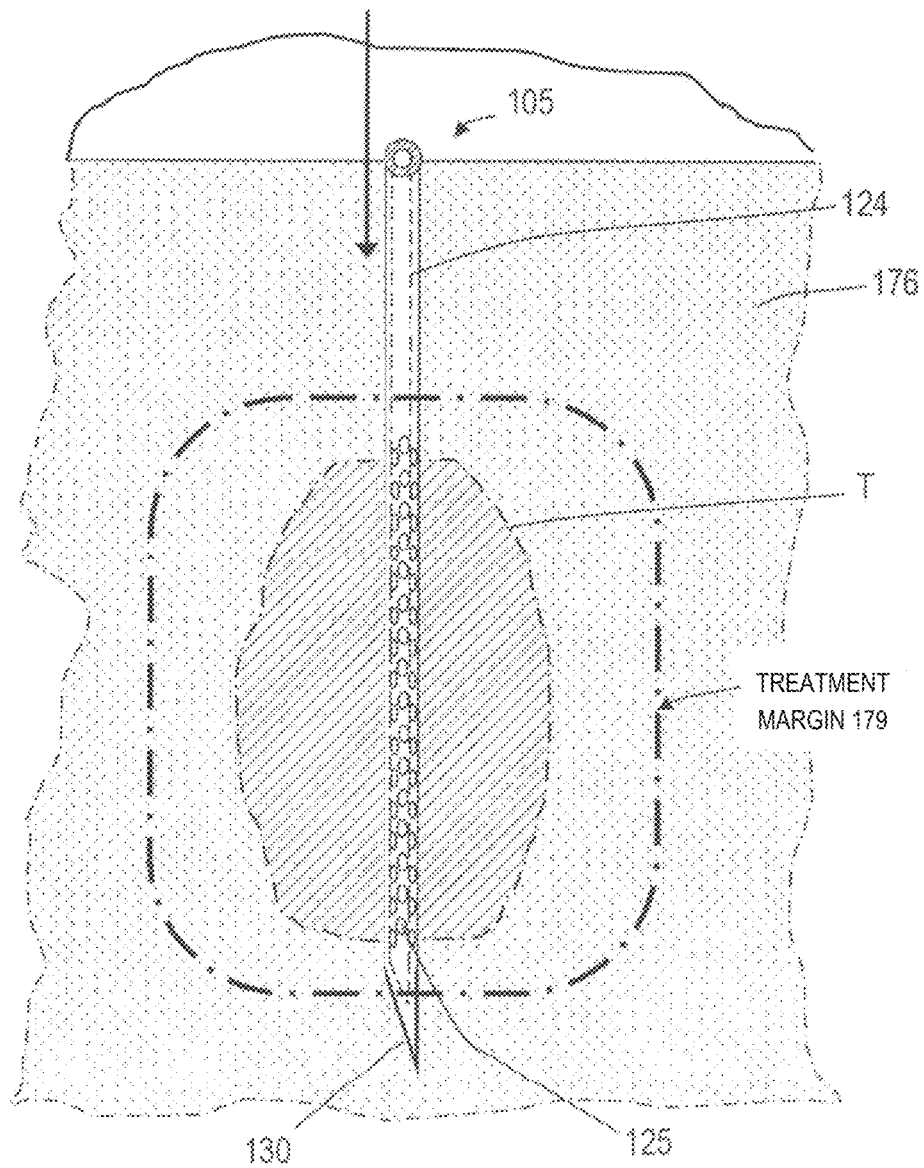
FIG. 4A is an illustration of the working end of FIG. 2 being introduced into soft tissue to treat a targeted tissue volume.
Figure 4B:
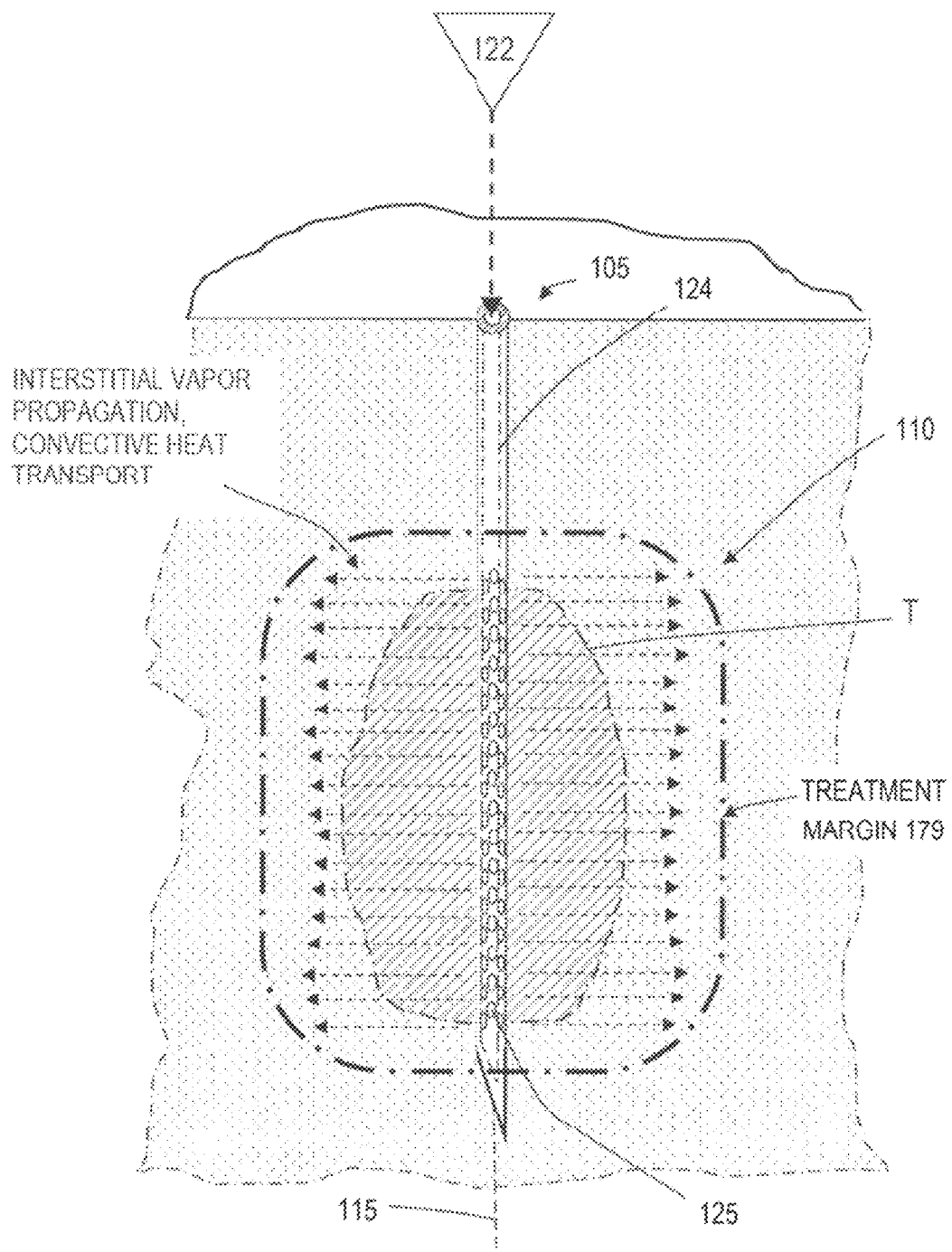
FIG. 4B is an illustration of the working end of FIG. 4A showing the propagation of vapor media in tissue in a method of use in ablating a tumor.

FIGS. 4A and 4B illustrate a working end 110 of the system 100 of FIG. 2 and a method of use. As can be seen in FIG. 4A, a working end 110 is singular and configured as a needle-like device for penetrating into and/or through a targeted tissue T such as a tumor in a tissue volume 176. The tumor can be benign, malignant, hyperplastic or hypertrophic tissue, for example, in a patient's breast, uterus, lung, liver, kidney, gall bladder, stomach, pancreas, colon, GI tract, bladder, prostate, bone, vertebra, eye, brain or other tissue. In one variation, the extension portion 104 is made of a metal, for example, stainless steel. Alternatively or additionally, at least some portions of the extension portion can be fabricated of a polymer material such as PEEK, PTFE, Nylon or polypropylene. Also optionally, one or more components of the extension portion are formed of coated metal, for example, a coating with Teflon® to reduce friction upon insertion and to prevent tissue sticking following use. In one embodiment as shown in FIG. 4A, the working end 110 includes a plurality of outlets 125 that allow vapor media to be ejected in all radial directions over a selected treatment length of the working end. In another embodiment, the plurality of outlets can be symmetric or asymmetric axially or angularly about the working end 110.

Figure 5:
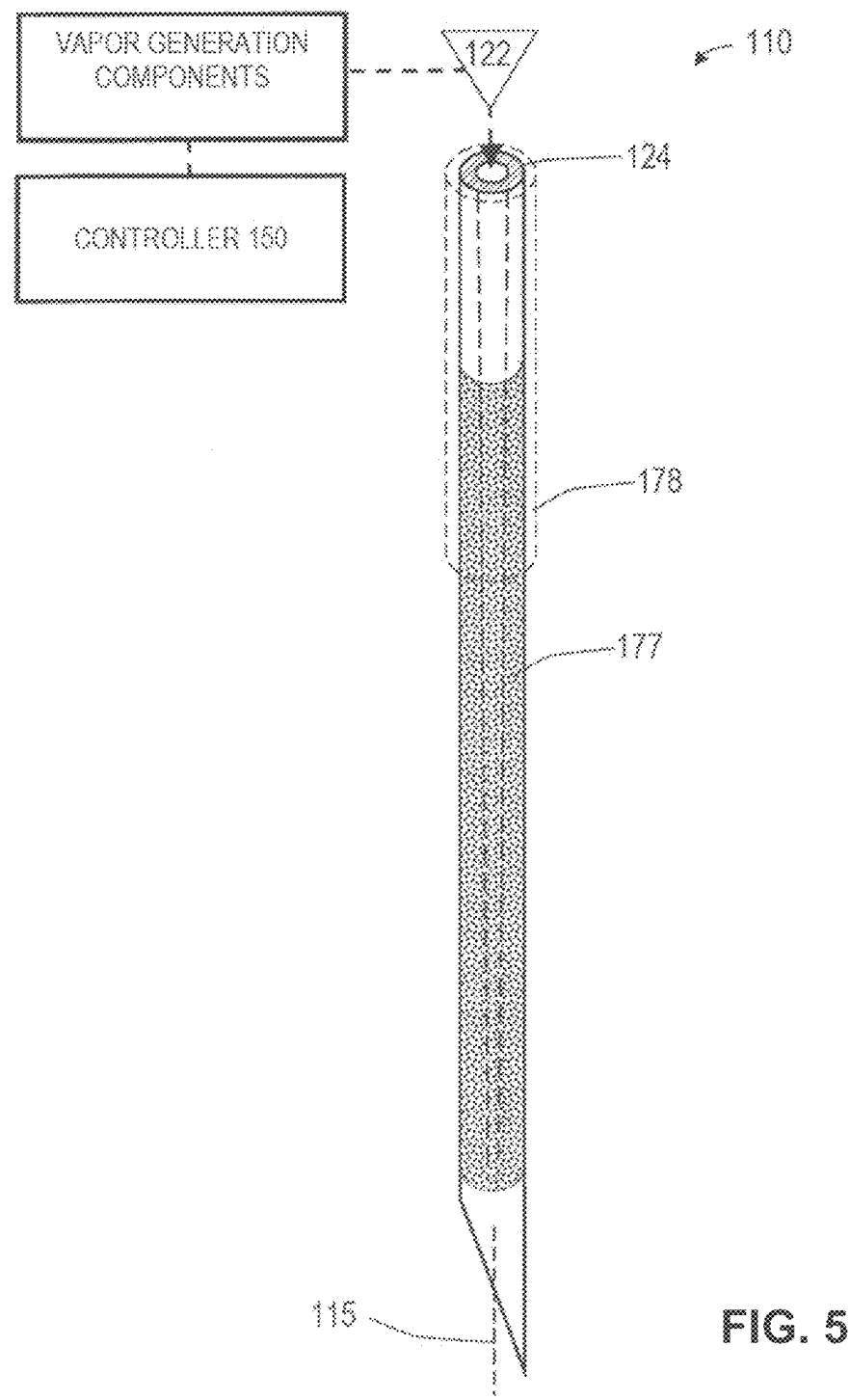
FIG. 5 is an illustration of a working end similar to FIGS. 4A-4B with vapor outlets comprising microporosities in a porous wall.

In one embodiment, the outer diameter of extension portion 105 or working end 110 is, for example, 0.2 mm, 0.5 mm, 1 mm, 2 mm, 5 mm or an intermediate, smaller or larger diameter. Optionally, the outlets can comprise microporosities 177 in a porous material as illustrated in FIG. 5 for diffusion and distribution of vapor media flows about the surface of the working end. In one such embodiment, such porosities provide a greater restriction to vapor media outflows than adjacent targeted tissue, which can vary greatly in vapor permeability. In this case, such microporosities ensure that vapor media outflows will occur substantially uniformly over the surface of the working end. Optionally, the wall thickness of the working end 110 is from 0.05 to 0.5 mm. Optionally, the wall thickness decreases or increases towards the distal sharp tip 130 (FIG. 5). In one embodiment, the dimensions and orientations of outlets 125 are selected to diffuse and/or direct vapor media propagation into targeted tissue T and more particularly to direct vapor media into all targeted tissue to cause extracellular vapor propagation and thus convective heating of the target tissue as indicated in FIG. 4B. As shown in FIGS. 4A-4B, the shape of the outlets 125 can vary, for example, round, ellipsoid, rectangular, radially and/or axially symmetric or asymmetric. As shown in FIG. 5, a sleeve 178 can be advanced or retracted relative to the outlets 125 to provide a selected exposure of such outlets to provide vapor injection over a selected length of the working end 110. Optionally, the outlets can be oriented in various ways, for example so that vapor media 122 is ejected perpendicular to a surface of working end 110, or ejected is at an angle relative to the axis 115 or angled relative to a plane perpendicular to the axis. Optionally, the outlets can be disposed on a selected side or within a selected axial portion of working end, wherein rotation or axial movement of the working end will direct vapor propagation and energy delivery in a selected direction. In another embodiment, the working end 110 can be disposed in a secondary outer sleeve that has apertures in a particular side thereof for angular/axial movement in targeted tissue for directing vapor flows into the tissue.

FIG. 4B illustrates the working end 110 of system 100 ejecting vapor media from the working end under selected operating parameters, for example a selected pressure, vapor temperature, vapor quantity, vapor quality and duration of flow. The duration of flow can be a selected pre-set or the hyperechoic aspect of the vapor flow can be imaged by means of ultrasound to allow the termination of vapor flows by observation of the vapor plume relative to targeted tissue T. As depicted schematically in FIG. 4B, the vapor can propagate extracellularly in soft tissue to provide intense convective heating as the vapor collapses into water droplets which result in effective tissue ablation and cell death. As further depicted in FIG. 4B, the tissue is treated to provide an effective treatment margin 179 around a targeted tumorous volume. The vapor delivery step is continuous or can be repeated at a high repetition rate to cause a pulsed form of convective heating and thermal energy delivery to the targeted tissue. The repetition rate vapor flows can vary, for example with flow durations intervals from 0.01 to 20 seconds and intermediate off intervals from 0.01 to 5 seconds or intermediate, larger or smaller intervals.

In an exemplary embodiment as shown in FIGS. 4A-4B, the extension portion 105 can be a unitary member such as a needle. In another embodiment, the extension portion 105 or working end 110 can be a detachable flexible body or rigid body, for example of any type selected by a user with outlet sizes and orientations for a particular procedure with the working end attached by threads or Luer fitting to a more proximal portion of probe 102.

Figure 6A:
FIG. 6A is a schematic view of a needle-type working end of a vapor delivery tool for applying energy to tissue.
Figure 6B:
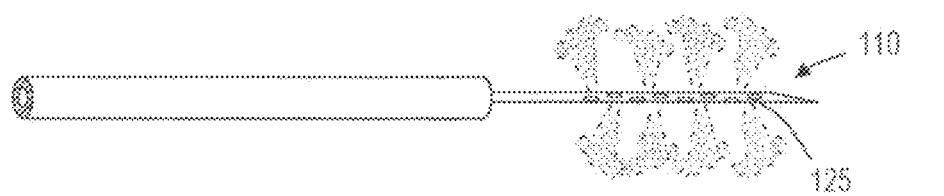
FIG. 6B is a schematic view of an alternative needle-type working end similar to FIG. 6A.
Figure 6C:
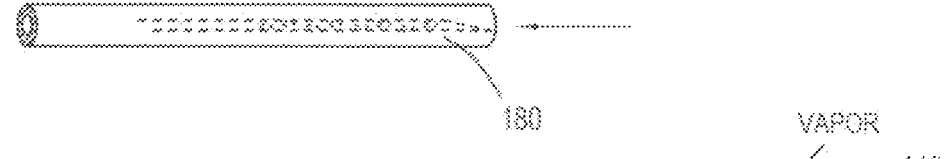
FIG. 6C is a schematic view of a retractable needle-type working end similar to FIG. 6B.
Figure 6D:
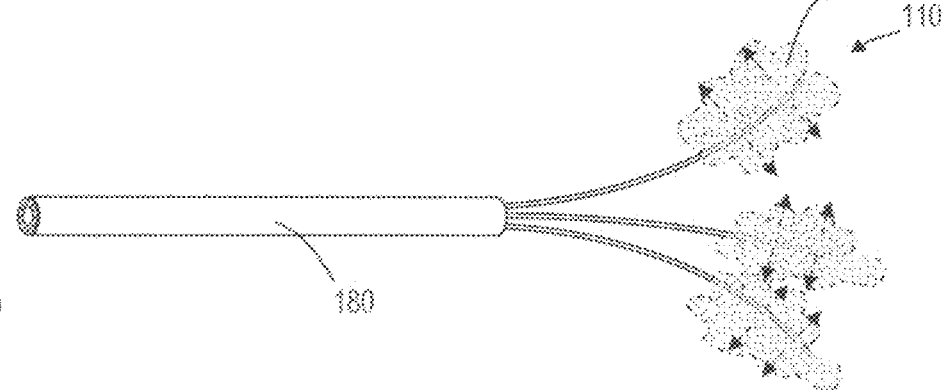
FIG. 6D is a schematic view of a working end with multiple shape-memory needles.
Figure 6E:
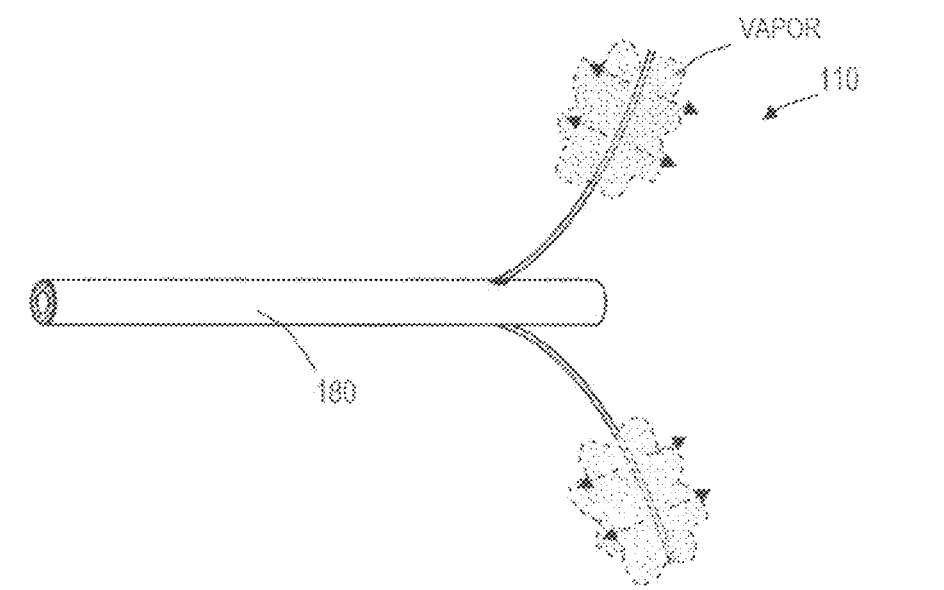
FIG. 6E is a schematic view of a working end with deflectable needles.
Figure 6F:
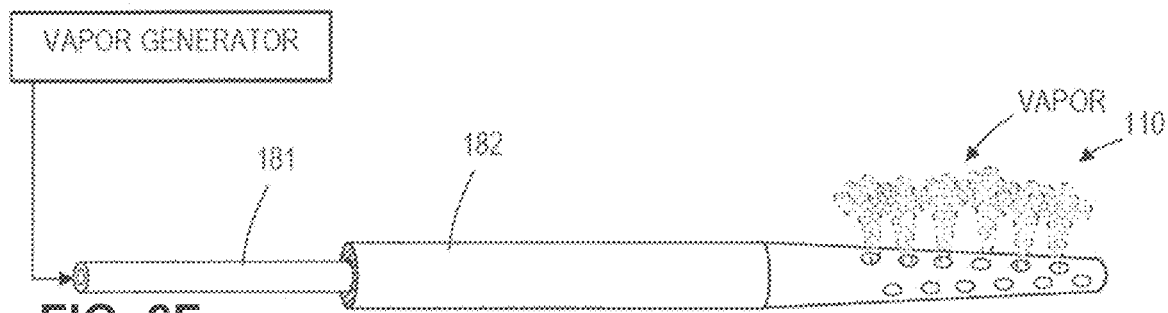
FIG. 6F is a schematic view of a working end with a rotating element for directing vapor flows.
Figure 6G:
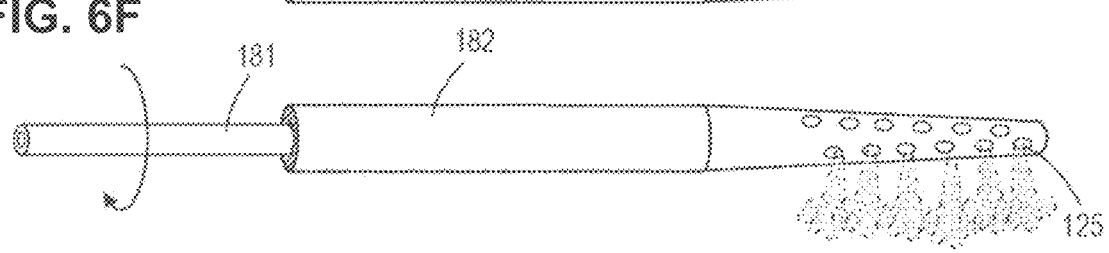
FIG. 6G is another view of the working end of FIG. 6F.

In other embodiments, the working end 110 can comprise needles with terminal outlets or side outlets as shown in FIGS. 6A-6B. The needle of FIGS. 6A and 6B can comprise a retractable needle as shown in FIG. 6C capable of retraction into probe or sheath 180 for navigation of the probe through a body passageway or for blocking a portion of the vapor outlets 125 to control the geometry of the vapor-tissue interface. In another embodiment shown in FIG. 6D, the working end 110 can have multiple retractable needles that are of a shape memory material. In another embodiment as depicted in FIG. 6E, the working end 110 can have at least one deflectable and retractable needle that deflects relative to an axis of the probe 180 when advanced from the probe. In another embodiment, the working end 110 as shown in FIGS. 6F-6G can comprise a dual sleeve assembly wherein vapor-carrying inner sleeve 181 rotates within outer sleeve 182 and wherein outlets in the inner sleeve 181 only register with outlets 125 in outer sleeve 182 at selected angles of relative rotation to allow vapor to exit the outlets. This assembly thus provides for a method of pulsed vapor application from outlets in the working end. The rotation can be from about 1 rpm to 1000 rpm.

Figure 6H:
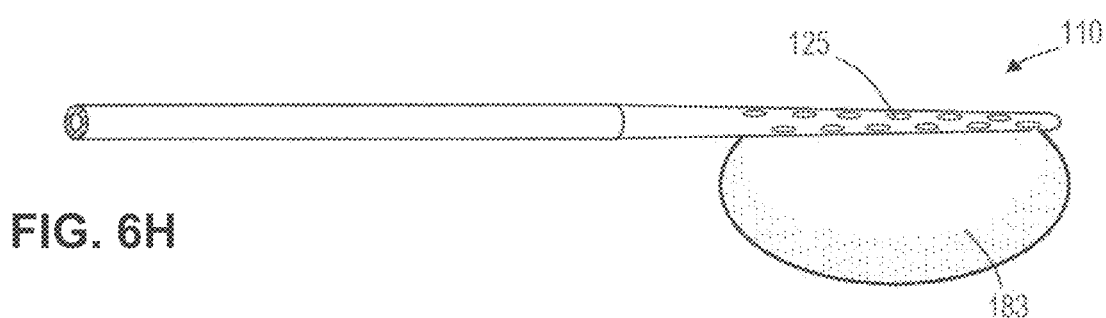
FIG. 6H is a schematic view of a working end with a balloon.
Figure 6I:
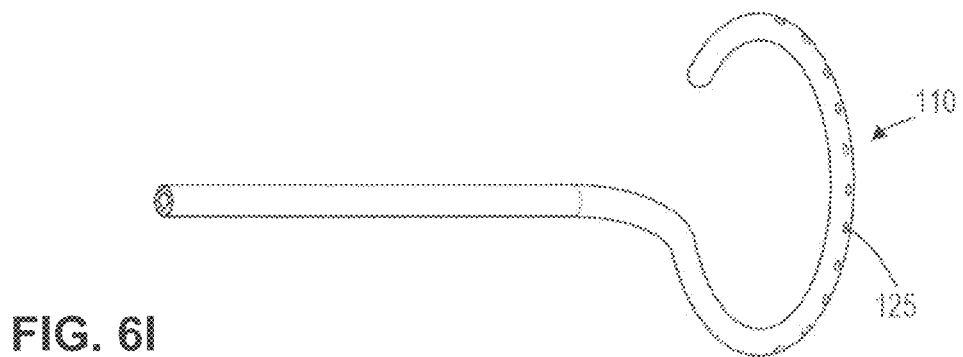
FIG. 6I is a schematic view of an articulating working end.

In another embodiment of FIG. 6H, the working end 110 has a heat applicator surface with at least one vapor outlet 125 and at least one expandable member 183 such as a balloon for positioning the heat applicator surface against targeted tissue. In another embodiment as shown in FIG. 6I, the working end can be a flexible material that is deflectable, for example, by a pull-wire. The embodiments of FIGS. 6H and 6I have configurations for use in treating various other medical indications, such as atrial fibrillation, for example in pulmonary vein ablation.

Figure 6J:
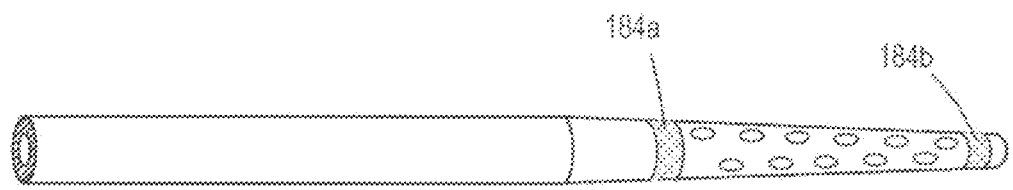
FIG. 6J is a schematic view of an alternative working end with RF electrodes.
Figure 6K:
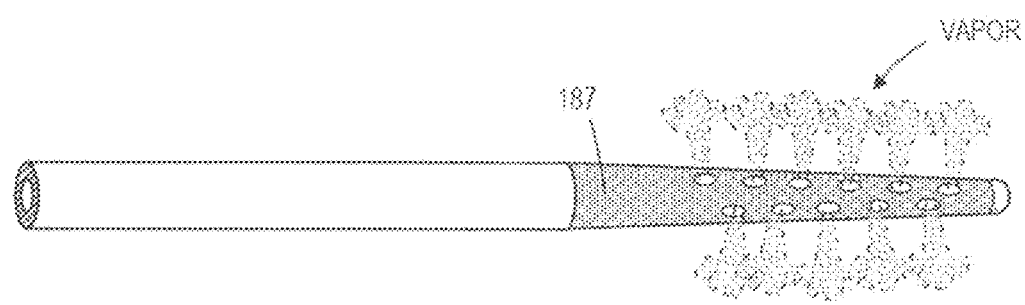
FIG. 6K is a schematic view of an alternative working end with a resistive heating element.
Figure 6L:
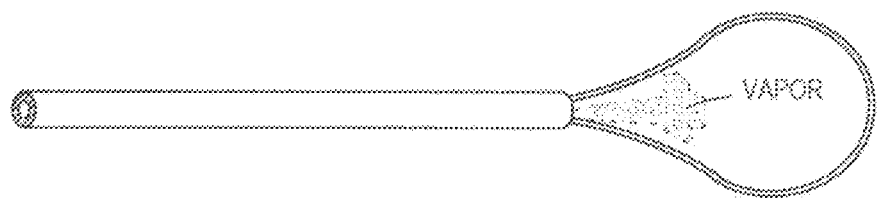
FIG. 6L is a schematic view of a working end with a tissue-capturing loop.
Figure 6M:
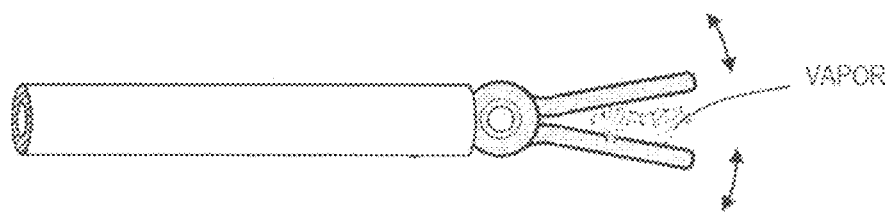
FIG. 6M is a schematic view of an alternative working end with jaws for capturing and delivering vapor to tissue.

In another embodiment of FIG. 6J, the working end 110 includes additional optional heat applicator means which can comprise a mono-polar electrode cooperating with a ground pad or bi-polar electrodes 184a and 184b for applying energy to tissue. In FIG. 6K, the working end 110 includes resistive heating element 187 for applying energy to tissue. FIG. 6L depicts a snare for capturing tissue to be treated with vapor and FIG. 6M illustrates a clamp or jaw structure. The working end 110 of FIG. 6M includes means actuatable from the handle for operating the jaws.

Sensors for Vapor Flows, Temperature, Pressure, Quality

Figure 7:
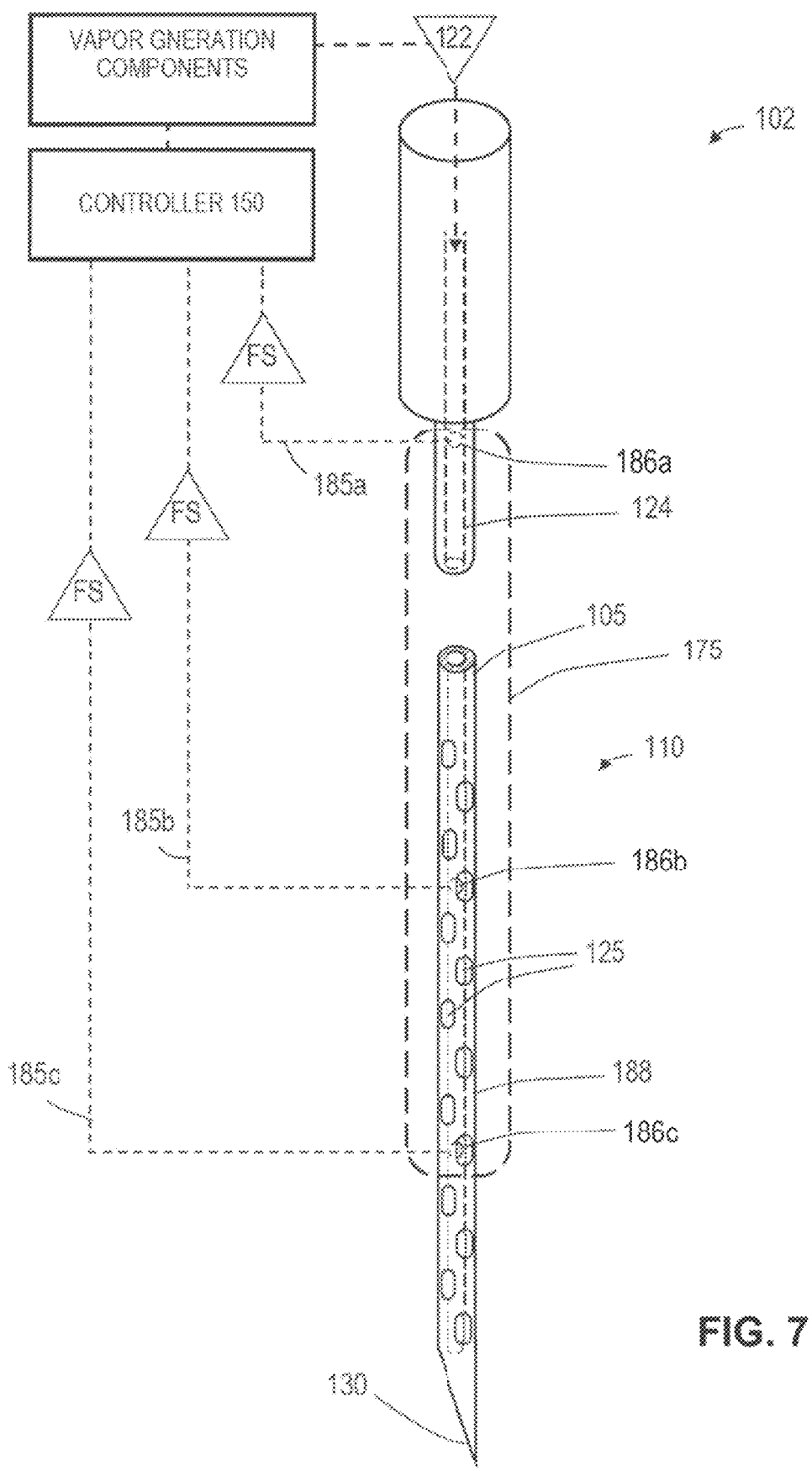
FIG. 7 is a schematic view of an alternative working end with jaws for capturing and delivering vapor to tissue.

Referring to FIG. 7, one embodiment of sensor system 175 is shown that is carried by working end 110 of the probe 102 depicted in FIG. 2 for determining a first vapor media flow parameter, which can consist of determining whether the vapor flow is in an "on" or "off" operating mode. The working end 110 of FIG. 7 comprises a sharp-tipped needle suited for needle ablation of any neoplasia or tumor tissue, such as a benign or malignant tumor as described previously, but can also be any other form of vapor delivery tool. The needle can be any suitable gauge and in one embodiment has a plurality of vapor outlets 125. In a typical treatment of targeted tissue, it is important to provide a sensor and feedback signal indicating whether there is a flow, or leakage, of vapor media 122 following treatment or in advance of treatment when the system is in "off" mode. Similarly, it is important to provide a feedback signal indicating a flow of vapor media 122 when the system is in "on" mode. In the embodiment of FIG. 7, the sensor comprises at least one thermocouple or other temperature sensor indicated at 185a, 185b and 185c that are coupled to leads (indicated schematically at 186a, 186b and 186c) for sending feedback signals to controller 150. The temperature sensor can be a singular component or can be plurality of components spaced apart over any selected portion of the probe and working end. In one embodiment, a feedback signal of any selected temperature from any thermocouple in the range of the heat of vaporization of treatment media 122 would indicate that flow of vapor media, or the lack of such a signal would indicate the lack of a flow of vapor media. The sensors can be spaced apart by at least 0.05 mm, 1 mm, 5 mm, 10 mm and 50 mm. In other embodiments, multiple temperature sensing events can be averaged over time, averaged between spaced apart sensors, the rate of change of temperatures can be measured and the like. In one embodiment, the leads 186a, 186b and 186c are carried in an insulative layer of wall 188 of the extension member 105. The insulative layer of wall 188 can include any suitable polymer or ceramic for providing thermal insulation. In one embodiment, the exterior of the working end also is also provided with a lubricious material such as Teflon® which further insures against any tissue sticking to the working end 110.

Still referring to FIG. 7, a sensor system 175 can provide a different type of feedback signal FS to indicate a flow rate or vapor media based on a plurality of temperature sensors spaced apart within flow channel 124. In one embodiment, the controller 150 includes algorithms capable of receiving feedback signals FS from at least first and second thermocouples (e.g., 185a and 185c) at very high data acquisition speeds and compares the difference in temperatures at the spaced apart locations. The measured temperature difference, when further combined with the time interval following the initiation of vapor media flows, can be compared against a library to thereby indicate the flow rate.

Figure 8:
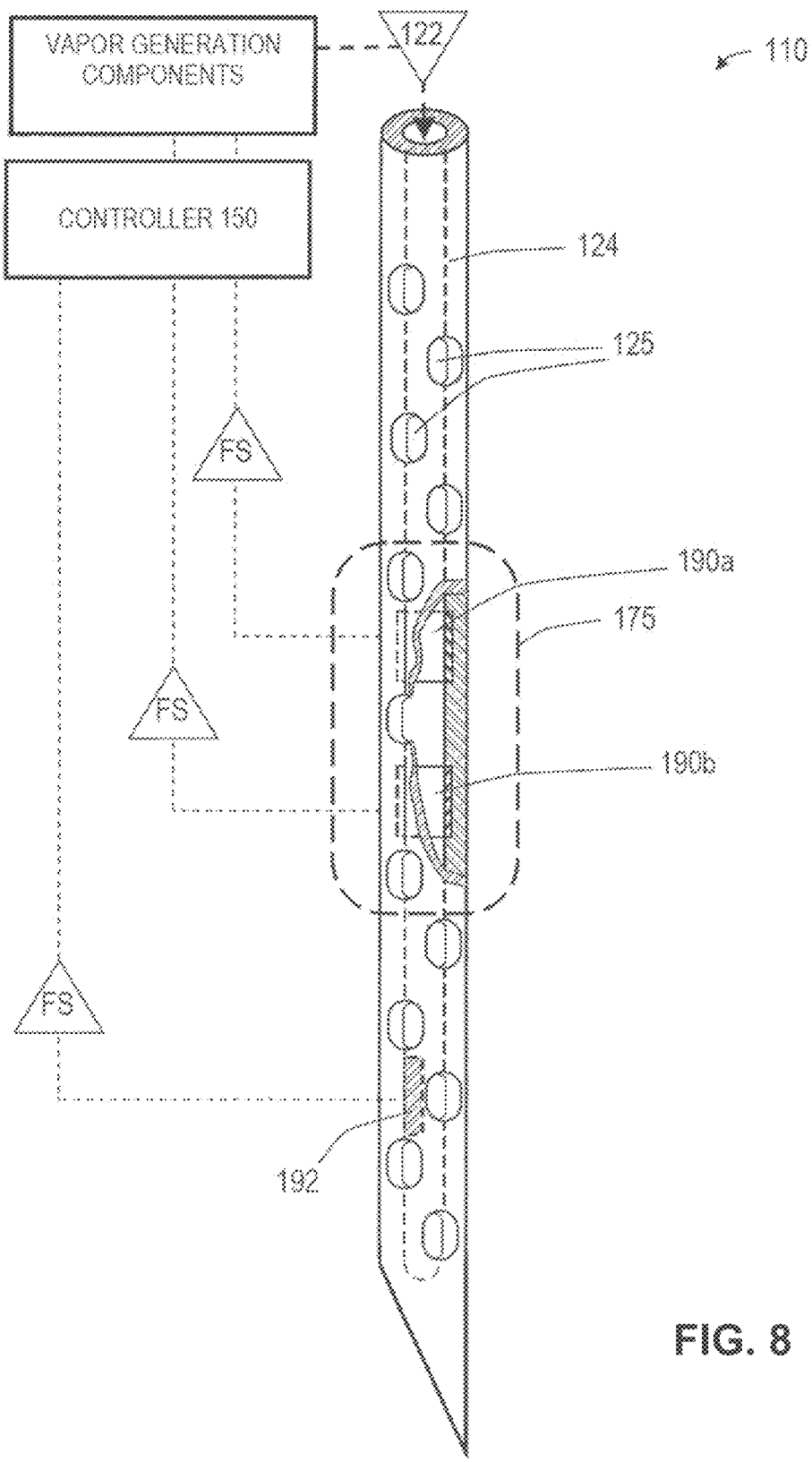
FIG. 8 is a schematic view of an alternative working end with jaws for capturing and delivering vapor to tissue.

Another embodiment of sensor system 175 in a similar working end 110 is depicted in FIG. 8, wherein the sensor is configured for indicating vapor quality—in this case based on a plurality of spaced apart electrodes 190a and 190b coupled to controller 150 and an electrical source (not shown). In this embodiment, a current flow is provided within a circuit to the spaced apart electrodes 190a and 190b and during vapor flows within channel 124 the impedance will vary depending on the vapor quality or saturation, which can be processed by algorithms in controller 150 and can be compared to a library of impedance levels, flow rates and the like to thereby determine vapor quality. It is important to have a sensor to provide feedback of vapor quality, which determines how much energy is being carried by a vapor flow. The term "vapor quality" is herein used to describe the percentage of the flow that is actually water vapor as opposed to water droplets that is not phase-changed. In another embodiment (not shown) an optical sensor can be used to determine vapor quality wherein a light emitter and receiver can determine vapor quality based on transmissibility or reflectance of a vapor flow.

Figure 1A:
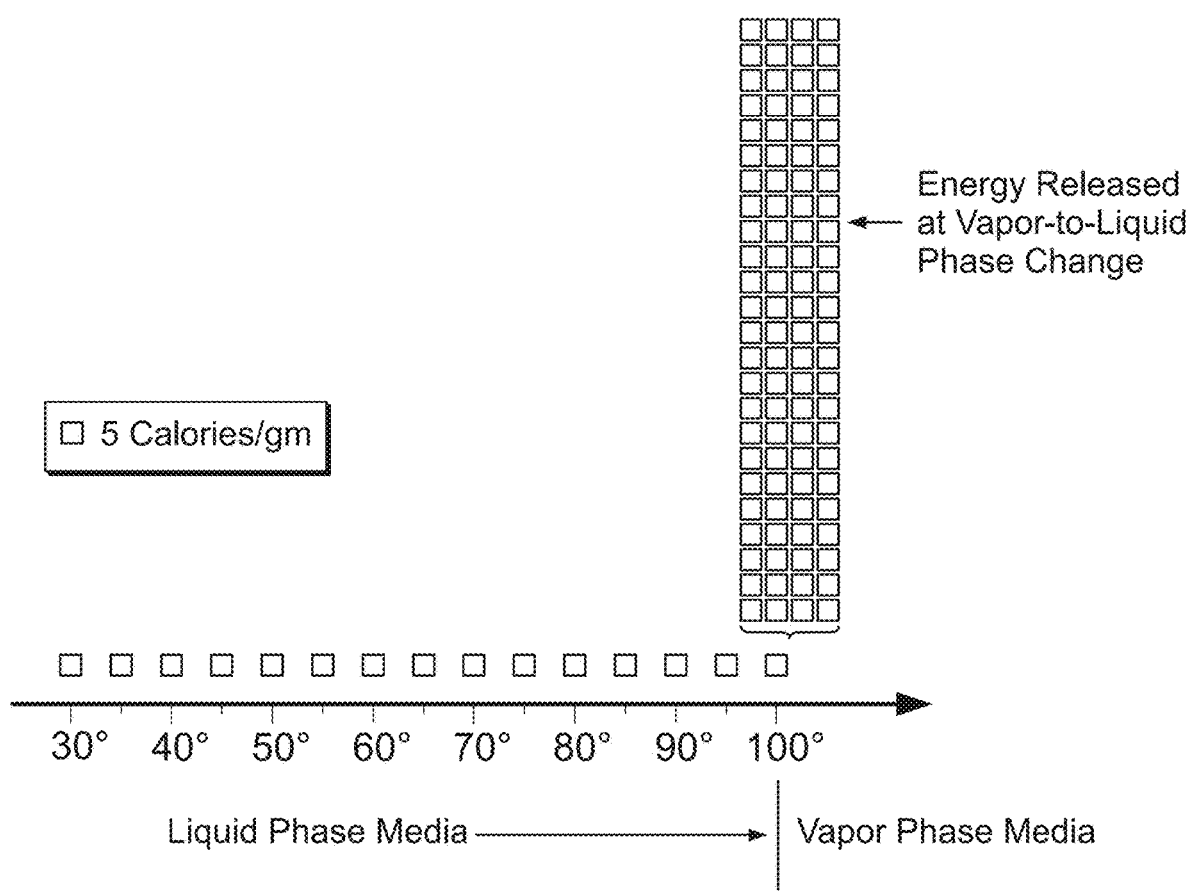
FIG. 1A is a graphical depiction of the quantity of energy needed to achieve the heat of vaporization of water.
Figure 1B:
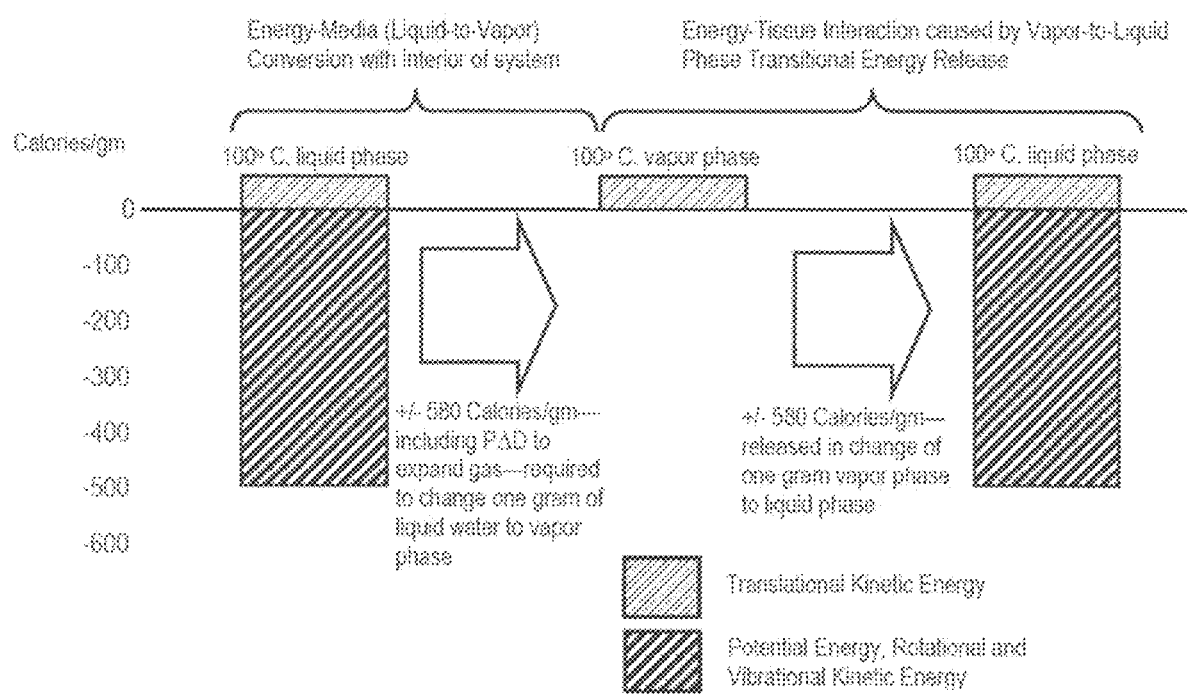
FIG. 1B is a diagram of phase change energy release that underlies a system and method of the devices and methods.

FIG. 8 further depicts a pressure sensor 192 in the working end 110 for providing a signal as to vapor pressure. In operation, the controller can receive the feedback signals FS relating to temperature, pressure and vapor quality to thereby modulate all other operating parameters described above to optimize flow parameters for a particular treatment of a target tissue, as depicted in FIG. 1. In one embodiment, a MEMS pressure transducer is used, which is known in the art. In another embodiment, a MEMS accelerometer coupled to a slightly translatable coating can be utilized to generate a signal of changes in flow rate, or a MEMS microphone can be used to compare against a library of acoustic vibrations to generate a signal of flow rates.

Inductive Vapor Generation Systems

Figure 9:
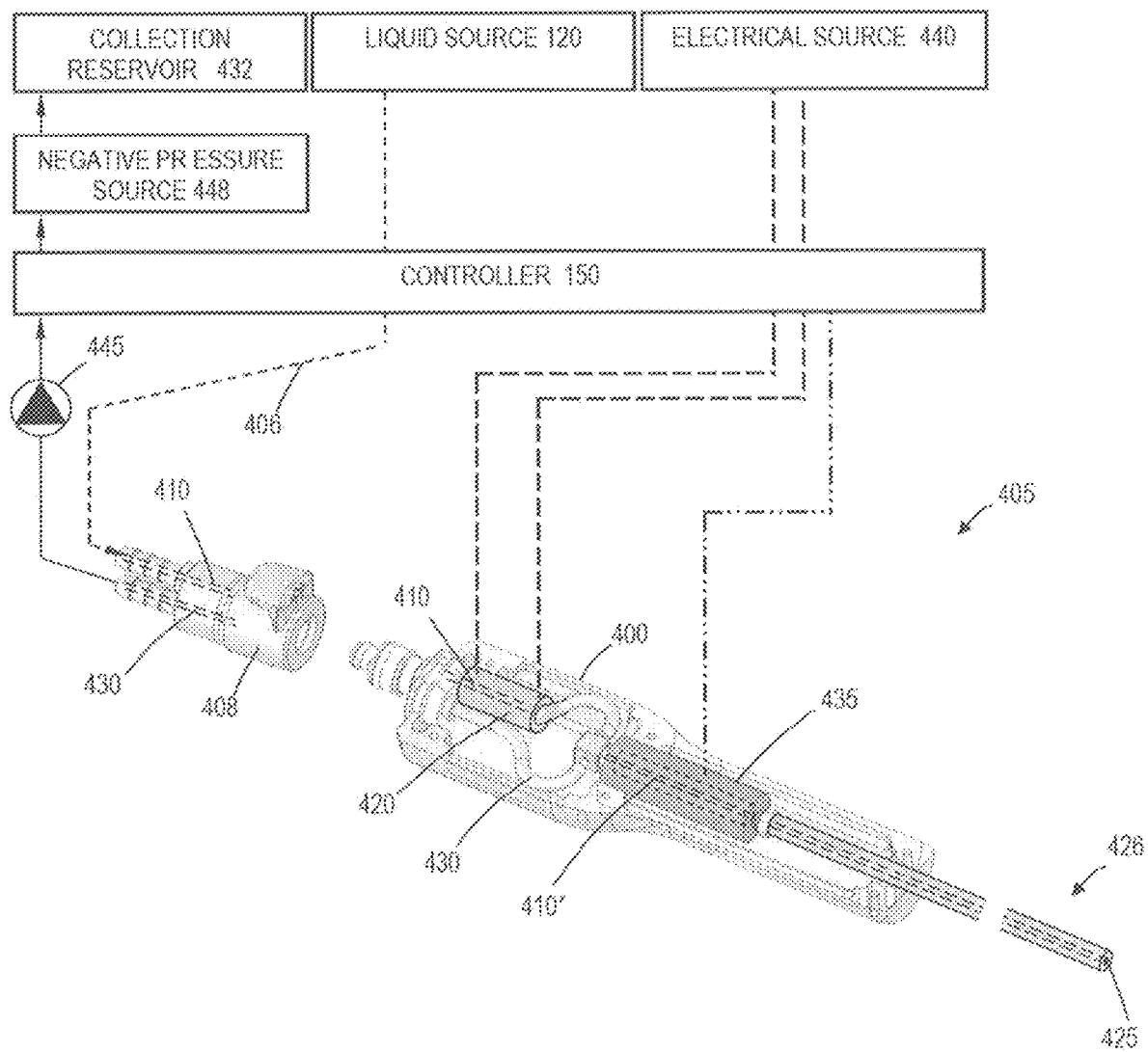
FIG. 9 is a partly disassembled view of a variation of a handle and variation of an inductive vapor generator system for use with devices and methods described herein.
Figure 10:
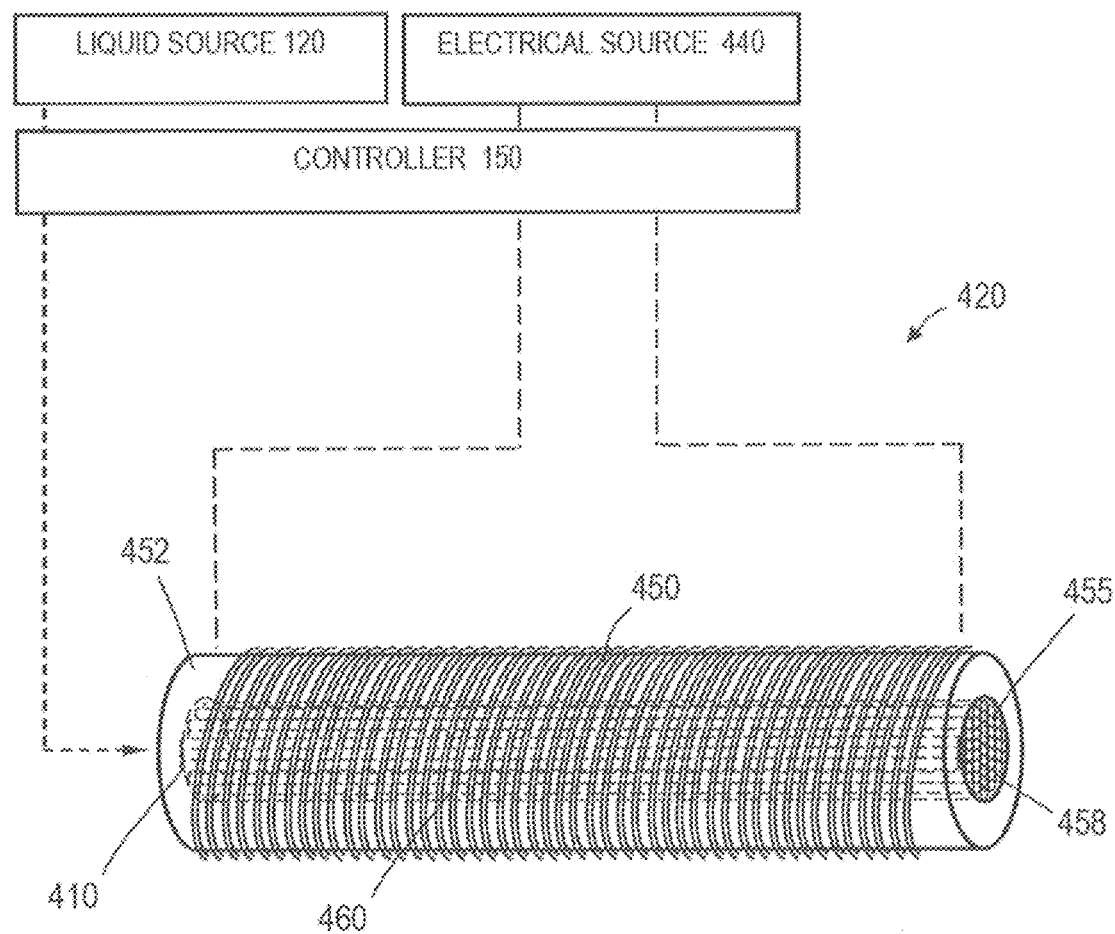
FIG. 10 is an enlarged schematic view of another variation of an inductive vapor generator of FIG. 9.

FIGS. 9 and 10 depict a vapor generation component that utilizes and an inductive heating system within a handle portion 400 of the probe or vapor delivery tool 405. In FIG. 9, it can be seen that a pressurized source of liquid media 120 (e.g., water or saline) is coupled by conduit 406 to a quick-connect fitting 408 to deliver liquid into a flow channel 410 extending through an inductive heater 420 in probe handle 400 to at least one outlet 425 in the working end 426. In one embodiment shown in FIG. 9, the flow channel 410 has a bypass or recirculation channel portion 430 in the handle or working end 426 that can direct vapor flows to a collection reservoir 432. In operation, a valve 435 in the flow channel 410 thus can direct vapor generated by inductive heater 420 to either flow channel portion 410' or the recirculation channel portion 430. In the embodiment of FIG. 10, the recirculation channel portion 430 also is a part of the quick-connect fitting 408.

In FIG. 9, it can be seen that the system includes a computer controller 150 that controls (i) the electromagnetic energy source 440 coupled to inductive heater 420, (ii) the valve 435 which can be an electrically-operated solenoid, (iii) an optional valve 445 in the recirculation channel 430 that can operate in unison with valve 435, and (iv) optional negative pressure source 448 operatively coupled to the e recirculation channel 430.

In general, one variation of a system can provide a small handheld device including an assembly that utilizes electromagnetic induction to turn a sterile water flow into superheated or dry vapor which can is propagated from at least one outlet in a vapor delivery tool to interface with tissue and thus ablate tissue. In one aspect, an electrically-conducting microchannel structure or other flow-permeable structure is provided and an inductive coil causes electric current flows in the structure. Eddies within the current create magnetic fields, and the magnetic fields oppose the change of the main field thus raising electrical resistance and resulting in instant heating of the microchannel or other flow-permeable structure. In another aspect, it has been found that corrosion-resistant microtubes of low magnetic 316 SS are suited for the application, or a sintered microchannel structure of similar material. While magnetic materials can improve the induction heating of a metal because of ferromagnetic hysteresis, such magnetic materials (e.g. carbon steel) are susceptible to corrosion and are not optimal for generating vapor used to ablate tissue. In certain embodiments, the electromagnetic energy source 440 is adapted for inductive heating of a microchannel structure with a frequency in the range of 50 kHz to 2 Mhz, and more preferably in the range of 400 kHz to 500 kHz. While a microchannel structure is described in more detail below, it should be appreciated that variations of the devices or methods can include flow-permeable conductive structures selected from the group of woven filaments structures, braided filament structures, knit filaments structures, metal wool structures, porous structures, honeycomb structure and an open cell structures.

In general, a method of treating tissue as described herein can include utilizing an inductive heater 420 of FIGS. 9-10 to instantly vaporize a treatment media such as deionized water that is injected into the heater at a flow rate of ranging from 0.001 to 20 ml/min, 0.010 to 10 ml/min, 0.050 to 5 ml/min., and to eject the resulting vapor into body structure to ablate tissue. The method further comprises providing an inductive heater 420 configured for a disposable had-held device (see FIG. 9) that is capable of generating a minimum water vapor that is at least 70% water vapor, 80% water vapor and 90% water vapor.

FIG. 10 is an enlarged schematic view of inductive heater 420 which includes at least one winding of inductive coil 450 wound about an insulative sleeve 452. The coil 450 is typically wound about a rigid insulative member, but also can comprise a plurality of rigid coil portions about a flexible insulator or a flexible coil about a flexible insulative sleeve. The coil can be in handle portion of a probe or in a working end of a probe such as a catheter. The inductive coil can extends in length at least 5 mm, 10 mm, 25 mm, 50 mm or 100 m.

In one embodiment shown schematically in FIG. 10, the inductive heater 420 has a flow channel 410 in the center of insulative sleeve 452 wherein the flows passes through an inductively heatable microchannel structure indicated at 455. The microchannel structure 455 comprises an assembly of metal hypotubes 458, for example consisting of thin-wall biocompatible stainless steel tube tightly packed in bore 460 of the assembly. The coil 450 can thereby inductively heat the metal walls of the microchannel structure 455 and the very large surface area of structure 455 in contact with the flow can instantly vaporize the flowable media pushed into the flow channel 410. In one embodiment, a ceramic insulative sleeve 452 has a length of 1.5" and outer diameter of 0.25" with a 0.104" diameter bore 460 therein. A total of thirty-two 316 stainless steel tubes 458 with 0.016" O.D., 0.010" I.D., and 0.003" wall are disposed in bore 460. The coil 450 has a length of 1.0" and comprises a single winding of 0.026" diameter tin-coated copper strand wire (optionally with ceramic or Teflon® insulation) and can be wound in a machined helical groove in the insulative sleeve 452. A 200W RF power source 440 is used operating at 400 kHz with a pure sine wave. A pressurized sterile water source 120 comprises a computer controlled syringe that provides fluid flows of deionized water at a rate of 3 ml/min which can be instantly vaporized by the inductive heater 420. At the vapor exit outlet or outlets 125 in a working end, it has been found that various pressures are needed for various tissues and body cavities for optimal ablations, ranging from about 0.1 to 20 psi for ablating body cavities or lumens and about 1 psi to 100 psi for interstitial ablations.

FIGS. 11A-11D schematically depict a catheter system 600 and method of use wherein the catheter is adapted for treating structure in the wall of body lumen, such as treating electrical disorders in various body tissue. For example such treatments can take place in a patient's heart or in or near nerves carried within or about the wall of a blood vessel. In one example, referring to FIG. 11A, the catheter system 600 can be configured for the treatment of chronic hypertension. Hypertension or high blood pressure can be a persistent condition in which a patient's systemic arterial blood pressure is abnormally high. Hypertension can be classified as either primary or secondary. About 90%-95% of cases are termed primary hypertension, which refers to an abnormally high blood pressure for which no medical cause can be found. The remaining 5% to 10% of secondary hypertension can be caused by a variety of other conditions that affect the kidneys, arteries, heart or endocrine system. Persistent hypertension is a major risk factor for stroke, heart attack and kidney failure. In the progression to later stage persistent hypertension, there is a noted excess activity of the renal nerves. The principal therapies for hypertension comprise oral and intravenous drugs that act directly or indirectly on the kidney, such as diuretics and angiotensin converting enzyme (ACE) inhibitors. Such drug therapies are most effective in the early stages of hypertension. In mid- to later stages of chronic hypertension, the drug treatments are not truly effective. Studies have shown that renal denervation can be used to control persistent hypertension which thus may slow the progression to later- or end-stage disease.

Figure 11A:
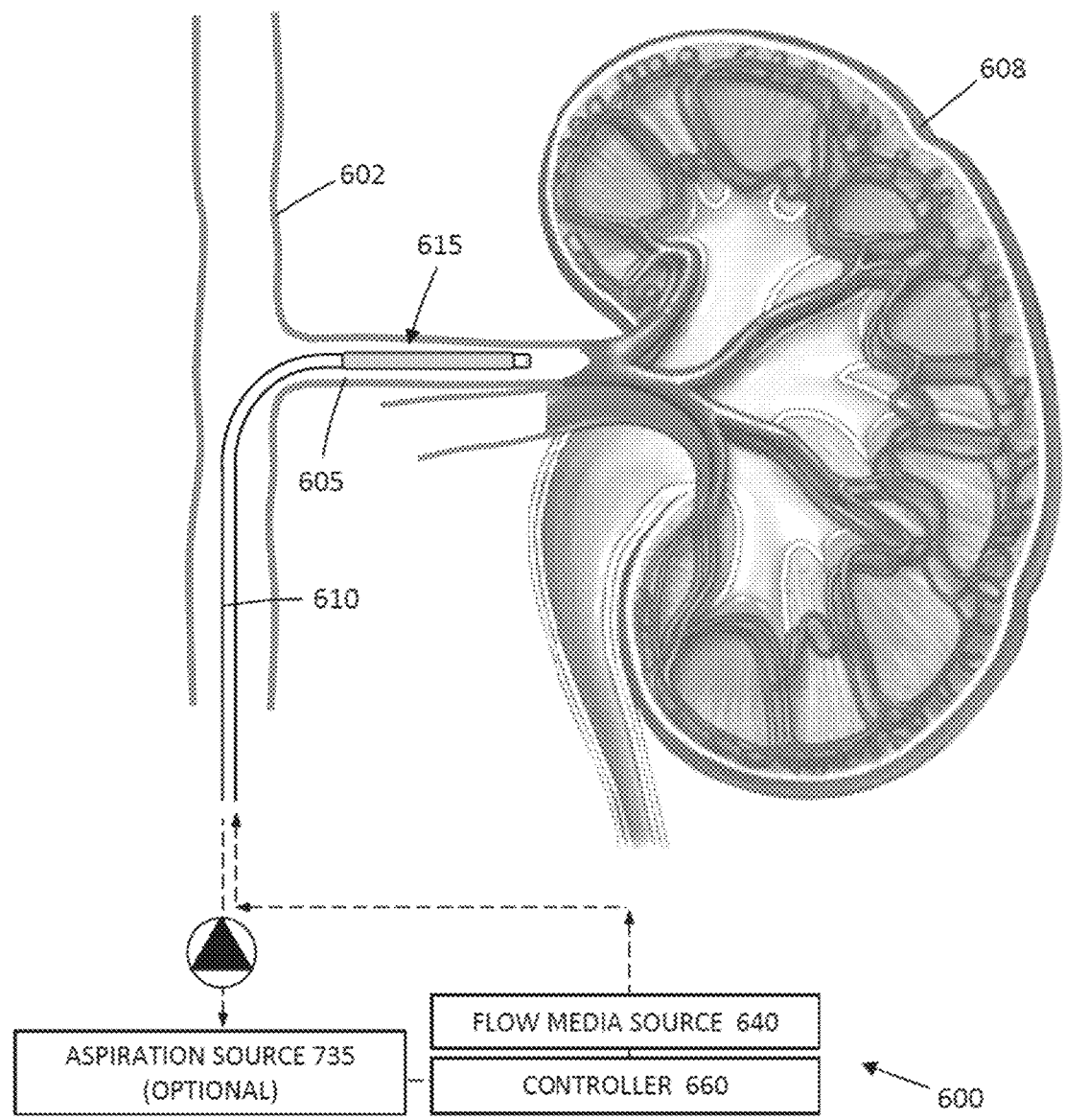
FIG. 11A is an illustration of a variation of a method where a working end of a catheter is introduced into the lumen of a renal artery for treatment of electrical signal transmission characteristics in nerve fibers in the artery.

The renal arteries normally extend from the side of the abdominal aorta 602 and carry a large portion of total blood flow to the kidneys (FIG. 11A). In FIG. 11A, it can be seen that renal artery 605 extends from aorta 602 to the kidney 608. Up to one third of total cardiac output can pass through the renal arteries for filtration by the kidneys. The arterial supply of the kidneys is somewhat variable. There may be one or more renal arteries supplying each kidney. Supernumerary renal arteries (two or more arteries to a single kidney) are the most common anomaly, with such occurrences ranging from 25% to 40%. The mean diameter of a renal artery is in the 5 mm range.

Figure 11B:
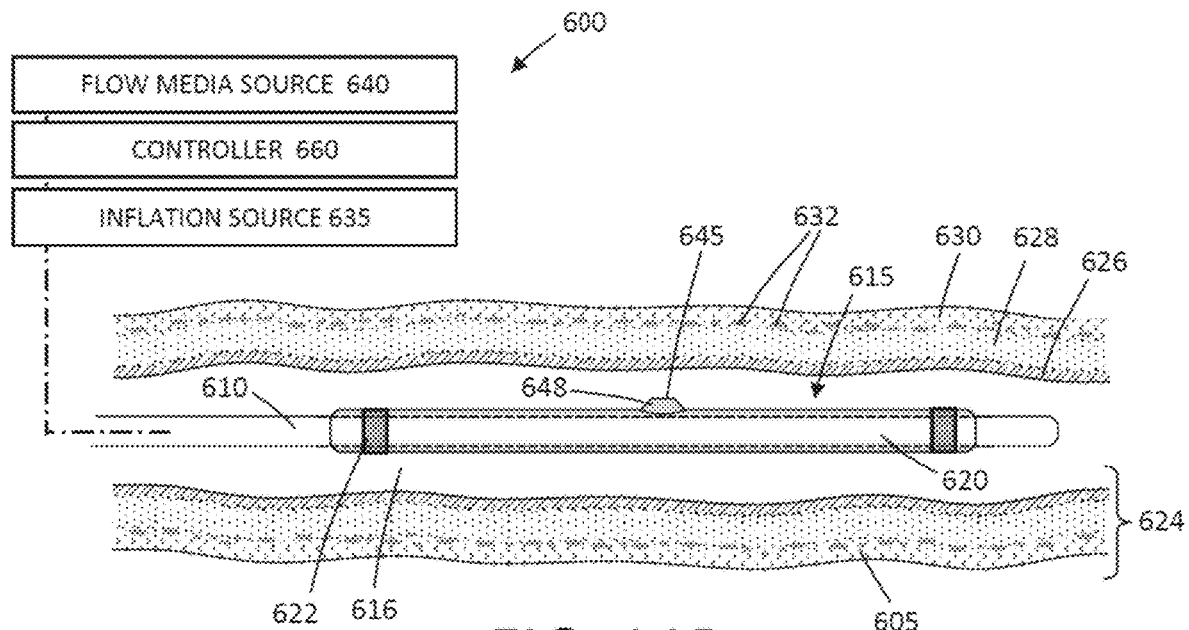
FIG. 11B illustrates an enlarged schematic view of the catheter working end of FIG. 11A.

FIGS. 11A-11B depict a process of modifying the electrical signal transmission characteristics in nerve fibers in an arterial wall wherein an elongated catheter shaft 610 with a working end 615 has been navigated into the lumen 616 of renal artery 605. A femoral artery access can be used as is known in the art. The catheter working end 615 carries an elongated expandable portion that can comprise a balloon 620. The balloon 620 in a collapsed position is configured for insertion and navigation through lumen 616 and can carry radiopaque markings 622, or that catheter shaft can have similar markings. The balloon can have a length ranging from about 1 cm to 40 cm with a diameter suited for engaging the wall 624 of the artery. The balloon can be compliant (distensible), non-compliant (non-distensible) or comprise a balloon that is slightly compliant under high inflation pressures as is known in the art. One type of balloon can have a wall of Nylon that is complaint at pressures ranging from 2 to 12 bar or more.

Now turning to FIG. 11B, an enlarged sectional view of renal artery 605 is shown, wherein the artery wall 624 is comprised of three layers: the internal intima 626, the muscular media 628 and the external fibrous adventitia 630. FIG. 11B further shows nerves 632 that extend along the length of the renal artery generally in and about the adventitia and the interface between the media 628 and adventitia 630 of the vessel wall. FIG. 11B illustrates the catheter working end 615 with the balloon 620 in a collapsed position.

Figure 11C:
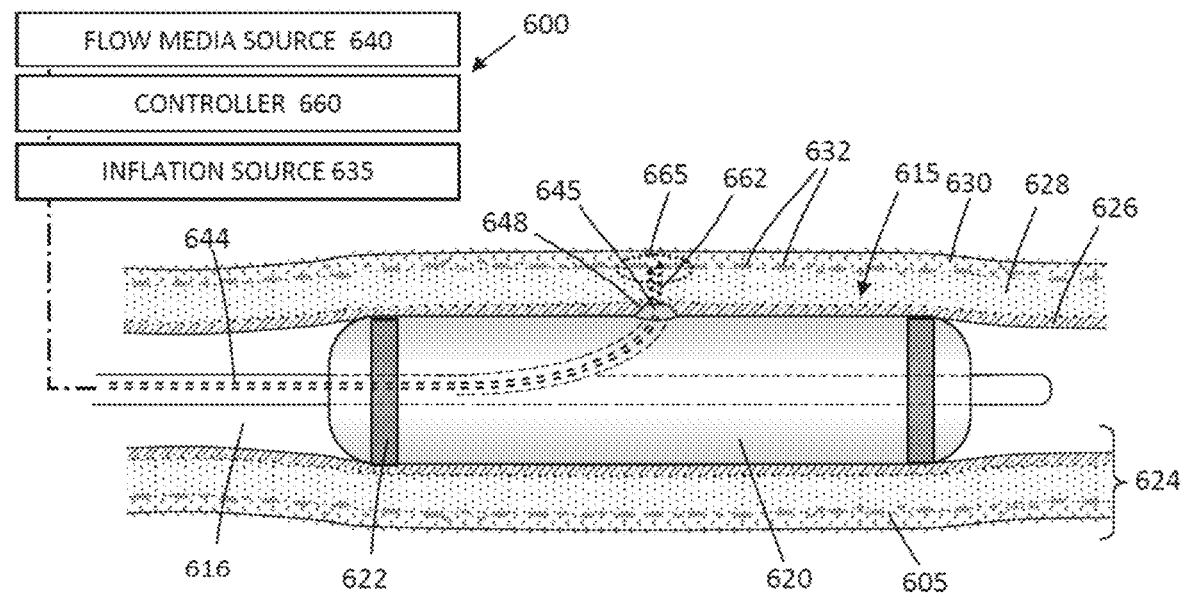
FIG. 11C illustrates the expansion of a balloon carried by the working end of FIG. 11B and the high pressure jetting of a flowable media from a jetting outlet into the arterial wall to cause damage to electrical signal carrying structures in the vessel wall.
Figure 12A:
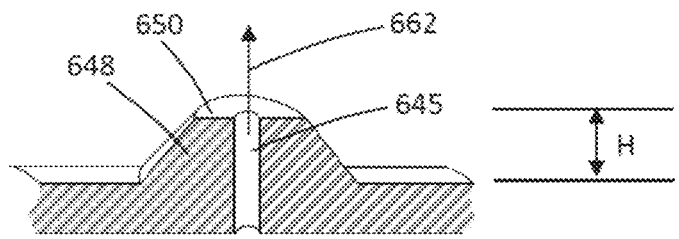
FIG. 12A is a magnified view of a portion of a catheter working end that shows a projecting feature that surrounds the jetting outlet.
Figure 12B:
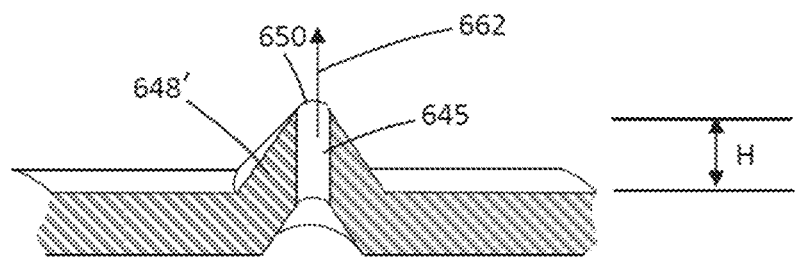
FIG. 12B is a magnified view of another projecting feature with a sharp apex that surrounds the jetting outlet in a catheter working end.
Figure 12C:
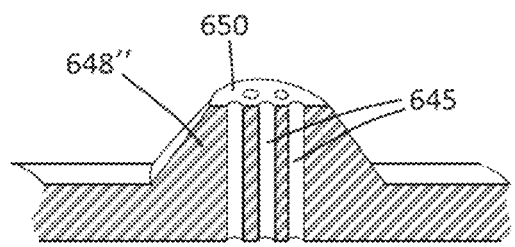
FIG. 12C is a magnified view of another projecting feature that surrounds a plurality of jetting outlets in a catheter working end.
Figure 12D:
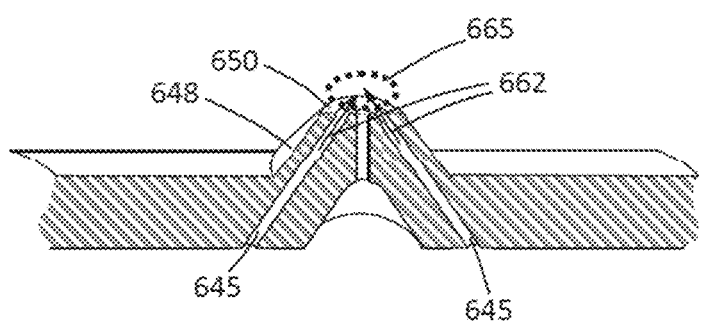
FIG. 12D is a magnified view of another projecting feature that surrounds jetting outlets that have converging axes.
Figure 12E:
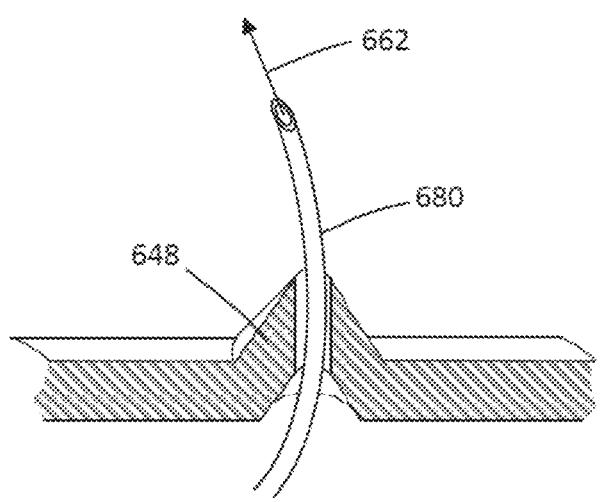
FIG. 12E is a magnified view of another working end wherein a micro-needle is extendable to penetrate a jetting outlet into the vessel wall.

FIG. 11C illustrates the working end 615 following actuation of the inflation source 635 and expansion of balloon 620 which is expanded to a diameter that engaged the arterial wall. As can be seen in FIG. 11C, a source of flow media 640 is operatively coupled to a handle end of the catheter (not shown) and flow channel 644 in the catheter shaft to provide a high pressure flow of flow media through a jet or microchannel flow outlet 645 in a radial outward portion of the expandable structure or balloon 620. In one embodiment shown in FIGS. 11B-11C, the microchannel outlet 645 can have a diameter ranging from about 0.0005" to 0.015" and can be carried in a projecting feature indicated at 648. The projecting feature 648 can comprise an element formed of plastic or metal and is configured for pressing into tissue of the vessel wall, with a radial or height dimension H of from 0.005" to 0.100". FIGS. 12A-12B depict the apex or surface 650 of exemplary projecting features 648 and 648' wherein the apex 650 can be flattened or relatively sharp about the flow outlet 645. FIG. 12C illustrates another embodiment with a plurality of microchannel outlets 645 in the projecting feature 648". FIG. 12D further depicts that microchannels 645 can be oriented with axes that converge so that flows 662 can converge with one another at a predetermined depth in tissue to further focus the delivery of mechanical energy on the targeted tissue site 665 in the vessel wall. In another working end embodiment schematically depicted in FIG. 12E, one or more hollow micro-needles 680 can be extended from the catheter to deliver the jetted flow media to the targeted tissue. A micro-needle with an angled tip can be rotated to jet flow media in slightly different orientations to expand the region of damaged tissue. In another embodiment, a solid wire microneedle can be penetrated into tissue and the flow media can then follow the path dissected by the needle penetration. Such a needle can also be rotated and a feature at the needle tip can be configured to damage or cut nerve tissue. The source of flow media 640 can use any type of high pressure pump known in the art of water jet systems, such as piston pumps, peristaltic pumps and the like.

FIG. 11C further illustrates the method of using the working end 615 to damage or alter electrical conduction in structures in the vessel wall, wherein the source of flow media 640 and controller 660 are actuated to cause a high pressure flow of flow media indicated at 662 into the vessel wall. In one embodiment, the flow media is saline or sterile water and the flow 662 can comprise one or more pulses at a pressure sufficient to mechanically cut tissue of the vessel wall and further cut and/or damage nerve fibers 632 in treatment region 665 of the vessel wall to thereby alter electrical signal transmission or transduction.

Figure 11D:
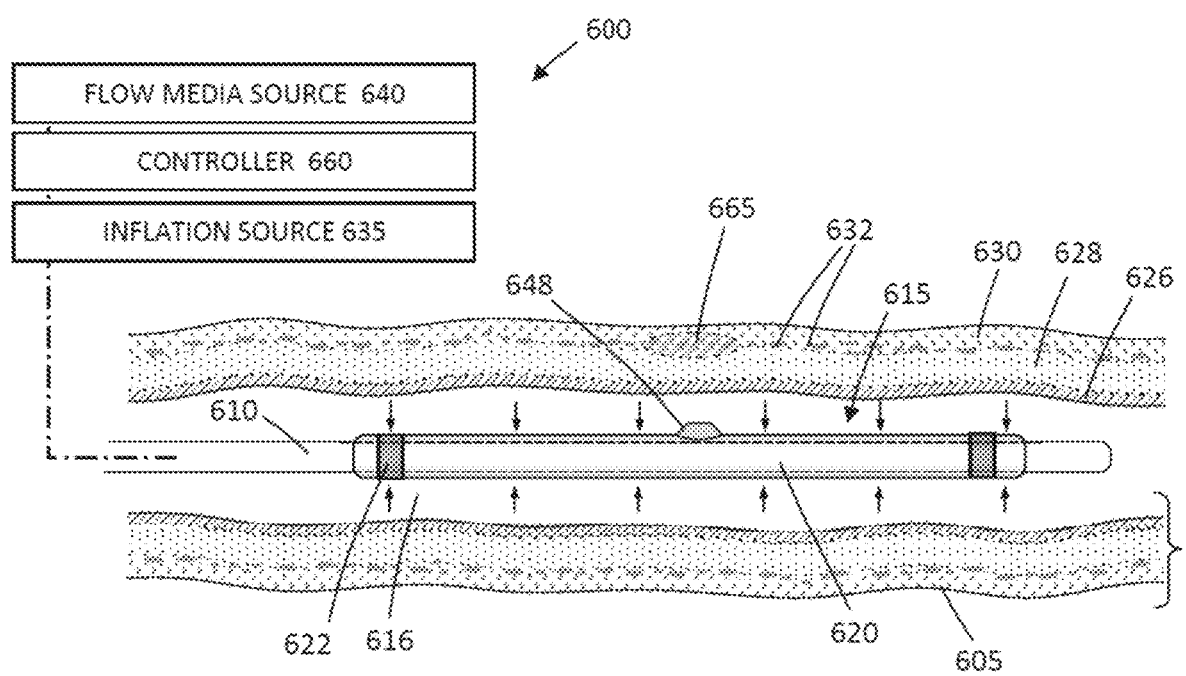
FIG. 11D illustrates a subsequent step of deflating the balloon following the termination of flow media delivery to thereby provide a treated region.

FIG. 11D illustrates a subsequent step of the method wherein the balloon 620 is collapsed and further depicts the treatment region 665 wherein signal transduction or transmission is altered, diminished or terminated. In the method illustrated in FIGS. 11A-11D, the flow media can have an ambient temperature, or can be a cryofluid or a heated liquid. The pressure require for tissue cutting can range from 100 psi to 20,000 psi. In one embodiment, such high pressure pulses can be provided by a circulating flow that is interrupted by a flow control valve as will be described further below in FIGS. 15A-15B. The volume of the pulse of flow media can be controlled by this means, as well as the pressure, to provide a flow that delivers mechanical energy to a predetermined depth in tissue before the mechanical energy is dissipated, wherein the predetermined depth of targeted site 665 can range from 0.1 mm to 2.0. The volume of flow media per pulse of the flow 662 can range from 10 to 100 microliters, and a treatment can consist of 1 to 20 pulses as depicted in FIGS. 11C and 12A-12D.

In another method, similar to that of FIG. 11C, the flow media can comprise or include a water vapor component which can undergo a phase change in or about the targeted site 665 to thereby apply thermal energy to the targeted site as well as mechanical energy to alter the electrical signaling capability of nerve fibers 632 in the vessel wall. In general, such vapor media can be generated and delivered as described in previous embodiments above.

Still referring to FIG. 11C, it can be understood that the working end 615 can be re-positioned in the lumen 616 in an artery 605 to apply energy in a plurality of treatment sites. For example, FIGS. 13A-13C illustrate various patterns of treatment sites that can be discrete and spaced apart or can be overlapping to provide elongated linear, annular, or spiraling regions in which electrical transmission or transduction in nerve fibers is altered. Clearly, any variation or combination of patterns is within the scope of this disclosure.

Figure 14A:
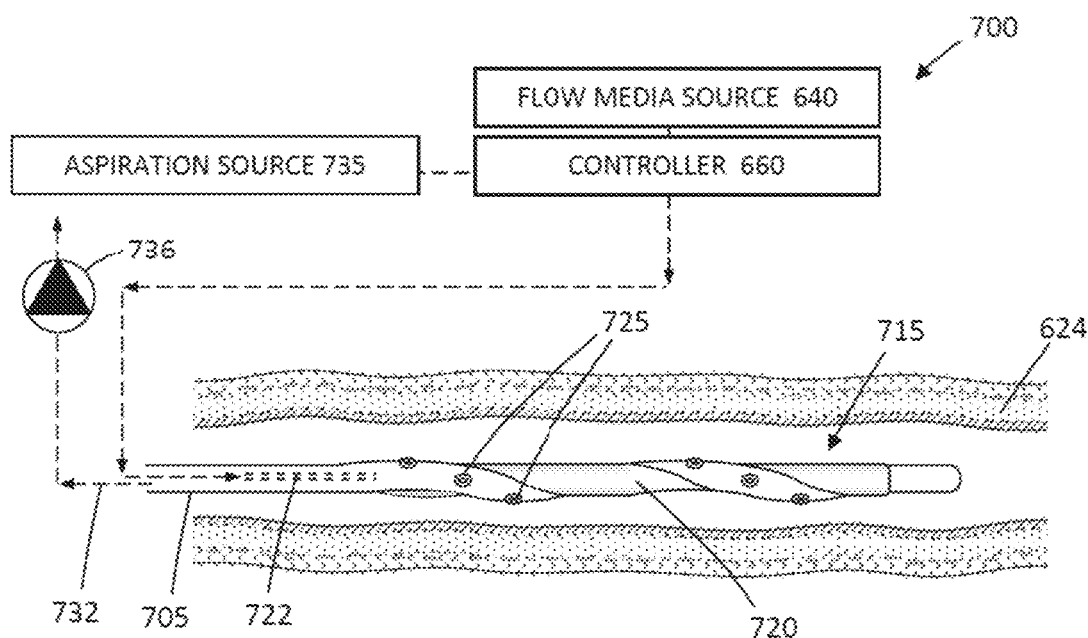
FIG. 14A illustrates another catheter working end and method of use wherein the working end has a spiral configuration following expansion by an expansion member.
Figure 14B:
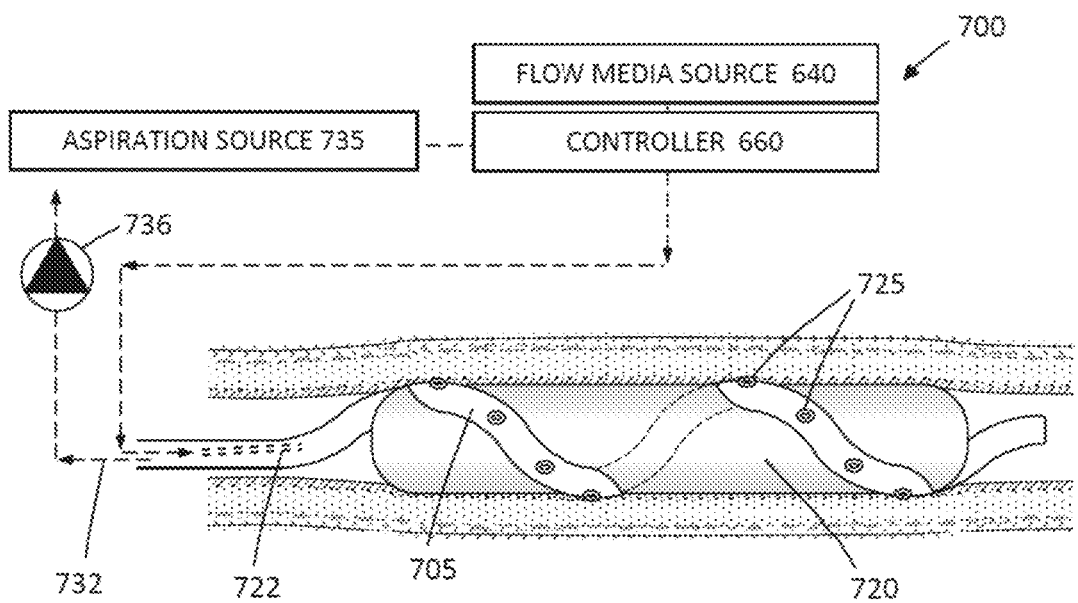
FIG. 14B illustrates the catheter working end of FIG. 14A in an expanded configuration to thereby treat tissue in a spiral pattern.

FIG. 13A depicts two partly annular treatment regions 665a and 665b that can be created by a plurality of closely spaced jetting outlets 645 in the catheter to provide each continuous treatment region (see FIG. 14B). FIG. 13B shows a continuous treatment zone 665c which spirals about the vessel. FIG. 13C illustrates four discrete, spaced apart treatment regions 665d-665g that in one method are radially spaced apart at 90o. The scope of the method thus can comprise any annular, partly annular, spiraling, partly spiraling, localized or spaced apart regions or any combination thereof. In one method, a plurality of treatment regions are spaced apart and non-continuous yet extend from 180o to 360o around the vessel within the length of the renal artery.

In the methods described above, as practiced with the working end 615 of FIGS. 11A-11D, the intima 626 is substantially protected from mechanical or thermal damage by providing the high pressure jetted flow 662 of flow media through the intima to thus provide energy delivery to the interior portions of the vessel wall. This is advantageous over other thermal ablation systems that heat substantial regions of the intima 626 in order to cause passive heat conduction to the nerve fibers or to cause ohmic heating of the nerve fibers. In any embodiment that utilizes a balloon or balloons for engaging the wall of the lumen, the expansion media for the balloon can comprise a cooled gas or liquid, either static or recirculating to cool the vessel wall.

In another embodiment, the flow media can comprise or carry pharmacological agents or ablating fluids, such as BOTOX, alcohol, sclerosing agents, anesthetics and the like, for causing damage to the nerve fibers 632 in the vessel wall.

In FIGS. 11A-11D, the catheter shaft 605 is shown without a guidewire lumen but it should be appreciated that the catheter can have at least one other lumen for a guidewire or for blood perfusion, all of which are not shown for convenience only.

Now turning to FIGS. 14A-14B, another embodiment of catheter system 700 is shown with a catheter body 705 extending to working end 715. In one embodiment, the catheter body 705 is configured to spiral about an expansion balloon 720. In the expanded condition as depicted in FIG. 14B, it can be seen that the expanded balloon 720 will press the catheter body wall into contact with the vessel wall 624. In the embodiment of FIGS. 14A-14B, the high pressure source of flow media again is coupled to lumen 722 in the catheter body 705 that communicates with a plurality of jets or outlets 725 in the working end 715. The plurality of outlets 725 can have optionally can have projecting features 648 about each outlet 725 as described in the embodiment of FIGS. 11A-11D. The outlets 725 can be spaced apart from about 0.020" to 0.2". Thus, it can be understood that using the working end 715 as depicted in FIG. 14B will create a plurality of treatment region 665 as described previously in a spiral around the vessel, wherein the spiral pattern can comprise spaced apart treatment regions 665, close adjacent treatment regions or overlapping treatment regions to thus provide non-continuous or continuous damage to the nerve fibers around the circumference of the vessel. The method can further consist of delivering high pressure jets of flow media to cause mechanical damage in the targeted tissue or thermal energy provided by a vapor media, or a combination of both mechanical energy and thermal effects.

Figure 15A:
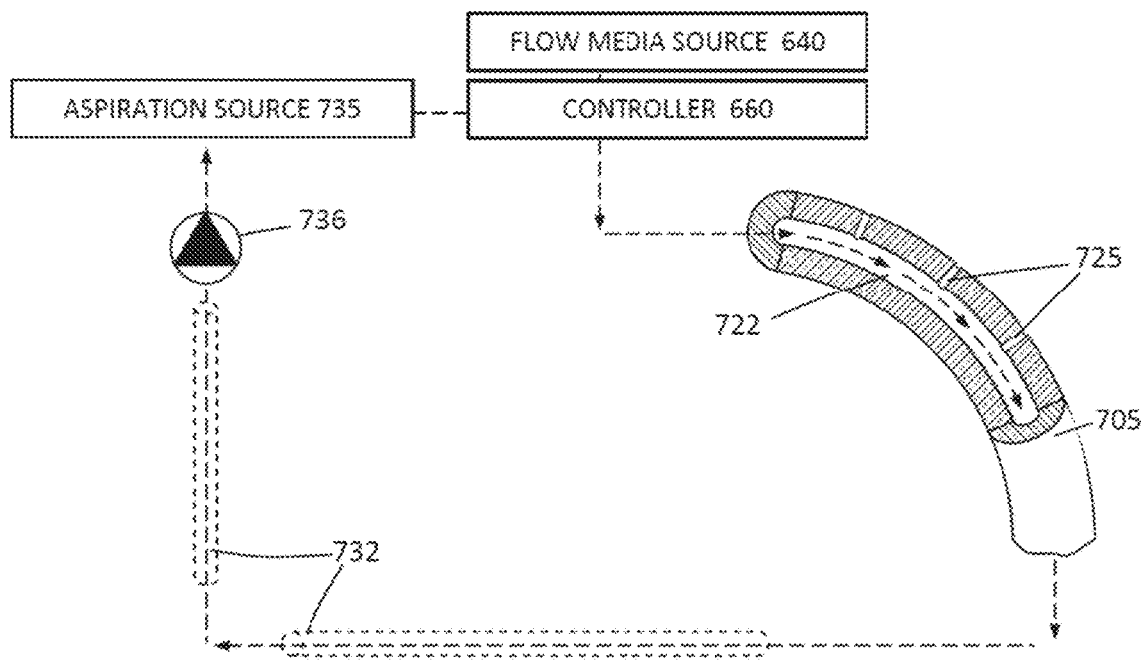
FIG. 15A is a schematic illustration and block diagram relating to the catheter system of FIGS. 14A-14B wherein the catheter system has flow media inflow and outflow lumens for a circulating flow together with a valve system for creating high pressure flow media jetting from a plurality of jetting outlets.
Figure 15B:
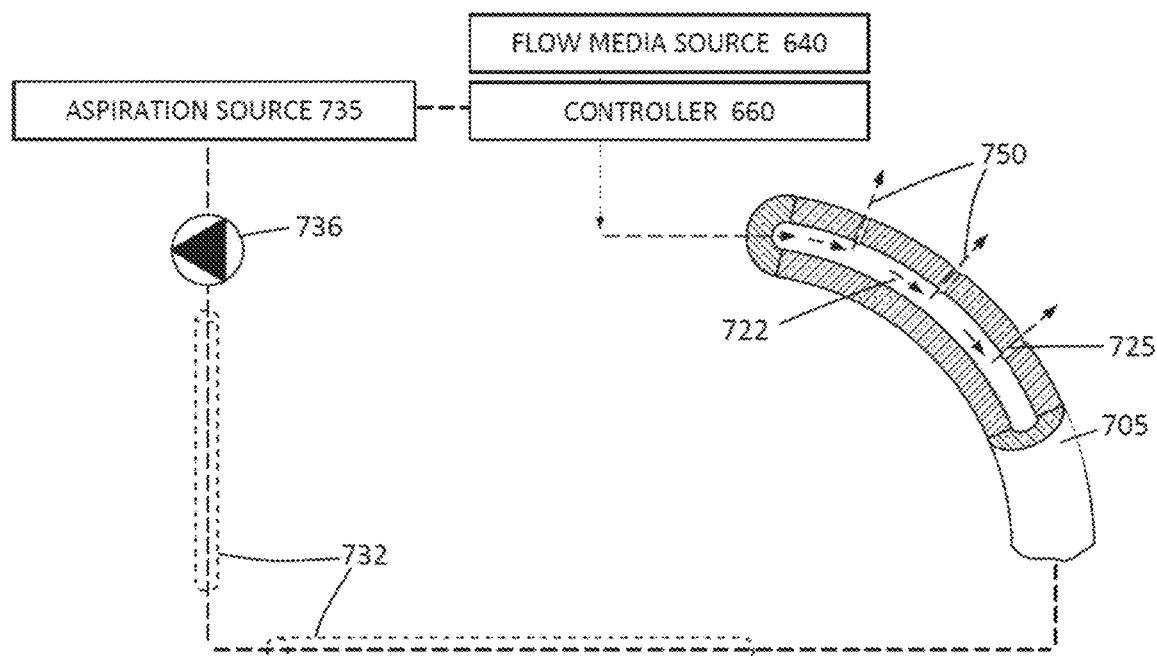
FIG. 15B is an illustration and block diagram similar to that of FIG. 15A wherein the valve system is actuated to cause high pressure flow media to jet outwardly from the plurality of jetting outlets.

FIGS. 15A-15B schematically depict another aspect of the catheter system 700 of FIGS. 14A-14B that is adapted to deliver high pressure pulses of a flow media, and is based on providing continuous circulating flow of a flow media (liquid or vapor) through the system. Related flow media circulation systems are disclosed in Application No. 61/126,647 filed on May 6, 2008; Application No. 61/126,651 filed on May 6, 2008; Application No. 61/126,612 Filed on May 6, 2008; Application No. 61/126,636 filed on May 6, 2008; Application No. 61/130,345 filed on May 31, 2008 and Application No. 61/191,459 filed on Sep. 9, 2008 each incorporated by reference. As can be seen in FIGS. 14B and 15A, the flow media source 640 can be actuated to provide a continuous flow of flow media through a lumen 722 in the portion of catheter body 705 that engages the vessel wall (not shown) upon expansion of a balloon or other expandable member. FIGS. 15A-15B show only a small portion of catheter body 705 that is configured with outlets 725. The flow media within inflow channel 722 flows through the working end 715 and then reverses flow outwardly (proximally) in return lumen 732. The return lumen 732 is within the catheter shaft 705 and is only shown schematically in FIGS. 15A-15B and can be understood to be in shaft 705 in FIGS. 14A-14B. The plurality of lumens can be parallel in the catheter body or concentric. The flow in the return lumen 732 optionally can be assisted by a negative pressure source 735 fluidly coupled to the return lumen and a collection reservoir (not shown). The negative pressure source also can be operated by controller 660. A solenoid valve 736 in the return line 732 is provided and can be left in the open position as depicted in FIG. 15A to thus provide a continuous flow of flow media thru the system. The cross section of microchannel outlets 725 is substantially small which thus prevents any significant flow through the outlets when the return lumen is open. FIG. 15B depicts the actuation of valve 736 to a closed position for an interval that may range from 0.01 second to 5 seconds or more which terminates the return flow and causes a pulse of treatment flows 750 from the outlets 725. The controller 660 can control the flow rate through the system, and then control the closing of valve 736 to generate the desired depth of mechanical damage caused by a liquid flow media. The same flow system can be used for delivering a vapor media to cause thermal effects in tissue, or combination of mechanical and thermal effects.

Figure 16:
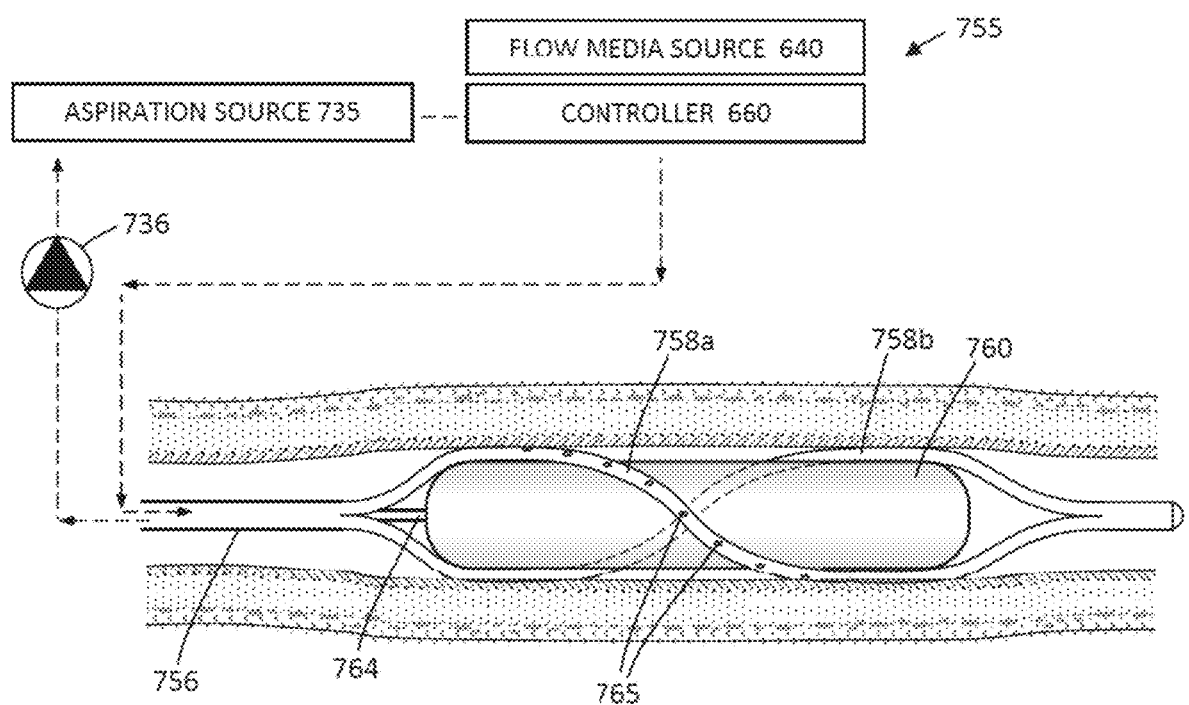
FIG. 16 is an illustration and block diagram of another catheter working end with first and second catheter sleeve portions that can be expanded apart by a balloon; the working end configured with a plurality of flow media jetting outlets.

FIG. 16 is an illustration of another embodiment of catheter system 755 which includes a catheter body 756 that diverges into a plurality of body portions 758a and 758b that can spiral about expansion balloon 760 or the body portions can be longitudinal relative to the balloon 760. A balloon inflation lumen is provided in catheter body portion 764. In this embodiment, the flow media outlets 765 are again disposed about the radially-outward surfaces of the catheter body portions 758a and 758b and can function as described in the embodiment of FIGS. 14A-14B. Again, the method of use consists of delivering high pressure jets of flow media to cause mechanical damage in the targeted tissue or thermal energy provided by a heated liquid or vapor media, or a combination of both mechanical energy and thermal effects. It should be appreciated that the catheter body portions 758a and 758b also could be moved to the expanded positions by a central pull-wire that would articulate the catheter body portions outwardly. Further, in any embodiment, the catheter body portion can range from two to six or more.

Figure 17:
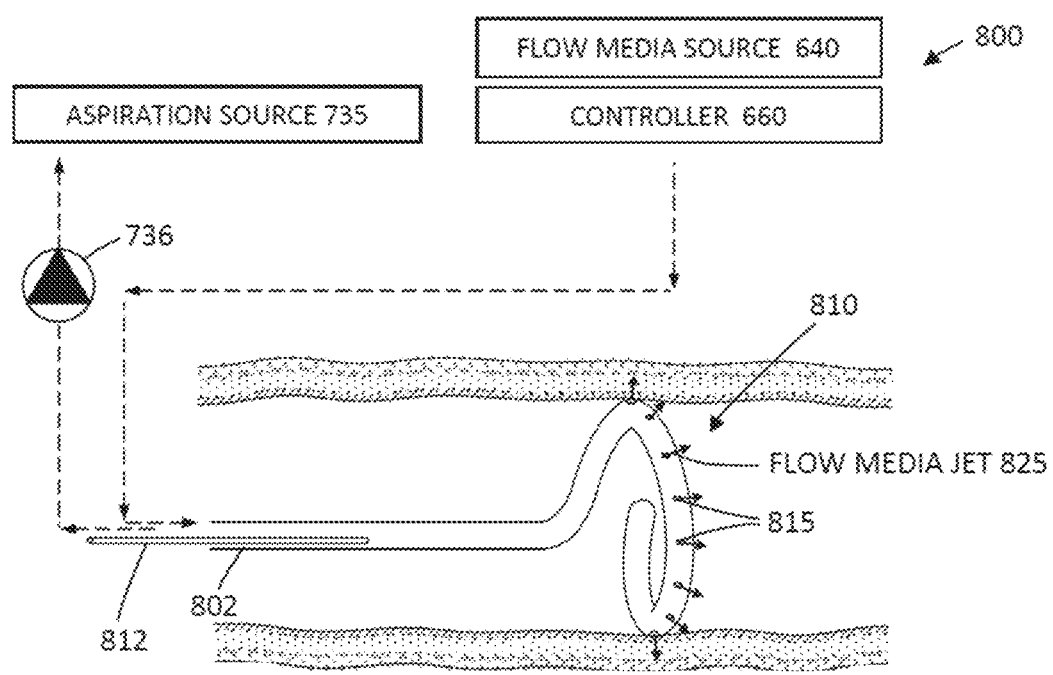
FIG. 17 is an illustration and block diagram of another catheter working end that can be articulated into an expanded cross section with a pull wire to engage the vessel wall; the working end configured with a plurality of flow media jetting outlets.

FIG. 17 illustrates another embodiment of catheter system 800 which includes a catheter body 802 that extends to an articulating working end 810 that is configured to engage the vessel wall without a balloon as in several previous embodiments. The working end 810 can be articulated by an interior pull wire 812. In this embodiment, the flow media outlets 815 again disposed in the radially-outward surface of the catheter working end when in the expanded position. As described previously, the method of use consists of delivering high pressure jets of flow media 825 to cause mechanical damage in the targeted tissue or thermal effects from vapor media, or a combination of both mechanical energy and thermal effects. It should be appreciated that the embodiment of FIG. 17 can include articulating the working end 810 to provide a substantially annular treatment region (or pattern) or a spiral treatment region of any suitable geometry.

Figure 18:
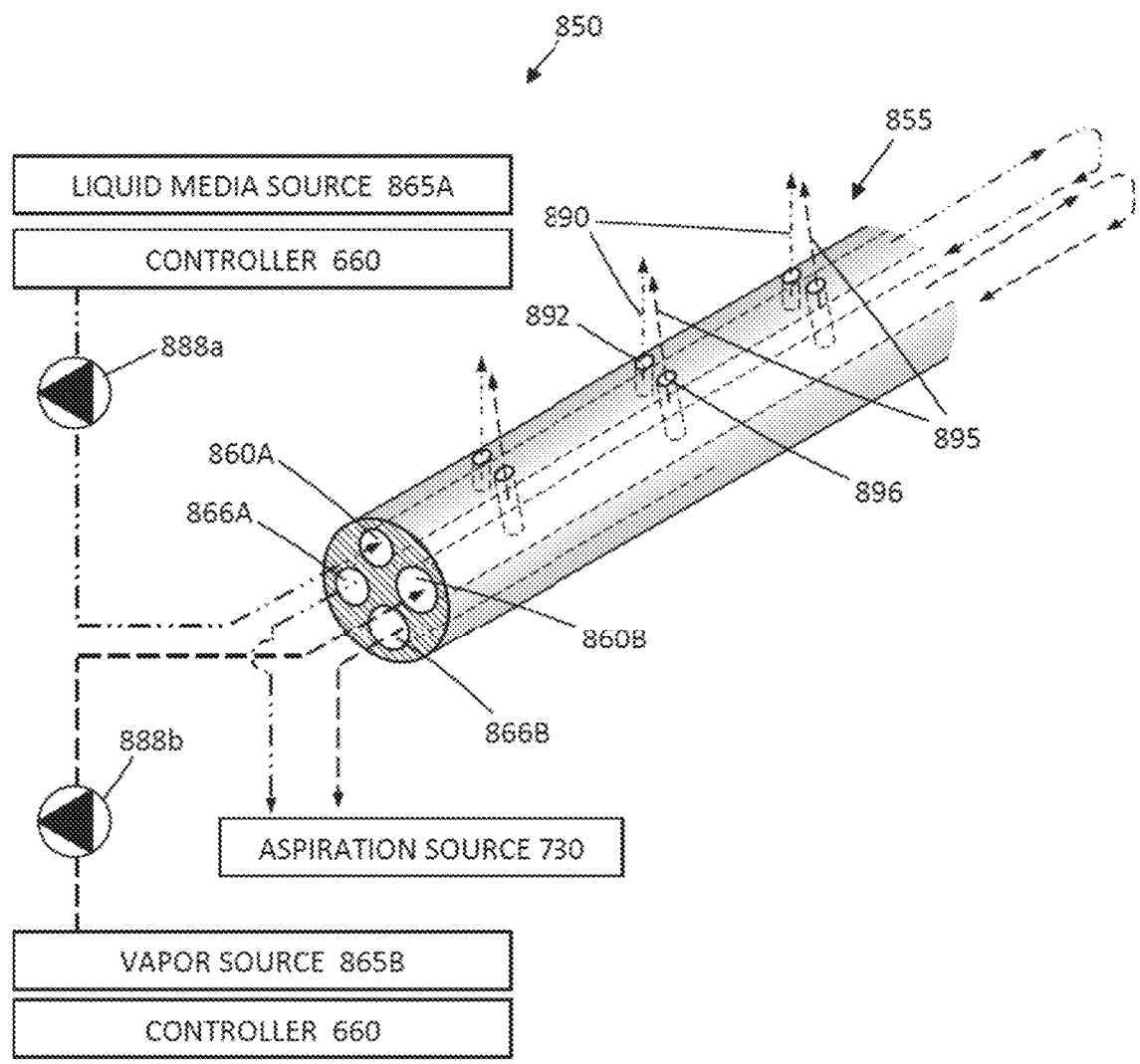
FIG. 18 is an illustration and block diagram of another catheter working end that include first and second flow media source and first and second inflow pathway for providing contemporaneous or sequential jetting of liquid cutting jets and vapor jets from separate outlets.

FIG. 18 illustrates another embodiment of catheter system 850, and more particularly a portion of catheter working end 855 that includes first and second media inflow channels 860A and 860B that are coupled to independent pressurized sources of flow media. A first source 865A comprises a water jet liquid media source, for example that is configured to jet saline or another liquid at high pressure to cut tissue and thereby cause mechanical damage to tissue. The second flow source 865B comprises a source of water vapor that is adapted for causing thermal effects in tissue. A first return flow channel 866A is distally coupled to the first inflow channel 860A to allow a recirculating flow as described previously with valve 888a configured to provide high pressure liquid media jets 890 being ejected from a plurality of outlets 892. A second return flow channel 886B is distally coupled to second inflow channel 860B to again allow a recirculating flow which is controlled by valve 888b in the manner described above. FIG. 18 shows high pressure vapor jets 895 being propagated from outlets 896 to cause thermal effects in the targeted tissue. In one embodiment, the liquid cutting jets 890 and vapor jets 895 can be pulsed alternatively or pulsed contemporaneously to delivery vapor the targeted region of the adventitia to damage nerve fibers therein. In one aspect of the method, the liquid cutting jet provides a dissected path to thereby permit vapor to propagate more effectively to the region of the nerve fibers and to allow greater vapor condensation and energy delivery in the targeted region. The controller 660 and negative pressure source 735 can operate as described previously. It should be appreciated that the first and second media inflow channels 860A and 860B can intersect proximal to a single outlet to thus provide a single outlet and pathway for intermittent pulses of liquid and vapor jets. In this embodiment, a single outflow channel could be optionally be used along with a valve system to control the first and second media flows in the catheter. Such single or multiple inflow channels that intersect also can be used to mix flowable media to control the temperature of the ejected flow with a cooled gas or liquid, to add substances such as pharmacological agents or abrasives to the flow or the like.

In general, another variation of a method for modifying structure in a targeted wall of a lumen comprises engaging the targeted wall with at least one engagement surface of an instrument working end and propagating a flowable media at a substantial velocity from at least one outlet in the engagement surface into the targeted tissue, wherein the flowable media modifies the structure in the targeted wall to modify electrical signal transmission therein. The method includes flowable media causing at least one of mechanical and thermal effects to modify the nerve fibers in the targeted wall. The method includes using flowable media that comprises water vapor and/or water droplets. In one method, the targeted tissue is in the renal arteries.

In another embodiment and method, the vapor can be generated from at least one of water, saline and alcohol. Further, the method can include introducing at least one pharmacologically active agent with the vapor. The pharmacologically active agent can be at least on one of an anesthetic, an antibiotic, a toxin and a sclerosing agent. Further, the method can included introducing an imaging enhancement media with the vapor.

The method of generating the flow of vapor can be by at least one of resistive heating means, inductive heating means, radiofrequency (RF) energy means, microwave energy means, photonic energy means, magnetic induction energy means, compression and decompression means together with heating means, and ultrasonic energy means.

Figure 21:
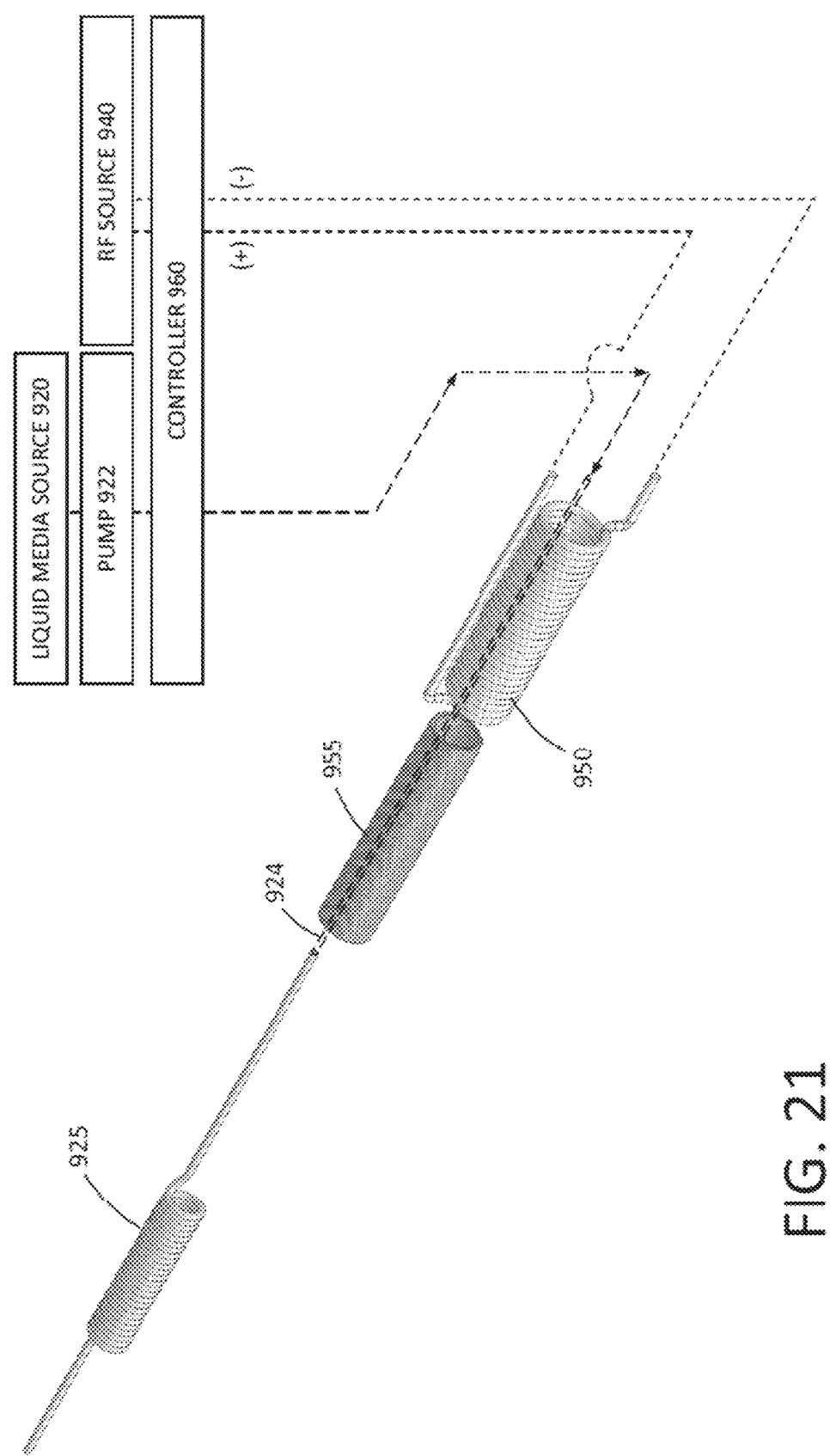
FIG. 21 is an exploded view of the components of the vapor delivery system of FIG. 19.

FIGS. 19-21 illustrate another embodiment of the invention that can be used for tumor ablation as well as, other soft tissue treatments, or other applications involving the application of energy as described herein. In one embodiment, the system comprises a vapor delivery tool 900 with a handle 902 that is coupled to an elongate vapor delivery member 910 with a working end 912 configured as a sharp-tip needle. The working end 912 has a plurality of vapor outlets 915 therein.

The handle 902 carries an inductive heating system for applying energy to a flow of liquid media in a flow channel therein, which is shown in exploded view in FIG. 21. As can be seen in FIG. 21, a liquid media source 920 and pump 922 provide a flow of liquid media to an interior channel 924 in an inductively heatable metal structure that in one variation comprises a stainless steel tubing formed into a helical tubing form 925. In one variation, the helical tubing 925 has an interior lumen or channel diameter of between 0.02" and 0.06" and channel length of between 50 cm and 200 cm. The outside diameter of the helical tubing assembly can be from 5 mm to 20 mm. In one variation, the helical tubing 925 can be formed so that each winding contacts an adjacent winding or the windings of the tubing can be dipped in a form of solder or similar inductively heatable material so that the entire assembly can be inductively heated efficiently. It should be appreciated that multiple sets of helical tubing 925 can be provided in a concentric assembly with one flow channel extending therethrough for providing an increased length flow channel. As with additional variations described herein, the dimensions of the device can vary as needed for the particular variation or application.

In a typical flow-based vapor delivery system described herein, one example of a pump 922 capable of being used with the system is a type of syringe pump known in the art that uses a stepper motor operatively coupled to controller 960 that allows for very precise control of flow rates of liquid media into the system.

It also has been found that a flow-based vapor delivery system as described herein is well suited for high velocity projection of vapor media from a probe working end to apply mechanical energy to dissect tissue, as disclosed in co-pending U.S. patent application Ser. No. 12/941,778 which is incorporated herein by reference.

In another embodiment, at least one type of electrical sensor can be provided in the fluid flow channel upstream and/or downstream of the inductively heatable helical tubing 925 with such a sensor configured to send signals to the controller 960. An upstream sensor can be an impedance or capacitance sensor to detect liquid media flows. Such a sensor can signal the controller of a normal flow and can detect a fault in the system, for example a failure of the pump 922, or a leak or kink in a liquid supply tubing that prevents a liquid flow through the system. A signal from such an upstream sensor can alert the user, or automatically shut down the system. A downstream sensor consisting of an impedance or capacitance sensor can signal the controller of a vapor flow rate or vapor quality based on an algorithm and look-up table of known impedance/capacitance values for flow rates and vapor quality. Again, such sensors can alert the user and/or automatically shut down the system if the system is not operating at selected or desired operational parameters.

In another embodiment described above that uses real-time imaging of a vapor ablation procedure, (e.g., ultrasound, MRI, etc.), the controller can be configured with additional algorithms that automatically alter vapor delivery parameters in response to imaging data of the treatment site. The modulation of energy delivery parameters can include at least one of vapor flow rate, vapor pressure, vapor delivery interval, vapor quality and orientation or programmed movement of the probe's vapor delivery outlets relative to the targeted site.

In another embodiment, the vapor delivery channel downstream from the vapor generator can be pre-heated to prevent condensation of vapor when initiating use of the "cold" system that has a vapor delivery channel at room temperature. In one variation, the vapor delivery channel includes a resistive heating element adapted to pre-heat the channel wall or a plastic or other PTC (positive temperature coefficient) material that allows heating of the channel wall. In any of these variations, a temperature sensing mechanism can communicate with the controller and interlock algorithm to signal user and to prevent vapor delivery before the channel wall reaches a selected temperature.

Referring to FIGS. 19 and 21, an electrical source or RF source 940 is operatively connected to a copper wire coil 950 that surrounds the helical tubing 925. The coil 950 does not physically or electrically contact the inner stainless steel helical tubing 925 and in one embodiment an insulator sleeve 955 is provided which can be any polymer or other dielectric material. In one variation, the copper coil 950 can comprise Litz wire which consists of multiple small insulated wires that can increase the power-carrying capacity of the coil. The RF source 940 can be configured for delivery of between 1 W and 3000 W. As can be seen in FIGS. 19 and 21, a controller 960 is provided for integrated control of both the pump 922 and the RF source 940. Electrical cables from the RF source 940 and flow tubing from the liquid media source 920 can be provided in a single conduit 962 which can be integrated with the non-disposable handle 902 or can be coupled to the handle 902 with a single detachable connector or a plurality of connectors.

It can be understood that all design parameters related to the RF source 940 and liquid flows in the system are inter-related, and in general, the system design can be based on the ultimate "cal/sec" rate of applying energy to tissue that is optimal for a particular procedure. In general, the inter-related design parameters include (i) ml/min of liquid media flow within the inductively heatable structure which further is dependent on flow channel diameter, flow channel length, and flow pressure; (ii) the Watts delivered by the RF source 940 which further relates to coil design (number of windings, types of wires in coil) and calculation of losses in the system to thereby apply selected Watts to the coil 950; and ultimately the vapor quality (i.e., the percent of the flow exiting a system vapor outlet that is phase changed to pure vapor as opposed to non-phase changed which may be liquid droplets). In one variation described below, the system provides a vapor media flow that is greater than 90% pure vapor and further provides an ultimate conversion efficiency of electrical energy to vapor energy of at least 60%.

In one variation, the system includes an RF source 940 that delivers 150W, uses water as a liquid media source with a pump 922 providing a flow rate of about 2.8 ml/min into a helical channel having a diameter of 0.05" and a length 90 cm with the helical tubing assembly having a diameter of 10 mm. The coil 950 surrounding the helical tubing delivers about 110 W to the helical tubing which results in 92% pure vapor at about 75 ml/min of vapor.

Referring to FIG. 19, it can be seen that the handle 902 which carries the helical tubing 925 and coil 950 is re-useable and detachable from elongate member 910 with a screw fitting 964. The handle 902 and more particularly the fluid channel 924 therein can be sterilized by running vapor through the system for a period of 1 to 10 minutes. The elongate member 910 in the embodiment shown in FIG. 19 comprises a vapor delivery needle which is disposable. The working end 912 of the elongated member 910 can comprise an exposed portion of a 16-30 gauge stainless steel needle shaft 965 having any suitable exposed length and any suitable number of vapor outlets 915 as described previously. As be seen in FIG. 19-21, the elongated member has an increased diameter section 970 that comprises an insulated section. In one variation shown in FIG. 22, an insulative space 972 can be air or a vacuum in a concentric space around the needle shaft 965. The outer sleeve 975 can be thin-wall stainless steel. In another embodiment, the insulative space 972 can be an aerogel or other insulative material and the outer sleeve 975 can be a metal or polymeric material. The dimensions of the insulative space can be designed to prevent the outer sleeve 975 from reaching a predetermined maximum temperature based on a particular vapor delivery interval during which vapor is flowing through the needle shaft 965.

Figure 23:
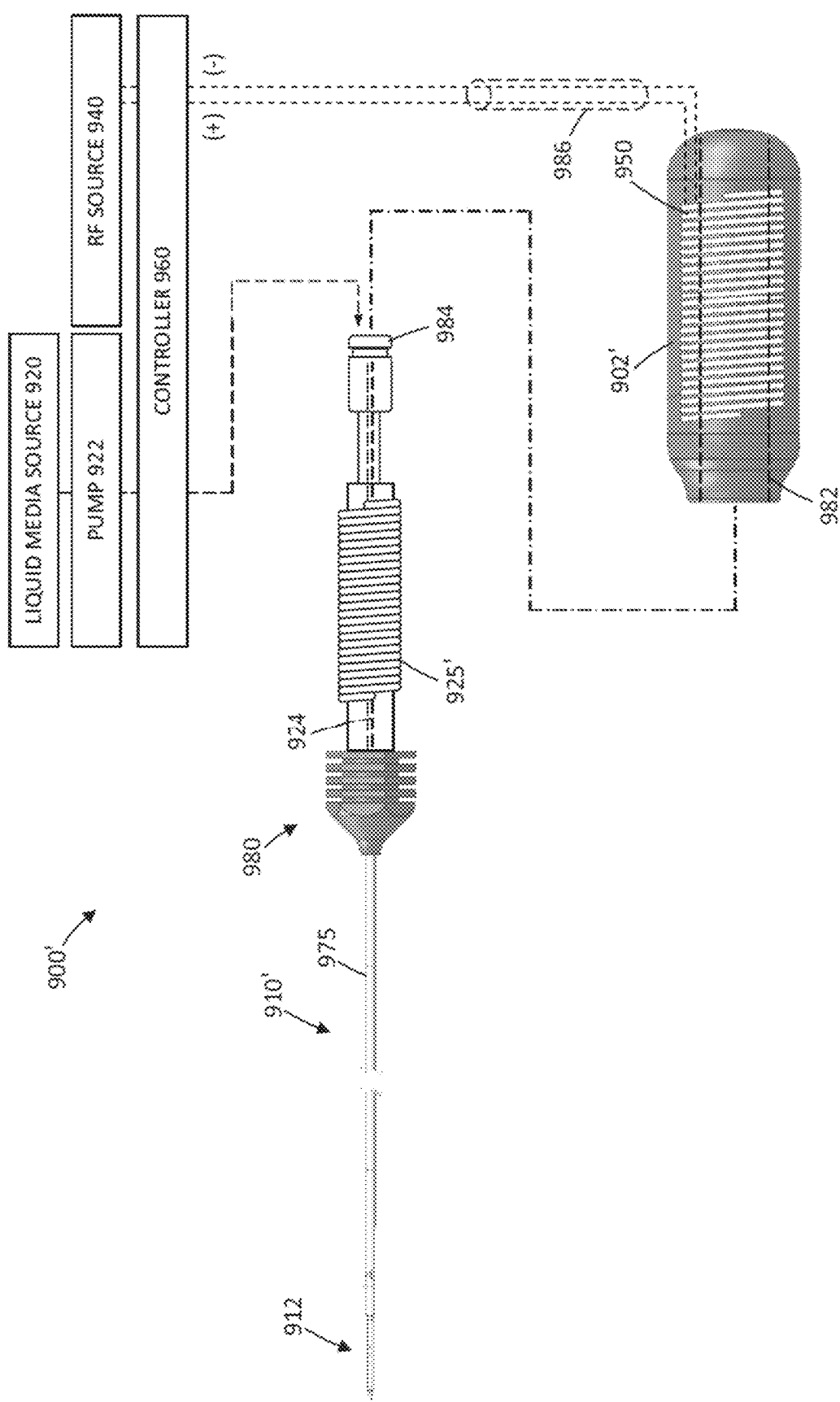
FIG. 23 is another embodiment of a vapor delivery system similar to that of FIG. 19 wherein the disposable assembly includes a vapor delivery needle portion together with an inductively heatable portion.

FIG. 23 illustrates another variation 900' which is similar to the embodiment of FIGS. 19-21 except that the handle 902' carries only the coil 950 which functions as described above. In the embodiment of FIG. 23, the elongate member 910' and helical tubing 925' comprise an assembly 980 which is detachable from handle 902'. The assembly 980 can slide into passageway 982 in the handle 902' and thus mate and cooperate with coil 950 for vaporizing a flow of liquid media therethrough. The assembly 980 has a proximal quick-connect fitting 984 that extends proximally from passageway 982 when mated with handle 902' to which a cooperating fitting (not shown) can be coupled to provide the liquid flow from the liquid media source 920. In this embodiment, an electrical cable 986 from the RF source 940 is coupled directly to handle 902'.

A method corresponding to the invention utilizing the system of FIGS. 19-21 or as otherwise described herein, for applying energy to a body structure includes controlling the flow of liquid media into the inductively heatable helical tubing structure 925 by utilizing the controller 960 to operate the pump 922, wherein the controlled flow of liquid media is then converted to vapor media having a predetermined flow rate to thereby provide a predetermined application of energy to tissue which be quantifiable, e.g., in cal/sec. Of particular interest, the use of the controlled liquid media flow allows delivery of a known amount of energy to tissue, or rate of energy delivery, which is not affected by the resistance of tissue to vapor propagation. In another form of vapor delivery system which delivers vapor from a boiler as described in co-pending U.S. patent application Ser. No. 12/167,155 filed Jul. 2, 2008, the pressure under which vapor is delivered into tissue is a function of boiler design and can be adversely affected by back-pressure or resistance within the targeted tissue, particularly in dense tissue, non-uniform tissue or fibrous tissue. In the use of such a "pressure-based" flow system, it is difficult to accurately determine the actual "rate" of energy delivery in dense or non-uniform tissue and therefore and it is difficult to set the appropriate vapor delivery time interval in seconds or minutes to ablate a particular targeted tissue volume. Thus, in general, a method corresponding to the invention consists of positioning a working end of a vapor delivery system at a targeted site in a body, providing a liquid media flow at a selected flow rate in the system and converting the liquid media to vapor media thereby providing a corresponding vapor flow rate and delivering the vapor media to the targeted site for selected time interval to thereby provide corresponding energy application ranging between 1 cal/sec to 500 cal/sec. In this method, the selected fluid flow rate can be controlled by controller 960 and pump 922 to provide liquid flow between 0.01 ml/min to 50 ml/min. In one variation, the liquid media is water although other fluids such as alcohol, etc. can be used. In this method, the corresponding vapor flow rate can be between 1 ml/min and 1500 ml/min of water vapor. The RF source 940 can be controlled by controller 960 to apply between 1W and 3000W for converting the liquid media to vapor media. The method includes allowing the physician to select a treatment time interval of between 1 sec and 5 minutes on the controller's user interface.

In another method of the invention, the controller 960 is configured to be programmable to allow the physician to select a vapor treatment that applies energy at a constant rate over a selected time interval. In another variation, the controller 960 is configured to allow the physician to select a vapor treatment that applies energy at a first constant rate over at least a first time interval, and then automatically at second constant rate over at least a second time interval. In yet another variation, the controller 960 can be configured to allow the physician to select a vapor treatment that modulates the applied energy over a selected time interval. In one embodiment, the controller has a user interface that allows selection of at least one of (i) the liquid media flow rate, (ii) the energy application rate; (iii) the vapor flow rate; and (iv) the vapor delivery time interval or intervals.

In another method of corresponding to the invention, the vapor delivery system and controller 960 are provided with an "idle" feature which idles the liquid and vapor flows at a very low level which is useful to pre-heat the flow channel and/or maintain the flow channel at a high temperature to thus allow for "instant-on" energy delivery without any appreciable condensation in the flow channel upon initiation of typical therapeutic liquid and vapor flows. In general, the physician can use the vapor idle feature with the system of FIGS. 19-21 which can include introducing a first flow of liquid media at a first liquid flow rate and converting the liquid media to vapor media, wherein the first vapor flow rate is configured for pre-heating and/or maintaining heat in the flow channel, and thereafter introducing a second flow of liquid media at second flow parameters and converting the liquid media to vapor media wherein second vapor flow rate is configured for exiting at least one vapor outlet to thereby apply energy to the body structure. The physician typically can use the idle feature before positioning the working end of the system in, or proximate to, the targeted site in a patient's body. The vapor idle feature has the further advantage of preventing gas and/or body fluids from migrating into the least one vapor outlet. The idle feature typically utilizes a liquid media flow rate of less than 1.0 ml/min. The system generally has a therapeutic liquid media flow rate that is greater than 1.0 ml/min.

In one variation of the system of FIGS. 19-21, the liquid media flow rate is selected by physician inputs on the user interface, and the controller 960 and RF source 940 deliver energy within a predetermined range suited for phase changing the liquid media flow to a vapor flow. As can be seen in FIG. 19, a temperature sensor 988 is coupled to the helical tubing 925 which sends temperature signals to the controller 960. The controller then includes algorithms for modulating RF power to maintain the temperature of the helical tubing at a pre-determined temperature, for example 120° C., although the targeted temperature could be any suitable temperature for the liquid media being supplied (e.g., 90° C. to 150° C.). The helical tubing 925 and flow path 924 within the system also can be configured with a pressure sensor 990 and an optional flow meter 992 independent of the pump 922, all communicating with the controller 960. In one embodiment, the controller has an algorithm that disables energy delivery from the RF source 940 if the temperature signals from the temperature sensor 988 are too high or the average temperature is too high over an interval or 1-20 seconds. In another variation, the controller 960 includes an algorithm that disables energy delivery from the RF source 940 if pressure sensed by the pressure sensor 990 is too high or averages pressure is too high over an interval or 1-20 seconds. In another variation, the controller includes an algorithm that disables energy delivery from the RF source 940 if the sensed flow rate from flow meter 992 does not correlate with the pre-selected flow rate that is supposed to be provided by the pump 922. The system also can include at least one pressure relief valve (not shown) in communication with the flow channel 924 to prevent unwanted pressure build-up within the system.

In general, the vapor treatment system comprises a handle 902 with an elongated member 910 coupled to the handle, an electrical source operatively coupled to a coil 950 within the handle 902, an inductively heatable structure 925 positioned proximate to the coil, a pump 922 and liquid media source 920 in communication with a flow channel 924 in the structure, the flow channel having an least one outlet 915 in a distal end of the elongated member, a controller operatively coupled to the electrical source and pump and at least one of a flow sensor, pressure sensor and temperature sensor for sending signals of operating parameters to the controller wherein the controller is configured to operate the electrical source and pump at selected parameters to inductively heat the structure to thereby convert a flow of the liquid media to a flow of vapor media in the flow channel which exits the at least one outlet to apply energy to body structure. The system controller includes a user interface configured with user-selectable pre-selects for at least one of (i) liquid media flow rate, (ii) liquid media flow interval, (iii) modulation of the liquid media flow rate within a time interval, (iv) energy application rate corresponding to energy released in a phase change of vapor to liquid, (v) pulsed flows of the liquid media and (vi) total applied energy. The system controller includes an algorithm to modulate electrical energy applied to the coil to maintain the temperature of the inductively heatable structure within any selected temperature range is between 90o C. and 150° C. In another embodiment, the system the controller includes an algorithm to modulate the liquid media flow rate to maintain the temperature of the inductively heatable structure within a selected range. In another embodiment, the system controller includes an algorithm and look-up table configured for selection of operating parameters of the electrical source corresponding to each user-selected liquid media flow rate.

In another method of the invention, it has been found that ablating certain soft tissue volumes such as tumors can be accomplished optimally by providing initial interval with vapor delivery parameters including a pulsed vapor flow followed by a second time interval with second parameters in which the vapor flow optionally is not pulsed. It has been found that first pulsed vapor flows and optional lower applied energy rates will shrink cell membranes and open extracellular spaces to thereafter allow higher vapor flows and applied energy rates which causes vapor to propagate extracellularly and to thereby cause complete cell death in a targeted tissue volume.

In general, a method for delivering energy to body tissue comprises introducing a working end of a vapor delivery probe into a targeted site in tissue, providing a flow of a condensable vapor under first operational parameters from the working end to modify the targeted site to permit enhanced extracellular vapor propagation therein and then providing a flow of the condensable vapor under second different flow parameters from the working end to cause cell death in the targeted site. The first operational parameters can includes a first flow rate that is higher or lower than a second flow rate of the second flow parameters. In one variation, the first operational parameters include a pulsed flow. In another variation, the second operational parameters include a non-pulsed flow.

In one embodiment, the vapor delivery system includes a flow channel extending to at least one outlet in a working end, a liquid media source and pump system configured to provide a flow of the liquid media into the flow channel, a heat source for converting the flow of the liquid media into a flow of vapor media in the flow channel and a controller adapted to control operating parameters of the liquid media source and heat source wherein the controller includes a user interface configured with user-selectable pre-selects for at least one of (i) liquid media flow rate, (ii) liquid media flow interval, (iii) modulation of the liquid media flow rate within a time interval, (iv) energy application rate corresponding to energy released in a phase change of vapor to liquid, (v) pulsed flows of the liquid media and (vi) total applied energy corresponding to energy released in a phase change of vapor to liquid. The controller can includes algorithms and a look-up table configured for selection of an operating parameters of the electrical source corresponding to each user-selected liquid media flow rate. The controller can include algorithms for modulating the liquid media flow rate in response to sensed temperature of an inductively heatable structure or the controller can include algorithms for modulating operating parameters of the heat source in response to a sensed temperature of the inductively heatable structure.

It has been found that the flow-based vapor delivery system as described above is optimal for many tissue ablation procedures, wherein the method for treating a site in a body structure, comprising positioning a working end of a vapor delivery probe at or proximate to a targeted site in a body and utilizing a pump system to provide a flow of liquid media at a predetermined fluid flow rate into the probe and converting the liquid media to vapor media thereby providing a corresponding vapor flow rate to the site, wherein the pump system is configured to deliver the liquid and vapor media at a substantially constant rate not affected by resistance to the flow of vapor media to the site. In one treatment, the targeted site is benign or malignant tumorous tissue. In another treatment, the targeted site is a uterine fibroid. In another treatment, the targeted site is lung tissue. In another treatment, the targeted site is a lung tumor or nodule. In another treatment, the targeted site is the inner lining of an esophagus. In another treatment, the targeted site is within a wall of a renal artery or the wall of a carotid artery. In another treatment, the targeted site is a baroreceptor or carotid body. In another treatment, the targeted site is nerve tissue. In one procedure, nerves can be ablated to treat migraine headaches. In another treatment, the targeted site is selected from the group including skin, adipose tissue, bone, disc, disc nucleus, ligaments, cartilage, synovial tissue, myelomas, cervical tissue, endometrium, digestive tract tissue, stomach walls, intestinal walls, hemorrhoids, soft palate, tongue tissue, an ulcer, wart, lymph node, breast duct, sinus tissue, arterial and venous malformations, vasculature, brain tissue, nerve roots in a tooth, heart tissue and eye tissue.

In another method of the invention, an imaging system can be used in conjunction with vapor delivery to visualize the vapor in real time during a procedure to ensure that the vapor is being delivered to the targeted site and/or to determine that an adequate vapor volume has been delivered to the site is soft tissue or within a body cavity or lumen. In one variation, ultrasound can be used for visualization because vapor is hyperechoic so what one sees on ultrasound can be exactly the treatment area. In another variation, magnetic resonance imaging can be used to show the temperature profile in tissue in almost real-time. In another variation, a CT scan can be used and vapor can be imaged if a contrast agent (e.g., Iodine) is added to the liquid media source. Further, data from any of these imaging systems can be sent to a computer software program that can convert the data into 3D images on a screen which can then be used together with a tracking device on the tip of the vapor delivery probe to guide the tip to the target site in tissue.

In another embodiment, the user interface in the controller 960 can be adapted to generate an image representation of a potential treatment site in a subject on a screen. The physician then outlines on the screen a targeted treatment site in 2D or 3D. Thereafter, the controller 960 can use the "outlined" treatment site on the screen to determine the optimal treatment operating parameters to ablate the site.

Figure 24:
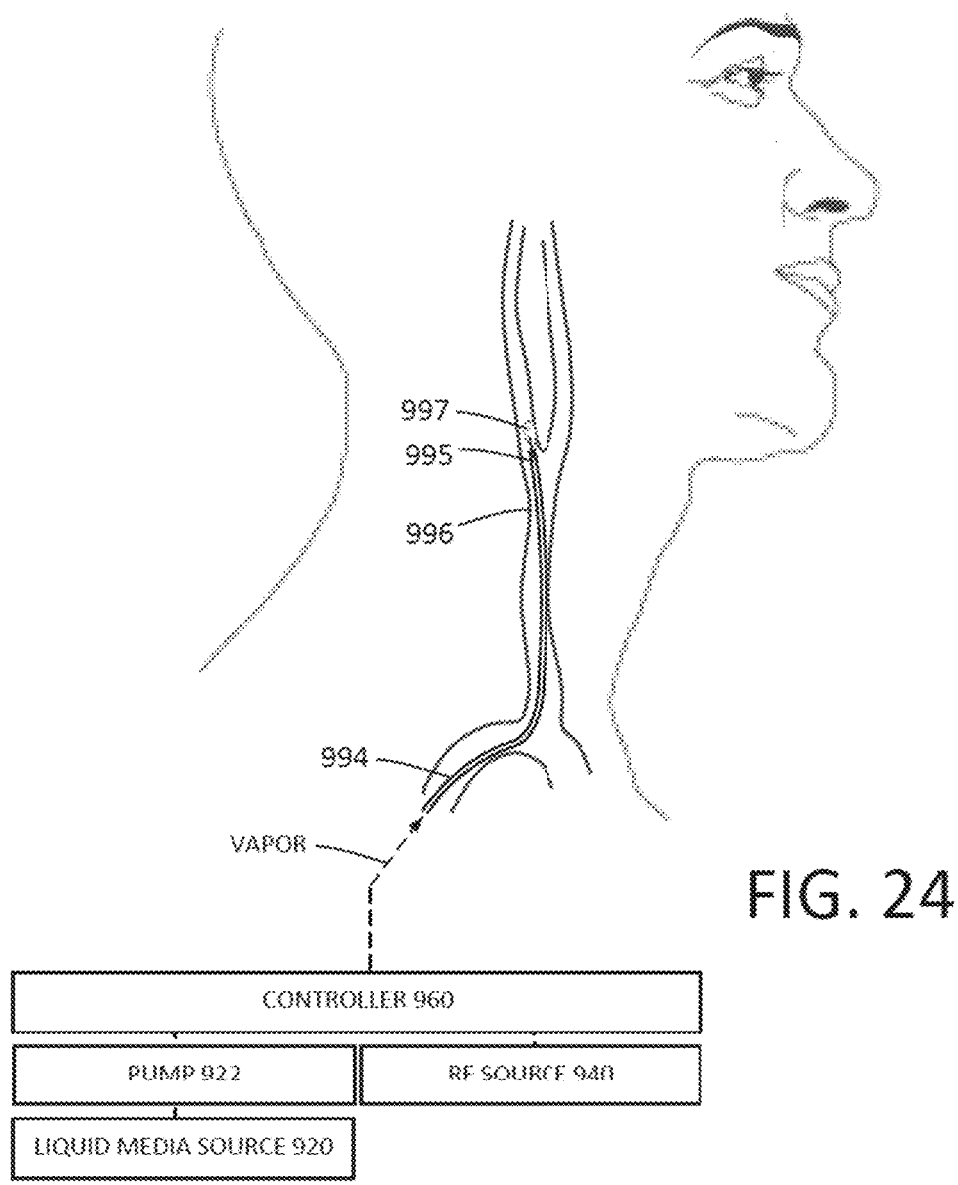
FIG. 24 is another variation of a vapor delivery system and method for using vapor delivery to treat a blood pressure disorder by modifying the function of a baroreceptor in an arterial wall.

FIG. 24 illustrates another apparatus and method of the invention for treating a blood pressure disorder by using thermal energy to modify function of a baroreceptor in a human or mammalian body. Baroreceptors consist of a form of mechanoreceptor that detects pressure of a blood flow in a vessel lumen which can signal the central nervous system to increase or decrease total peripheral resistance to blood flow and cardiac output. Baroreceptors function as a component of a negative feedback system called the baroreflex to alter mean arterial blood pressure. Arterial baroreceptors are stimulated by stretching or distortion of the arterial walls when blood pressure changes. The baroreceptors can identify the changes in both the average blood pressure or the rate of change in pressure with each arterial pulse, and can signal the nervous system in response to such stretching. FIG. 24 illustrates a vapor delivery catheter 994 having a working end 995 navigated within carotid artery 996 to a location proximate a baroreceptor 997. A vapor delivery needle tip, similar to that of FIG. 11E, can be introduced into the baroreceptor tissue to deliver vapor to ablate or modify function of the baroreceptor. Any of the working end embodiments with positioning balloons of FIGS. 11B-18 can be used to treat a baroreceptor.

Figure 25:
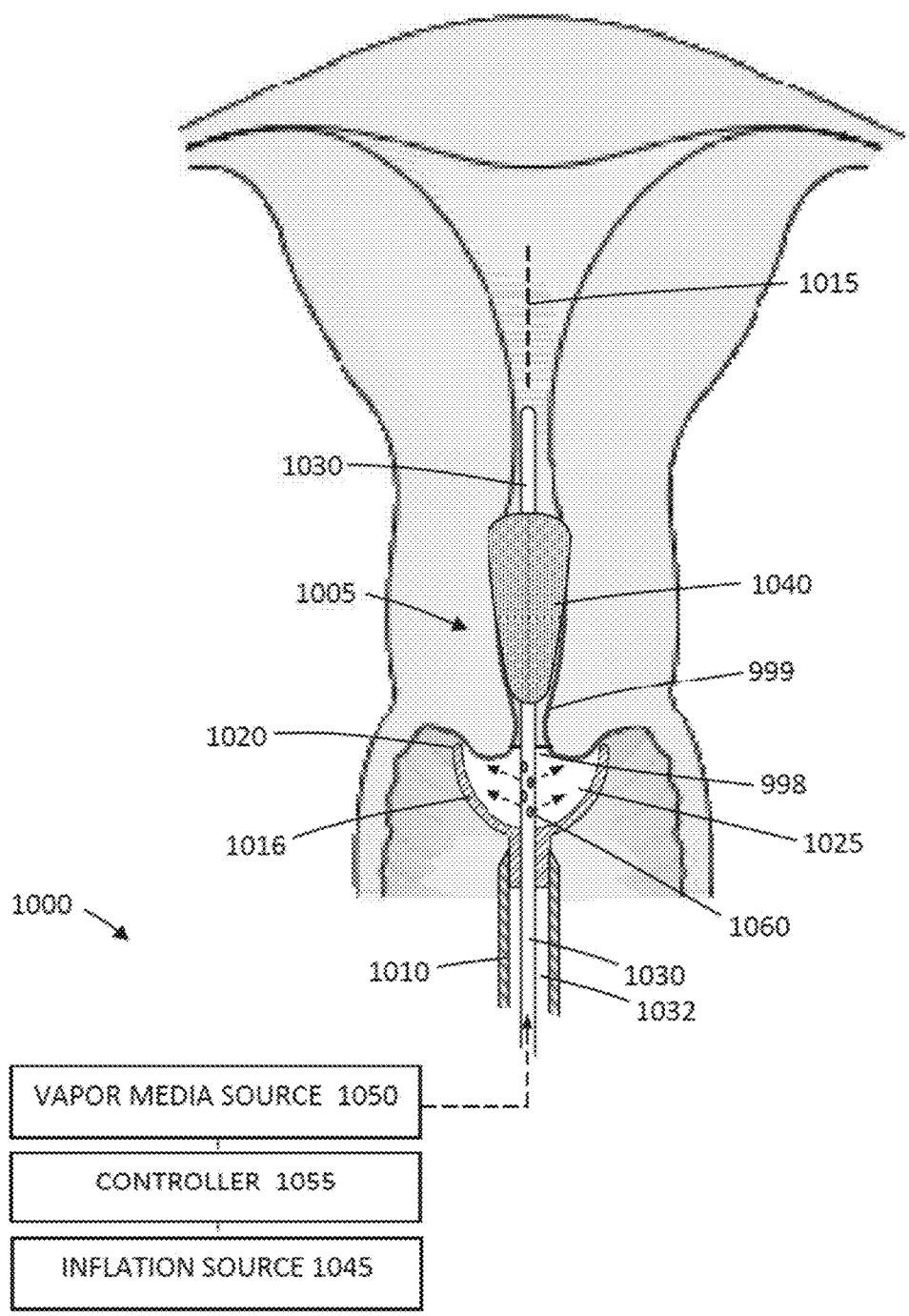
FIG. 25 is another variation of a vapor delivery system and method for using vapor to treat cervical neoplasia.

FIG. 25 illustrates another method and apparatus of the invention for treating a cervical neoplasia. Cervical intraepithelial neoplasia (CIN) is routinely treated with a procedure called conization. Such conization of the cervix 998 is defined as excision of a cone-shaped or cylindrical wedge from the cervix that includes the transformation zone and potentially portions of the endocervical canal 999. In FIG. 25, the system and probe 1000 have a working end 1005 that includes a vapor media inflow channel extending to a concavity of the working end that engages tissue and contains the vapor media. In the embodiment of FIG. 25, the probe introducer or shaft 1010 extends along axis 1015 from a handle (not shown) to a bell-shaped structure 1016 with a perimeter 1020 that contacts tissue about the cervix 1022.

The diameter of the perimeter can range from about 1 cm to 4 cm and in one embodiment, the bell-shaped structure 1016 is a resilient silicone. The structure 1016 provides a concavity 1025 which contains vapor media. The thickness of the structure 1016 is sufficient to permit the physician to press the structure into tissue and to prevent vapor escape around the perimeter 1020.

FIG. 25 further illustrates an elongate vapor delivery sleeve 1030 that is axially slidable in bore 1032 in the bell-shaped structure 1016. The sleeve 1030 carries an expandable member such as occlusion balloon 1040 that is configured for expansion in the cervical canal 1042 to seal the canal at a selected location therein. Thus, the axial dimension between the bell-shaped structure 1016 and occlusion balloon 1040 is adjustable to allow the physician to position the balloon at any shallow or deeper depth in the endocervical canal. The balloon 1040 is inflated from an inflation source 1045 that can comprise a syringe or other mechanism for providing a pressurized liquid or gas to inflate the balloon.

In a method of use, still referring to FIG. 25, vapor is introduced from vapor source 1050 and controlled by controller 1055 through a lumen in vapor delivery sleeve 1030 to exit outlets 1060 distal to bell-shaped structure 1016. The vapor then condenses and releases energy to contact and ablate tissue intermediate the bell-shaped structure 1016 and the occlusion balloon 1040. The vapor can be provided in a treatment interval ranging from 10 seconds to about 4 minutes to ablate to any desired depth, which can be from 0.5 mm to 1 cm or more. In another embodiment, the perimeter of the bell-shaped structure 1016 and/or the balloon 1040 can be infused with a cooling fluid to cool adjacent tissue. The bell-shaped structure 1016 and optionally the balloon 1040 can carry thermocouples that are operationally connected to the controller to modulate or terminate energy delivery.

In general, a method of the invention of treating a cervical neoplasia comprised generating a flow of vapor, positioning a vapor containing structure about the external cervical os, introducing the flow of vapor into contact with targeted cervical tissue, delivering thermal energy to the targeted tissue via a vapor-to-liquid phase transition of the vapor, and modifying the targeted tissue. The method includes the delivery of water vapor, and optionally can deliver a pharmacological agent. The cervical tissue can be ablated to a depth of at least 0.5 mm, at least 1 mm, at least 2 mm, at least 3 mm, at least 4 mm or at least 5 mm. The cervical tissue can be ablated radially outward from the external os a distance of at least 1 mm, at least 5 mm, or at least 10 mm. The method includes positioning the containment structure by manually pressing a perimeter of the containment structure against the tissue outward of the external cervical os.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for treating adipose tissue in a human subject, comprising:
    providing a probe having a handle coupled to an elongate shaft with a working end;
    positioning the working end at a targeted site in the adipose tissue;
    providing a flow of liquid media at a selected fluid flow rate and converting the liquid media to vapor media within a helical element in the handle; and
    delivering the vapor media through the shaft and working end to the targeted site for a selected time interval thereby delivering ablative energy to the targeted site.

2. The method of claim 1, wherein the selected fluid flow rate is between 0.01 ml/min to 50 ml/min.

3. The method of claim 1, wherein a corresponding vapor flow rate is between 1 ml/min to 1500 ml/min.

4. The method of claim 1, wherein an energy applied for converting the liquid media to vapor media is between 1 W and 3000 W.

5. The method of claim 1, wherein the selected time interval is between 1 second and 1 minute.

6. The method of claim 1, wherein converting includes actuating an electrical source configured to heat the helical element in the handle, wherein the helical element comprises a flow channel.

7. The method of claim 6, wherein the flow channel within the helical element has a diameter ranging from 0.01" to 0.10".

8. The method of claim 6, wherein the flow channel within the helical element has a length ranging from 10 cm and 500 cm.

9. The method of claim 1, wherein the selected fluid flow rate is maintained at a constant rate over the selected time interval.

10. The method of claim 1, further comprising selecting an energy application rate on a controller interface.

11. The method of claim 1, further comprising selecting the time interval on a controller interface.

12. The method of claim 1, further comprising selecting a total calories applied to tissue on a controller interface.

13. The method of claim 1, wherein a flow controller is programmable to maintain the fluid flow rate at a constant over the selected time interval.

14. The method of claim 1, wherein the energy delivered to the targeted site corresponds to a controlled energy application of between 1 cal/sec to 500 cal/sec.

\* \* \* \* \*